United States Patent
McMahon et al.

(10) Patent No.: US 12,414,707 B2
(45) Date of Patent: Sep. 16, 2025

(54) APPARATUS, SYSTEM, AND METHOD FOR DETECTING PHYSIOLOGICAL MOVEMENT FROM AUDIO AND MULTIMODAL SIGNALS

(71) Applicant: RESMED SENSOR TECHNOLOGIES LIMITED, Sandyford (IE)

(72) Inventors: Stephen McMahon, Dublin (IE); Damien O'Rourke, Dublin (IE); Alberto Zaffaroni, Dublin (IE); Redmond Shouldice, Clonskeagh (IE); Tony Fagan, Dublin (IE); Niall Fox, Dublin (IE); Niall O'Mahony, Dublin (IE); Graeme Lyon, Dublin (IE)

(73) Assignee: ResMed Sensor Technologies Limited (IE)

( * ) Notice: Subject to any disclaimer, the term of this patent is extended or adjusted under 35 U.S.C. 154(b) by 1091 days.

(21) Appl. No.: 16/332,629

(22) PCT Filed: Sep. 19, 2017

(86) PCT No.: PCT/EP2017/073613
§ 371 (c)(1),
(2) Date: Mar. 12, 2019

(87) PCT Pub. No.: WO2018/050913
PCT Pub. Date: Mar. 22, 2018

(65) Prior Publication Data
US 2021/0275056 A1 Sep. 9, 2021

Related U.S. Application Data

(60) Provisional application No. 62/396,616, filed on Sep. 19, 2016.

(51) Int. Cl.
*A61B 5/08* (2006.01)
*A61B 5/00* (2006.01)
(Continued)

(52) U.S. Cl.
CPC .......... *A61B 5/0816* (2013.01); *A61B 5/1126* (2013.01); *A61B 5/6887* (2013.01);
(Continued)

(58) Field of Classification Search
CPC ... A61B 5/0816; A61B 5/1126; A61B 5/6887; A61B 5/7228; A61B 5/4812; A61B 5/4818; G16H 40/67; H04R 1/222
(Continued)

(56) References Cited

U.S. PATENT DOCUMENTS

| 9,430,938 B2 | 8/2016 | Proud |
| 9,993,166 B1 | 6/2018 | Johnson et al. |

(Continued)

FOREIGN PATENT DOCUMENTS

| CN | 102650526 A | 8/2012 |
| CN | 104644143 A | 5/2015 |

(Continued)

OTHER PUBLICATIONS

Let's Clear Up Some Things About Sweeps . . . .*
(Continued)

*Primary Examiner* — Alex M Valvis
*Assistant Examiner* — Chanel J Jhin
(74) *Attorney, Agent, or Firm* — Botos Churchill IP Law LLP

(57) ABSTRACT

Methods and devices provide physiological movement detection with active sound generation. In some versions, a processor may detect breathing and/or gross body motion. The processor may control producing, via a speaker coupled to the processor, a sound signal in a user's vicinity. The processor may control sensing, via a microphone coupled to the processor, a reflected sound signal. This reflected sound signal is a reflection of the sound signal from the user. The processor may process the reflected sound, such as by a
(Continued)

demodulation technique. The processor may detect breathing from the processed reflected sound signal. The sound signal may be produced as a series of tone pairs in a frame of slots or as a phase-continuous repeated waveform having changing frequencies (e.g., triangular or ramp sawtooth). Evaluation of detected movement information may determine sleep states or scoring, fatigue indications, subject recognition, chronic disease monitoring/prediction, and other output parameters.

40 Claims, 33 Drawing Sheets

(51) Int. Cl.
    *A61B 5/11*     (2006.01)
    *G16H 40/67*     (2018.01)
    *H04R 1/22*     (2006.01)

(52) U.S. Cl.
    CPC .......... *A61B 5/7228* (2013.01); *G16H 40/67* (2018.01); *A61B 5/4812* (2013.01); *A61B 5/4818* (2013.01); *H04R 1/222* (2013.01)

(58) Field of Classification Search
    USPC ........................................................ 600/534
    See application file for complete search history.

(56) References Cited

U.S. PATENT DOCUMENTS

| | | | |
|---|---|---|---|
| 10,004,451 | B1 | 6/2018 | Proud |
| 10,009,581 | B2 | 6/2018 | Proud |
| 2004/0242997 | A1 | 12/2004 | Griffin et al. |
| 2008/0304044 | A1 | 12/2008 | Cooper et al. |
| 2009/0318777 | A1 | 12/2009 | Kameyama |
| 2010/0208631 | A1 | 8/2010 | Zhang et al. |
| 2011/0019846 | A1 | 1/2011 | Anderson |
| 2014/0194793 | A1 | 7/2014 | Nakata et al. |

FOREIGN PATENT DOCUMENTS

| | | |
|---|---|---|
| CN | 104812300 A | 7/2015 |
| EP | 0525858 A2 | 2/1993 |
| EP | 1986020 A2 | 10/2008 |
| JP | H03162837 A | 7/1991 |
| JP | 2000304859 A | 11/2000 |
| JP | 2000346685 A | 12/2000 |
| JP | 2008000222 A | 1/2008 |
| JP | 2009000326 A | 1/2009 |
| JP | 2009538720 A | 11/2009 |
| JP | 2012070874 A | 4/2012 |
| JP | 2015228159 A | 12/2015 |
| JP | 2016042914 A | 4/2016 |
| JP | 2018504166 A | 2/2018 |
| WO | 03016940 A2 | 2/2003 |
| WO | 2007124126 A2 | 11/2007 |
| WO | 2007143535 A3 | 8/2008 |
| WO | 2015006364 A2 | 1/2015 |
| WO | 2015061848 A1 | 5/2015 |
| WO | 2016093927 A2 | 6/2016 |
| WO | 2016145483 A1 | 9/2016 |

OTHER PUBLICATIONS

Let's Clear Up Some Things About Sweeps Part 2.*
First Office Action issued in corresponding CN application No. 2017800692184 on May 20, 2021.
Office Action for Japanese Patent Application No. 2019-515446, Nov. 4, 2021.
International Search Report issued in corresponding PCT Application No. PCT/EP2017/073613 on Dec. 20, 2017.
Notice of Allowance issued in Chinese Patent Application No. 2017800692184, mailed Oct. 25, 2022, 9 pages.
Extended European Search Report issued in European Patent Application No. 22189425.6, mailed Jan. 27, 2023, 8 pages.
Office Action issued in corresponding Japanese Patent Application No. 2022-115208, mailed Oct. 3, 2023, 7 pages.
Office Action issued in corresponding U.S. Appl. No. 17/871,280 mailed Dec. 2, 2024, 46 pages.
Office Action issued in corresponding Japanese Patent Application No.2022-115208, mailed Jul. 1, 2025, 28 pages.

* cited by examiner

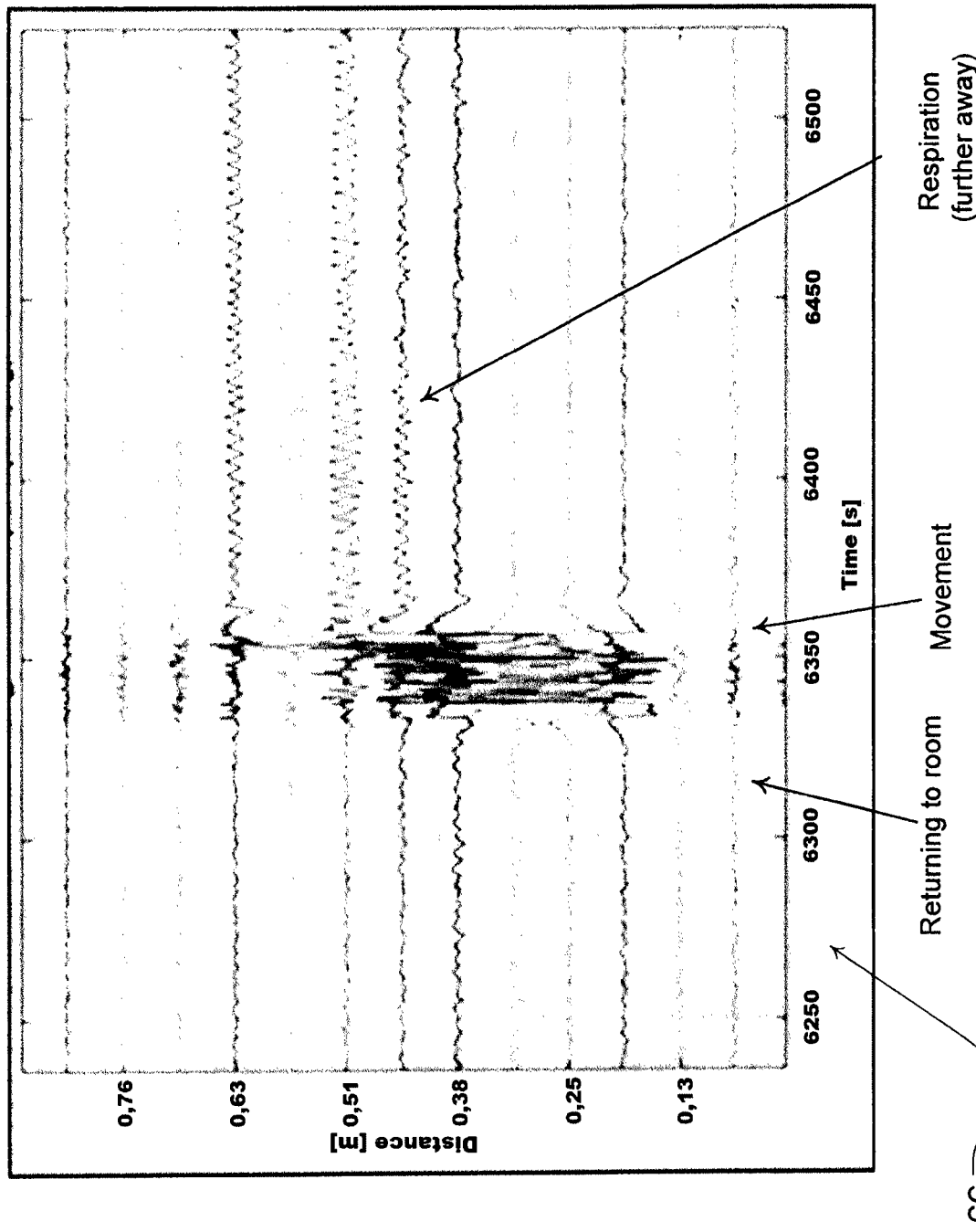

APPARATUS, SYSTEM, AND METHOD FOR DETECTING PHYSIOLOGICAL MOVEMENT FROM AUDIO AND MULTIMODAL SIGNALS

1 CROSS REFERENCE TO RELATED APPLICATIONS

The present application is a national phase entry under 35 U.S.C. § 371 of International Application No. PCT/EP2017/073613 filed Sep. 19, 2017, published in English, which claims priority from U.S. Provisional Patent Application No. 62/396,616 filed Sep. 19, 2016, all of the disclosure of which are incorporated herein by reference.

2 BACKGROUND OF THE TECHNOLOGY

2.1 Field of the Technology

The present technology relates to detecting bio-motion associated with living subjects. More particularly, the present technology relates to using acoustic sensing to detect physiological movement such as breathing movement, cardiac movement and/or other less cyclical body movement of a living subject.

2.2 Description of the Related Art

Monitoring the breathing and body (including limb) movement of a person, for example, during sleep, can be useful in many ways. For example, such monitoring could be useful in monitoring and/or diagnosing sleep disordered breathing conditions, such as sleep apnea. Traditionally, the barrier to entry for active radio location or ranging application is that specialized hardware circuitry and antennas are required.

Smartphones and other portable electronic communication devices have been ubiquitous in daily life, even in developing countries where landlines are not available. It would be desirable to have a method for monitoring bio-motion (i.e., physiological movement) in an efficient, effective manner that does not require specialized equipment. The realization of such a system and method would address a considerable technical challenge.

3 BRIEF SUMMARY OF THE TECHNOLOGY

The present technology concerns systems, methods, and apparatus for detecting movement of a subject, for example, while the subject is asleep. Based on such movement detection, including for example breathing movement, the subject's movements, sleep related characteristics, sleep state and/or apnea events may be detected. More particularly, a mobile application associated with a mobile device, such as a smartphone, tablet, etc. uses the mobile device sensors, such as an integrated, and/or externally connectable, speaker and microphone to detect breathing and motion.

Some versions of the present technology may include a processor-readable medium, having stored thereon processor-executable instructions which, when executed by a processor, cause the processor to detect physiological movement of a user. The processor-executable instructions may comprise instructions to control producing, via a speaker coupled to an electronic processing device, a sound signal in a vicinity that includes a user. The processor-executable instructions may comprise instructions to control sensing, via a microphone coupled to the electronic processing device, a sound signal reflected from the user. The processor-executable instructions may comprise instructions to process the sensed sound signal. The processor-executable instructions may comprise instructions to detect a breathing signal from the processed sound signal.

In some versions, the sound signal may be in an inaudible sound range. The sound signal may include a tone pair forming a pulse. The sound signal may include a sequence of frames. Each of the frames of the sequence may comprise a series of tone pairs where each tone pair is associated with a respective time slot within the frame. A tone pair may include a first frequency and a second frequency. The first frequency and second frequency may be different. The first frequency and second frequency may be orthogonal to each other. The series of tone pairs in a frame may comprise a first tone pair and a second tone pair, wherein frequencies of a first tone pair may be different from frequencies of a second tone pair. A tone pair of a time slot of the frame may have a zero amplitude at a beginning and an end of the time slot, and may have a ramping amplitude to and from a peak amplitude between the beginning and the end.

In some versions, a time width of the frame may vary. The time width may be a width of a slot of the frame. The time width may be a width of the frame. A sequence of tone pairs of a frame of slots may form a pattern of different frequencies with respect to different slots of the frame. The pattern of different frequencies may repeat in a plurality of frames. The pattern of different frequencies may change for different frames of slots in a plurality of frames of slots.

In some versions, the instructions to control producing the sound signal may include a tone pair frame modulator. The instructions to control sensing the sound signal reflected from the user may include a frame buffer. The instructions to process the sensed sound signal reflected from the user may include a demodulator to produce one or more baseband motion signals comprising the breathing signal. The demodulator may produce a plurality of baseband motion signals, where the plurality of baseband motion signals may include quadrature baseband motion signals.

In some versions, the processor-readable medium may include processor-executable instructions to process the plurality of baseband motion signals. The processor-executable instructions to process the plurality of baseband motion signals may include an intermediate frequency processing module and an optimization processing module, to produce a combined baseband motion signal from the plurality of baseband motion signals. The combined baseband motion signal may include the breathing signal. In some versions, the instructions to detect the breathing signal may comprise determining a breathing rate from the combined baseband motion signal. In some versions of the sound signal, a duration of a respective time slot of the frame may be equal to one divided by a difference between frequencies of a tone pair.

In some versions of the present technology, the sound signal may include a repeated waveform with changing frequencies. The repeated waveform may be phase-continuous. The repeated waveform with changing frequencies may include one of a ramp sawtooth, triangular and a sinusoidal waveform. The processor-readable medium may further include processor-executable instructions including instructions to vary one or more parameters of a form of the repeated waveform. The one or more parameters may include any one or more of (a) a location of a peak in a repeated portion of the repeated waveform, (b) a slope of a ramp of a repeated portion of the repeated waveform, and (c) a frequency range of a repeated portion of the repeated waveform. In some versions, a repeated portion of the repeated waveform may be a linear function or a curve function that changes frequency of the repeated portion. In some versions, the repeated waveform with changing frequencies may include a symmetric triangular waveform. In some versions, the instructions to control producing the sound signal include instruction to loop sound data representing a waveform of the repeated waveform. The instructions to control sensing the sound signal reflected from the user may include instructions to store sound data sampled from the microphone. The instructions to control processing the sensed sound signal may include instruction to correlate the produced sound signal with the sensed sound signal to check synchronization.

In some versions, the instructions to process the sensed sound signal may include a down converter to produce data comprising the breathing signal. The down converter may mix a signal representing the produced sound signal with the sensed sound signal. The down converter may filter an output of the mixing of a signal representing the produced sound signal and the sensed sound signal. The down converter may window a filtered output of the mixing of the signal representing the produced sound signal and the sensed sound signal. The down converter may produce a frequency domain transformation matrix of a windowed filtered output of the mixing of the signal representing the produced sound signal and the sensed sound signal. The processor-executable instructions to detect the breathing signal may extract amplitude and phase information from multiple channels of a data matrix produced by the down converter. The processor-executable instructions to detect the breathing signal may further include processor-executable instructions to calculate a plurality of features from the data matrix. The plurality of features may include any one of more of (a) an In-band squared over full band metric, (b) an in-band metric, (c) a Kurtosis metric, and (d) a frequency domain analysis metric. The processor-executable instructions to detect the breathing signal may generate a breathing rate based on the plurality of features.

In some versions, the processor-executable instructions may further include instructions to calibrate sound-based detection of body movement that by an assessment of one or more characteristics of the electronic processing device. The processor-executable instructions may further include instructions to generate the sound signal based on the assessment. The instructions to calibrate sound-based detection may determine at least one hardware, environment, or user specific characteristic. The processor-executable instructions may further include instructions to operate a pet set up mode wherein a frequency for producing the sound signal may be selected based on user input and for producing one or more test sound signals.

In some versions, the processor-executable instructions may further include instructions to discontinue producing the sound signal based on a detected user interaction with the electronic processing device. The detected user interaction may include any one or more of: detection of movement of the electronic processing device with an accelerometer, detection of pressing of a button, detection of touching of a screen, detection of an incoming phone call. The processor-executable instructions may further include instructions to initiate producing the sound signal based on a detected absence of user interaction with the electronic processing device.

In some versions, the processor-executable instructions may further include instructions to detect gross body movement based on processing of the sensed sound signal reflected from the user. In some versions, the processor-executable instructions may further include instructions to process audio signals sensed via the microphone to evaluate any one or more of environmental sounds, speech sounds and breathing sounds to detect user motion. In some versions, the processor-executable instructions may further include instructions to process a breathing signal to determine any one or more of (a) a sleep state indicating sleep; (b) a sleep state indicating awake; (c) a sleep stage indicating deep sleep; (d) a sleep stage indicating light sleep; and (e) a sleep stage indicating REM sleep.

In some versions, the processor-executable instructions may further include instructions to operate a setup mode to detect sound frequencies in a vicinity of the electronic processing device and select a frequency range for the sound signal that is different from the detected sound frequencies. In some versions, the instructions to operate the setup mode may select a range of frequencies non-overlapping with the detected sound frequencies.

In some versions of the present technology, a server may have access to any of the processor-readable mediums described herein. The server may be configured to receive requests for downloading the processor-executable instructions of the processor-readable medium(s) to an electronic processing device over a network.

In some versions of the present technology, a mobile electronic device or electronic processing device may include one or more processors; a speaker coupled to the one or more processors; a microphone coupled to the one or more processors; and a processor-readable medium of any of the processor readable mediums describe herein.

Some versions of the present technology involve a method of a server having access to any processor-readable medium described herein. The method may include receiving, at the server, a request for downloading the processor-executable instructions of the processor-readable medium to an electronic processing device over a network. The method may also include transmitting the processor-executable instructions to the electronic processing device in response to the request.

Some versions of the present technology involve a method of a processor for detecting body movement using a mobile electronic device. The method may include accessing, with a processor, any of the processor-readable mediums described herein. The method may include executing, in the processor, any of the processor-executable instructions of the processor readable medium(s).

Some versions of the present technology involve a method of a processor for detecting body movement using a mobile electronic device. The method may include controlling producing, via a speaker coupled to the mobile electronic device, a sound signal in a vicinity that includes a user. The method may include controlling sensing, via a microphone coupled to the mobile electronic device, a sound signal reflected from the user. The method may include processing the sensed reflected sound signal. The method may include detecting a breathing signal from the processed reflected sound signal.

Some versions of the present technology involve a method for detecting movement and breathing using a mobile electronic device. The method may include transmitting, via a speaker on the mobile electronic device, a sound signal towards a user. The method may include sensing, via a microphone on the mobile electronic device, a reflected sound signal, the reflected sound signal being reflected from the user. The method may include detecting a breathing and motion signal from the reflected sound signal. The sound signal may be an inaudible or audible sound signal. In some versions, prior to transmitting, the method may involve modulating the sound signal using one of a FMCW modulation scheme, a FHRG modulation scheme, an AFHRG modulation scheme, a CW modulation scheme, a UWB modulation scheme, or an ACW modulation scheme. Optionally, the sound signal may be a modulated low frequency ultrasonic sound signal. The signal may include a plurality of frequency pairs transmitted as a frame. In some versions, upon sensing the reflected sound signal, the method may include demodulating the reflected sound signal. The demodulating may include performing a filter operation on the reflected sound signal; and synchronizing the filtered reflected sound signal with timing of the transmitted sound signal. In some versions generating the sound signal may include performing a calibration function to assess one or more characteristics of the mobile electronic device; and generating the sound signal based on the calibration function. The calibration function may be configured to determine at least one hardware, environment, or user specific characteristic. The filter operation may include a high pass filter operation.

Some versions of the present technology involve a method of detecting motion and breathing. The method may include producing a sound signal directed towards a user. The method may include sensing a sound signal reflected from the user. The method may include detecting a breathing and motion signal from the sensed reflected sound signal. In some versions the producing, transmitting, sensing, and detecting may be performed at a bedside device. Optionally, the bedside device may be a therapy device such as CPAP device.

The methods, systems, devices and apparatus described herein can provide improved functioning in a processor, such as of a processor of a general or specific purpose computer, portable computer processing device (e.g., mobile phone, tablet computer etc.), respiratory monitor and/or other respiratory apparatus utilizing a microphone and speaker. Moreover, the described methods, systems, devices and apparatus can provide improvements in the technological field of automated management, monitoring and/or prevention and/or evaluation of respiratory condition and sleep condition, including, for example, sleep apnea.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

FIG. 23C is a portion of the signals graph of FIG. 23A showing area CC from FIG. 23A.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing particular examples discussed and is not intended to be limiting.

The following description is provided in relation to various forms of the present technology that may share common characteristics or features. It is to be understood that one or more features of any one exemplary form may be combinable with one or more features of another form. In addition, any single feature or combination of features in any of form described herein may constitute a further exemplary form.

5.1 Screening, Monitoring, and Diagnosis

The present technology concerns systems, methods, and apparatus for detecting movement of a subject, including, for example, breathing movement and/or cardiac related chest movement, such as while the subject is asleep. Based on such breathing and/or other movement detection, the subject's sleep state and apnea events may be detected. More particularly, a mobile application associated with a mobile device, such as a smartphone, tablet, etc. uses the mobile device sensors, such as a speaker and microphone to detect such motion.

Figure 1:
FIG. 1 illustrates an example processing device for receiving audio information from a sleeper that may be suitable for implementation of the processes of the present technology.
Figure 2:
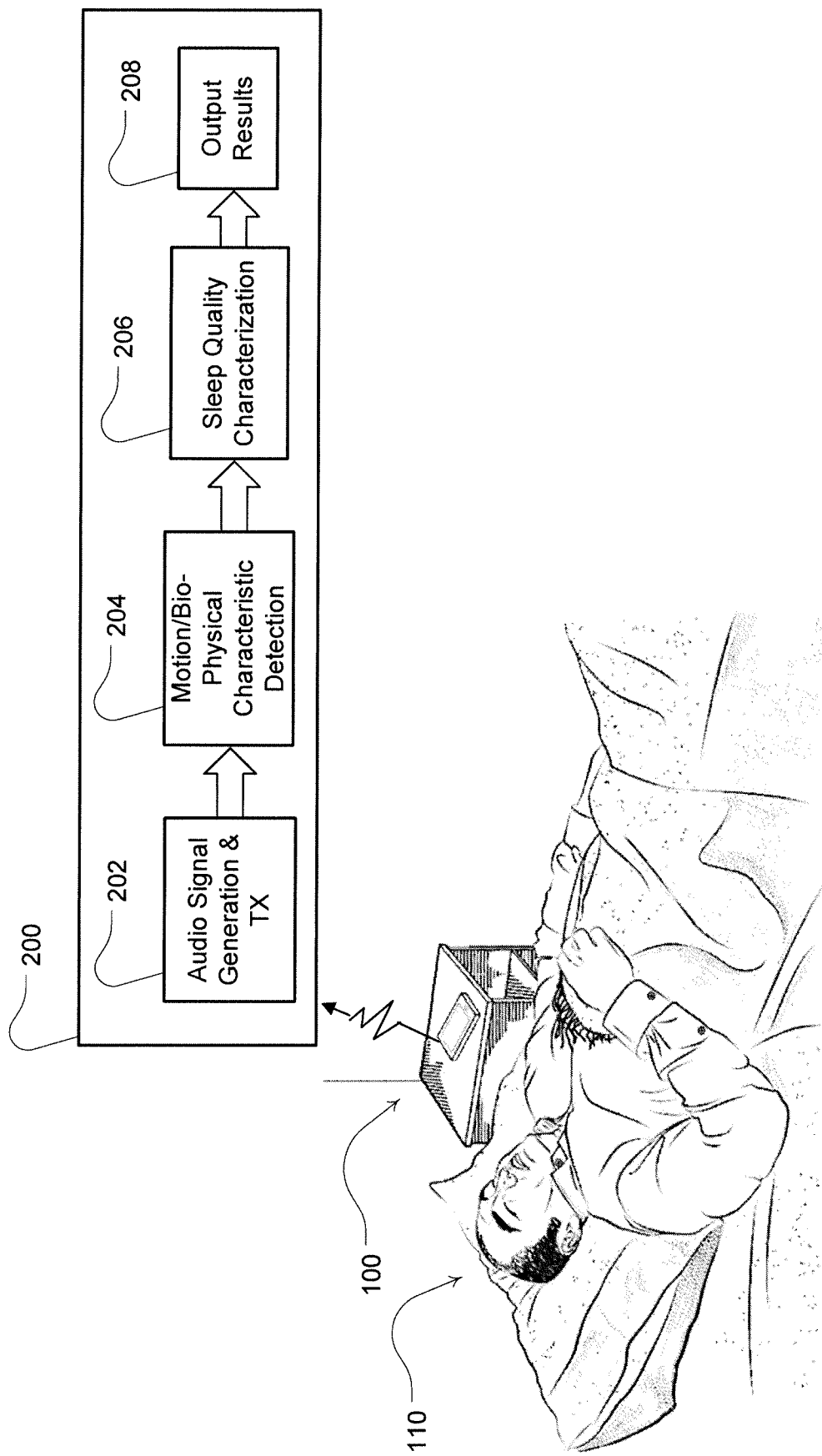
FIG. 2 is a schematic illustration of a system in accordance with an example of the present technology.

An example system suitable for implementing the present technology is now described with reference to FIGS. 1 to 3, as best shown in FIG. 2. A mobile device 100, or mobile electronic device, configured with an application 200 for detecting movement of subject 110, may be placed on a bedside table near subject 110. Mobile device 100 may be, for example, a smartphone or tablet having one or more processors. The processor(s) may be configured to, among other things, execute the functions of application 200, including causing an audio signal to be generated and transmitted, typically through the air as a generally open or unrestricted medium such as in a room vicinity of the device, receiving a reflection of the transmitted signal by sensing it with, for example, a transducer such as a microphone, and processing the sensed signal to determine body movement and respiration parameters. Mobile device 100 may comprise, among other components, a speaker and a microphone. The speaker may be used to transmit the generated audio signal and the microphone to receive the reflected signal. Optionally, the sound-based sensing methodologies of mobile device may be implemented in or by other types of devices such as a bedside device (e.g., a respiratory therapy device such as a continuous positive airway pressure (e.g., "CPAP") device or high flow therapy device). Examples of such devices, including a pressure device or blower (e.g., a motor and impeller in a volute), one or more sensors and a central controller of the pressure device or blower, may be considered in reference to the devices described in International Patent Publication No. WO/2015/061848 (Appl. No. PCT/AU2014/050315) filed on Oct. 28, 2014, and International Patent Publication No. WO/2016/145483 (Appl. No. PCT/AU2016/050117) filed on Mar. 14, 2016, the entire disclosures of which are incorporated herein by reference.

Figure 2A:
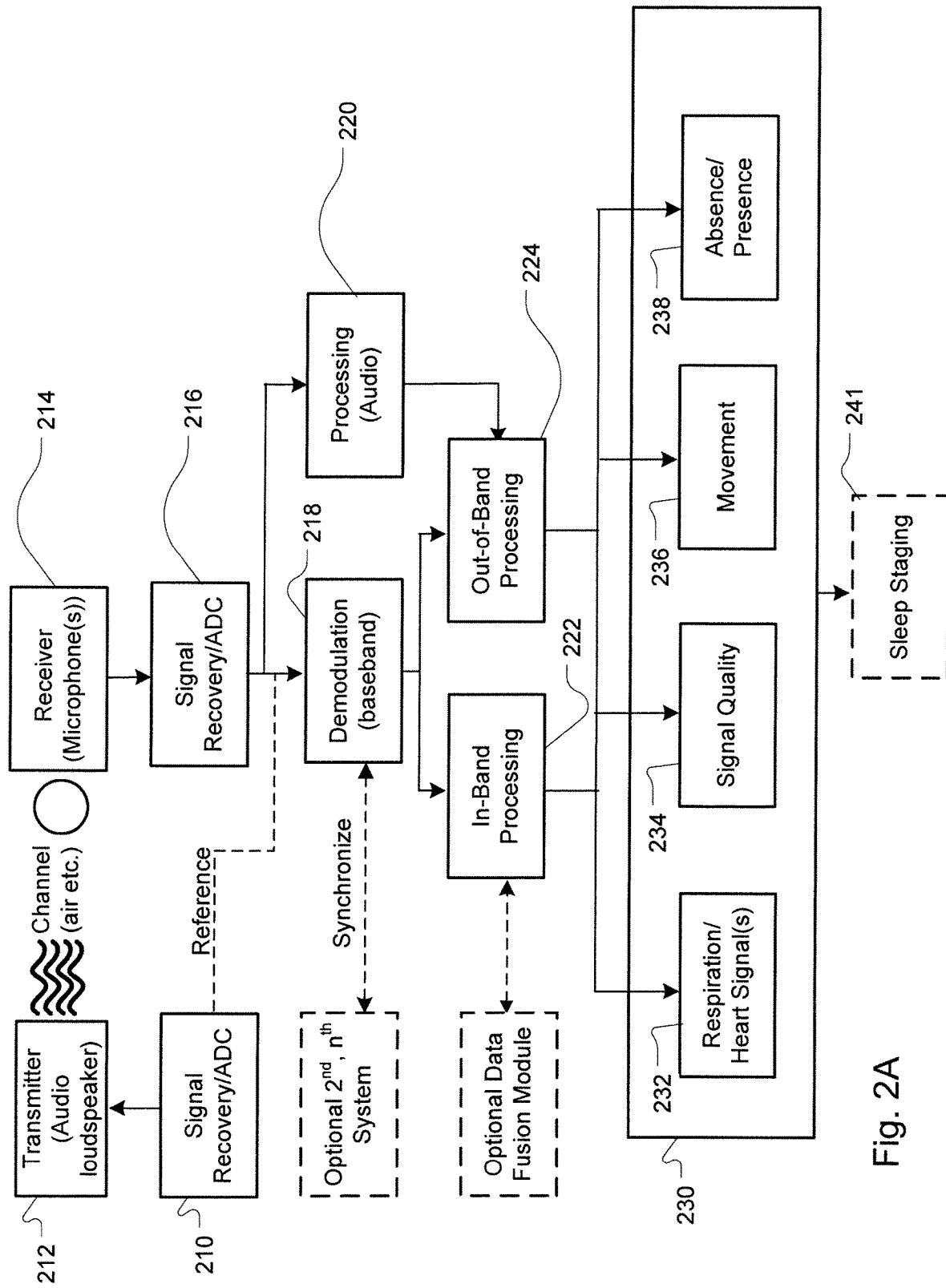
FIG. 2A illustrates a high level architectural block diagram of a system for implementing aspects of the present technology.

FIG. 2A illustrates a high level architectural block diagram of a system for implementing aspects of the present technology. This system may be implemented, for example, in mobile device 100. A signal generation component 210 may be configured to generate an audio signal for transmission towards a subject. As described herein, the signal may be audible or inaudible. For example, as discussed in more detail herein, the sound signal may, in some versions, be generated in a low frequency ultrasonic ranges, such about seventeen (17) kilohertz (KHz) to twenty-three (23) KHz, or in a range of about eighteen (18) KHz to twenty-two (2) KHz. Such frequency ranges are generally considered herein to be inaudible sound ranges. The generated signal may be transmitted via transmitter 212. In accordance with the disclosure, the transmitter 212 may be a mobile phone speaker. Once the generated signal has been transmitted, sound waves, including those waves reflected from the subject, may be sensed by receiver 214, which may be a mobile phone microphone.

As shown at 216, a signal recovery and analog-to-digital signal conversion stage may occur. The recovered signal may be demodulated to retrieve a signal representing a respiratory parameter, as shown at 218 such as in a demodulation processing module. The audio components of the signal may also be processed, as shown at 220, such as in an audio processing module. Such processing may include, for example, passive audio analysis to extract the sounds of breathing or other movement (including different types of activity such as rolling over in bed, PLM (periodic leg movement), RLS (restless leg syndrome) etc.) snoring, gasping, and wheezing. Audio component processing may also extract the sounds of interfering sources, such speech, TV, other media playback, and other ambient/environmental audio/noise sources. The output of demodulation phase at 218 may undergo both in-band processing at 222, such as by an in-band processing module, and out-of-band processing at 224 such as by an out-of-band processing module. For example, in-band processing at 222 may be directed to that portion of the signal band containing the respiratory and cardiac signal. Out-band processing at 224 may be directed to those portions of the signal containing other components, such as gross or fine movement (e.g., rollovers, kicks, gestures, moving around a room, etc.) The outputs of the in-band processing at 222 and out-band processing at 224 may then be provided to a signal post-processing at 230, such as in one or more signal post processing module(s). Signal post-processing at 230 may include, for example, respiration/heart signal processing at 232 such as in a respiration/heart signal processing module, signal quality processing at 234 such as in a signal quality processing module, gross body movement processing at 236 such as in a body movement processing module, and absence/presence processing at 238, such as in an absence/presence processing module.

While not shown in FIG. 2A, the outputs of signal post processing at 230 may undergo a second post-processing stage that provides sleep state, sleep scoring, fatigue indication, subject recognition, chronic disease monitoring and/or prediction, sleep disordered breathing event detection and other output parameters, such as from an evaluation of any of the motion characteristics of the produced motion signal (s). (e.g., respiratory related movement (or absence thereof), cardiac related movement, arousal-related movements, periodic leg movement, etc.). In the example of FIG. 2A, an optional sleep staging processing at 241, such as in a sleep staging processing module, is shown. However, any one or more of such processing modules/blocks may optionally be added (e.g., sleep scoring or staging, fatigue indication processing, subject recognition processing, chronic disease monitoring and/or prediction processing, sleep disordered breathing event detection processing, or other output processing, etc.). In some cases, the functions of signal post-processing at 230 or the second post-processing stage may be performed using any of the components, devices and/or methodologies of the apparatus, system and method described in any of the following patents or patent applications, wherein the entire disclosures of each is incorporated by reference herein: International Patent Application No. PCT/US2007/070196, filed Jun. 1, 2007 and entitled "Apparatus, System, and Method for Monitoring Physiological Signs;" International Patent Application No. PCT/US2007/083155, filed Oct. 31, 2007, entitled "System and Method for Monitoring Cardio-Respiratory Parameters;" International Patent Application No. PCT/US2009/058020, filed Sep. 23, 2009, entitled "Contactless and Minimal-Contact Monitoring of Quality of Life Parameters for Assessment and Intervention;" International Application No. PCT/US2010/023177, filed Feb. 4, 2010, entitled "Apparatus, System, and Method for Chronic Disease Monitoring;" International Patent Application No. PCT/AU2013/000564, filed Mar. 30, 2013, entitled "Method and Apparatus for Monitoring Cardio-Pulmonary Health;" International Patent Application No. PCT/AU2015/050273, filed May 25, 2015, entitled "Methods and Apparatus for Monitoring Chronic Disease;" International Patent Application No. PCT/AU2014/059311, filed Oct. 6, 2014, entitled "Fatigue Monitoring and Management System;" International Patent Application No. PCT/AU2013/060652, filed Sep. 19, 2013, entitled "System and Method for Determining Sleep Stage;" International Patent Application No. PCT/EP2016/058789, filed Apr. 20, 2016, entitled "Detection and Identification of a Human from Characteristic Signals;" International Patent Application No. PCT/EP2016/069496, filed 17 Aug. 2016, entitled "Screener for Sleep Disordered Breathing;" International Patent Application No. PCT/EP2016/069413, filed Aug. 16, 2016, entitled "Digital Range Gated Radio Frequency Sensor;" International Patent Application No. PCT/EP2016/070169, filed Aug. 26, 2016, entitled "Systems and Methods for Monitoring and Management of Chronic Disease;" and U.S. patent application Ser. No. 15/079,339, filed Mar. 24, 2016, entitled "Detection of Periodic Breathing." Thus, in some examples, the processing of detected movement, including for example, the breathing movement, may serve as a basis for determining any one or more of (a) a sleep state indicating sleep; (b) a sleep state indicating awake; (c) a sleep stage indicating deep sleep; (d) a sleep stage indicating light sleep; and (e) a sleep stage indicating REM sleep. In this regard, while the sound related sensing technologies of the present disclosure provide for different mechanisms/processes for motion sensing such as using a speaker and microphone and processing of the sound signals, when compared to radar or RF sensing technologies as described in these incorporated references, once a breathing signal, such as breathing rate is obtained with the sound sensing/processing methodologies described in this specification) the principles of processing breathing or other motion signal for an extraction of sleep states/stages information may be implemented by the determination methodologies of these incorporated references.

5.1.1 Mobile Device 100

Mobile device 100 may be adapted to provide an efficient and effective method of monitoring a subject's breathing and/or other movement related characteristics. When used during sleep, the mobile device 100 and its associated methods can be used to detect the user's breathing and identify sleep stages, sleep states, transitions between states, sleep-disordered breathing and/or other respiratory conditions. When used during wake, the mobile device 100 and its associated methods can be used to detect movement such as of a subject breathing (inspiration, expiration, pause, and derived rate) and/or ballistocardiogram waveform and subsequent derived heart rate. Such parameters may be used for controlling a game (whereby a user is guided to reduce their respiration rate for relaxation purposes), or evaluating respiratory condition such as of a subject with a chronic disease such as COPD, asthma, congestive heart failure (CHF) etc., where the subject's baseline respiratory parameter(s) change in the time before an exacerbation/decompensation event occurs. The respiratory waveform may also be processed to detect temporary cessation of breathing (such as central apnea, or the small chest movements against an obstructive airway seen during an obstructive apnea) or reduction in breathing (shallow breathing and/or reduction in breathing rate, such as related to a hypopnea).

Mobile device 100 may include integrated chips, a memory and/or other control instruction, data or information storage medium. For example, programmed instructions encompassing the assessment/signal processing methodologies described herein may be coded on integrated chips in the memory of the device or apparatus to form an application specific integrated chip (ASIC). Such instructions may also or alternatively be loaded as software or firmware using an appropriate data storage medium. Optionally, such processing instructions may be downloaded such as from a server over a network (e.g. an internet) to the mobile device such that when the instructions are executed, the processing device serves as a screening or monitoring device.

Figure 3:
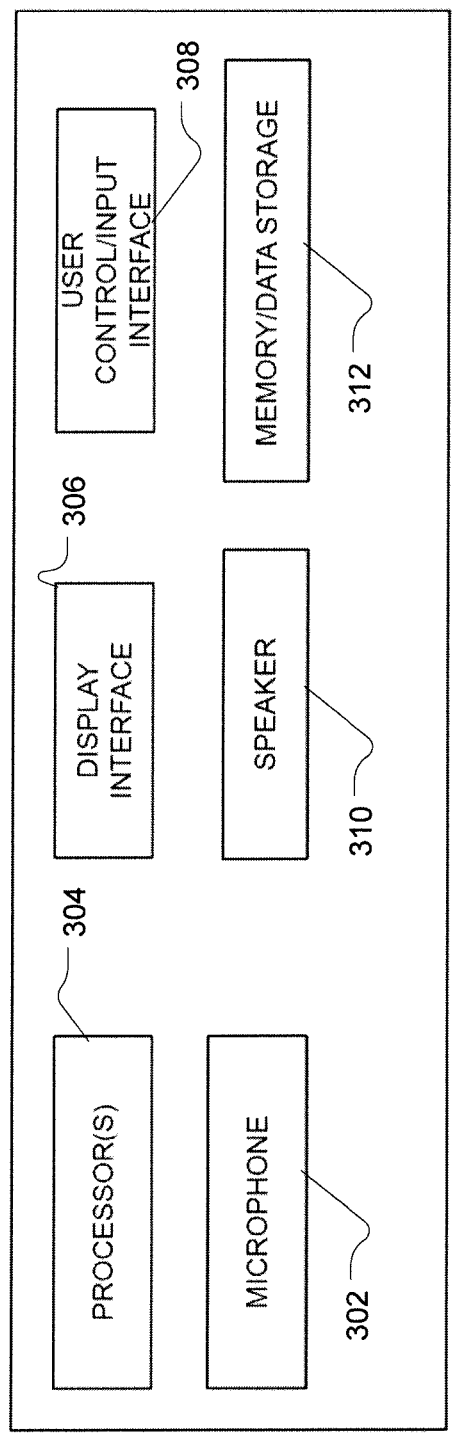
FIG. 3 is conceptual diagram of a mobile device configured in accordance with some forms of the present technology.

Accordingly, mobile device 100 may include a number of components as illustrated by FIG. 3. The mobile device 100 may include, among other components, a microphone or sound sensor 302, a processor 304, a display interface 306, a user control/input interface 308, a speaker 310, and a memory/data storage 312, such as with the processing instructions of the processing methodologies/modules described herein.

One or more of the components of mobile device 100 may be integral with or operably coupled with mobile device 100. For example, microphone or sound sensor 302 may be integral with mobile device 100 or coupled with mobile device 100 such as through a wired or wireless link (e.g., Bluetooth, Wi-Fi etc.).

Memory/data storage 312 may comprise a plurality of processor control instructions for controlling processors 304. For example, memory/data storage 312 may comprise processor control instructions for causing application 200 to be performed by the processing instructions of the processing methodologies/modules described herein.

5.1.2 Motion and Breathing Detection Process

Examples of the present technology may be configured to use one or more algorithms or processes, which may be embodied by application 200, to detect motion, breathing, and optionally sleep characteristics while a user is asleep using the mobile device 100. For example, application 200 may be characterized by several sub-processes or modules. As shown in FIG. 2, application 200 may include an audio signal generation and transmission sub-process 202, a motion and bio-physical characteristic detection sub-process 204, a sleep quality characterization sub-process 206, and a results output sub-process 208.

5.1.2.1 Generating and Transmitting an Audio Signal

According to some aspects of the present technology, an audio signal may be generated and transmitted towards a user such as using one or more tones described herein. A tone provides pressure variation in a medium (e.g., air) at a particular frequency. For purposes of this description, the generated tones (or audio signals or sound signals) may be referred to as "sound", "acoustic" or "audio" because they may be generated in a like manner to audible pressure waves (e.g., by a speaker). However, such pressure variations and tone(s) should be understood herein to be either audible or inaudible, notwithstanding their characterization by any of the terms "sound", "acoustic" or "audio." Thus, the audio signal generated may be audible or inaudible, wherein the frequency threshold of audibility across the human population varies by age. The typical "audio frequency" standard range is around 20 Hz to 20,000 Hz (20 kHz). The threshold of higher frequency hearing tends to reduce with age, with middle aged people often unable to hear sounds with frequencies above 15-17 kHz, whereas a teenager may be able to hear 18 kHz. The most important frequencies for speech are approximately in the range 250-6,000 Hz. Speaker and microphone signal responses for typical consumer smartphones are designed to roll off above 19-20 kHz in many cases, with some extending to above 23 kHz and higher (especially where the device supports a sampling rate of greater than 48 kHz such as 96 kHz). Therefore, for most people, it is possible to use signals in the range of 17/18 to 24 kHz and remain inaudible. For younger people that can hear 18 kHz but not 19 kHz, a band of 19 kHz to say 21 kHz could be employed. It is noted that some household pets may be able to hear higher frequencies (e.g., dogs up to 60 kHz and cats up to 79 kHz).

The audio signal may comprise, for example, sinusoidal waveforms, sawtooth chirps, triangular chirps, etc. As background, the term "chirp", as used herein, is a short-term non-stationary signal that could, for example, have a sawtooth or triangular shape, with a linear or non-linear profile. Several types of signal processing methods may be used to produce and sense the audio signal including, for example, continuous wave (CW) homodyning, pulsed CW homodyning, frequency modulated CW (FMCW), frequency hopping range gating (FHRG), adaptive FHRG (AFHRG), ultra wideband (UWB), orthogonal frequency division multiplexing (OFDM), adaptive CW, frequency shift keying (FSK), phase shift keying (PSK), binary phase shift keying (BSPK), quadrature phase shift keying (QPSK), and the generalized QPSK called quadrature amplitude modulation (QAM) etc.

According to some aspects of the present technology, a calibration function, or calibration module, may be provided for assessing the characteristics of the mobile device. If a calibration function suggests that the hardware, environment, or user set up requires an audible frequency, coding may be overlaid on a spread spectrum signal that is acceptable to the user while still allowing active detection of any biomotion signals in the sensing area. For example, it is possible to "hide" an audible or inaudible sensing signal in an audible sound such as a music, TV, streaming source or other signal (e.g., a pleasing, repetitive sound that may optionally be synchronized to the detected breathing signal such as waves crashing on the shore that might be used to aid sleep). This is similar to audio steganography, where messages that must be perceptually indiscernible are hidden in the audio signal, using techniques such as phase coding where elements of the phase are adjusted to represent the encoded data.

5.1.2.2 Motion and Bio-Physical Signal Processing
5.1.2.2.1 Technical Challenges To achieve good motion signal to environmental related noise ratios, several room acoustic issues should be considered. Such issues may include, for example, reverberation, bed clothes usage, and/or other room acoustic issues. In addition, specific monitoring device characteristics, such as directionality of the mobile device or other monitoring device, should also be considered.

5.1.2.2.1.1 Reverberation

A reverberation may be created when sound energy is confined to a space with reflective walls, such as a room. Typically, when a sound is first generated, the listener first hears the direct sound from the source itself. Later, the user may hear discrete echoes caused by sound bouncing off room walls, the ceiling, and the floor. Over time, individual reflections may become indistinguishable and the listener hears continuous reverberation that decays over time.

Wall reflections typically absorb very little energy at the frequencies of interest. Accordingly, sound is attenuated by the air, and not by the walls. Typical attenuation may be <1%. It takes approximately 400 ms in a typical room at audio frequencies for a sound attenuation of 60 dB to be reached. Attenuation increases with frequency. For example, at 18 kHz, the typical room reverberation time is reduced to 250 ms.

Several side effects are associated with reverberation. For example, reverberation results in room modes. Because of the reverberation energy storage mechanism, the input of acoustic energy to the room causes standing waves at resonant or preferred modal frequencies ($n\lambda=L$). For an ideal three-dimensional room, of dimensions Lx, Ly and Lz, the main modes are given by $$f_{p,q,r} = \frac{c_0}{2}\sqrt{\left(\frac{p}{L_x}\right)^2 + \left(\frac{q}{L_y}\right)^2 + \left(\frac{r}{L_z}\right)^2}$$

These standing waves result in the loudness of the particular resonant frequency being different at different locations of the room. This may result in signal level variation and associated fading at the sensing component (e.g., sound sensor) that receives the sound signal. This is analogous to multipath interference/fading of electromagnetic waves (e.g., RF) such as Wi-Fi; however, room reverberation and associated artifacts such as fading are more severe for audio.

Room modes may present design issues for sonar systems. Such issues may include, for example, fading, 1/f noise, and gross motion signals. A gross motion usually refers to a large physiological movement such as a rollover in bed (or a user getting in or out of bed, which is associated with an absence before or after the event respectively). In one realization, a movement can be considered as a binary vector (movement or no movement), with an associated activity index referring to the duration and intensity of movement (e.g., PLM, RLS or bruxism is an example of a movement activity that is not a gross motion, as it relates to limb(s) or grinding of the jaw, and not movement the full body when changing position in bed). The signal received by sound sensor 302 (e.g., microphone) may experience fading of the signal strength and/or fading of the reflected signal from the user. This fading may be caused by standing waves due to reverberation and may result in a signal amplitude variation issue. 1/f noise (a signal with a power spectral density that is inversely proportional to the frequency of the signal) at breathing frequencies may occur due to room air currents disturbing the room modes and resulting in a noise floor increase and hence a signal to noise reduction at breathing frequencies. Gross motion signals from any movement in a room are due to the disturbance of the room mode energy and may produce a resultant sensed/received signal strength and phase variation. However, while this is an issue, it can be seen that by deliberately setting up room modes, a useful gross (large) motion and more subtle activity detection can be performed, and indeed respiration analysis for the case of one dominant motion source in the room (e.g., a single person in a bedroom).

The term SONAR is used herein to include sound signals, acoustic, sonic, ultrasonic, and low frequency ultrasonic, for ranging and movement detection. Such signals could range from DC to 50 kHz or above. Some of the processing techniques such as the FMCW physiological signal extraction may also be applicable to actual short range (e.g., up to approximately 3 meters-such as for monitoring a living space or bedroom) RF (electromagnetic) radar sensors, such as those operating at 5.8 GHz, 10.5 GHz, 24 GHz etc.

5.1.2.2.1.2 Bed Clothes

The use of bed clothes (e.g., duvets, comforters, blankets, etc.) may severely attenuate sound in a room. In some aspects, a duvet may attenuate a sound signal twice at it travels and returns from a sleeping person. A duvet surface also reflects the sound signal. If the breathing is seen at the duvet surface, then a duvet reflection signal can be used for monitoring breathing.

5.1.2.2.1.3 Phone Characteristics

The placement of the speaker and microphone on a smartphone are not always optimal for acoustic sensing in a sonar-like application. The typical smartphone speaker to microphone has poor directionality. Generally, smartphone audio is designed for human speech, and not specifically designed for sonar-like acoustic sensing applications. Moreover, placement of speakers and microphones vary among smartphone models. For example, some smartphones have the speaker at the back of the phone and the microphone on the side of the phone. As a result, the microphone cannot easily "see" the speaker signal without first being redirected by reflections. Additionally, the directionality of both speaker and microphone increase with frequency.

Room modes may enhance the omnidirectional nature of a smartphone microphone and speaker. Reverberation and associated room modes produce standing waves nodes throughout the room at the particular frequencies. Any movement in the room can be seen at these nodes as the movement disturbs all room mode nodes. A smartphone microphone, when located at a node or antinode, acquires an omnidirectional characteristic due to the sound path being omnidirectional even though the microphone and speaker are directional.

5.1.2.2.2 Overcoming the Technical Challenges

According to aspects of the disclosure, specific modulation and demodulation techniques may be applied to reduce or remove the impact of the identified and other technical challenges.

5.1.2.2.2.1 Frequency Hopping Range Gating (FHRG) and Adaptive Frequency Hopping Range Gating (AFHRG)

A frequency hopping range gated signal is a modulation demodulation technique that utilizes a sequence of discrete tones/frequencies which occupy a specified frequency range. Each tone, tone pair, or multi tone pulse in the tone sequence is transmitted for a particular duration, defined by the range requirement. A change to the particular duration of such a tone pulse or tone pair results in a change of the detection range. A sequence of tone pairs or tones produces a tone frame or a frame of slots. Each slot may be considered a tone slot. Thus, a frame may include a plurality of slots, where each slot may contain a tone or tone pair. Typically, to promote improved inaudibility, each tone pair may have a time duration that is equal to the time duration of a slot of the frame. However, this is not required. In some cases, the slots of a frame may be of equal or unequal width (time duration). Thus, the tone pairs of a frame may be of equal or unequal duration within the frame. The sound modulation can contain guard bands (quiet periods) between tones, and then between frames, in order to allow better separation of sensed/received tones such that range gating can be achieved. FHRG can be used in audio frequencies that are usable. FHRG can apply frequency hopping with frequency dithering, and/or timing dithering. Timing dithering means that frame and/or internal slot timing can vary (e.g., time period of the slot varies, or the start time of the frame or the start time of the slot in a time series may vary), such as to reduce the risk of room modes building up, and also to reduce the risk of interference between other SONAR sensing in the environment. For example, in the case of a four-slot frame, while frame width may remain constant, time dithering can permit at least one smaller slot width (e.g. a tone pair of shorter duration) and at least one larger slot width (e.g., a tone pair of longer duration) in the frame while the other slot widths may be unchanged). This can provide a slight variation in the particular range detected by each slot of the frame. Frequency dithering can allow for multiple "sensors" (e.g., two or more sensing systems in a room) to coexist in a common vicinity. For example, by employing frequency dithering, the frequency of a slot (tone or tone pair) is moving such that there is a statistically insignificant chance that interference occurs between the "sensors" in normal operation. Both time and frequency dithering can reduce the risk of interference from non-SONAR sources in the room/environment. Synchronization demodulation requires precise understanding of alignment between sequences, e.g., by using special training sequences/pulses and then pattern detection/matched filters to align the frames and recover the actual offset.

Figure 4:
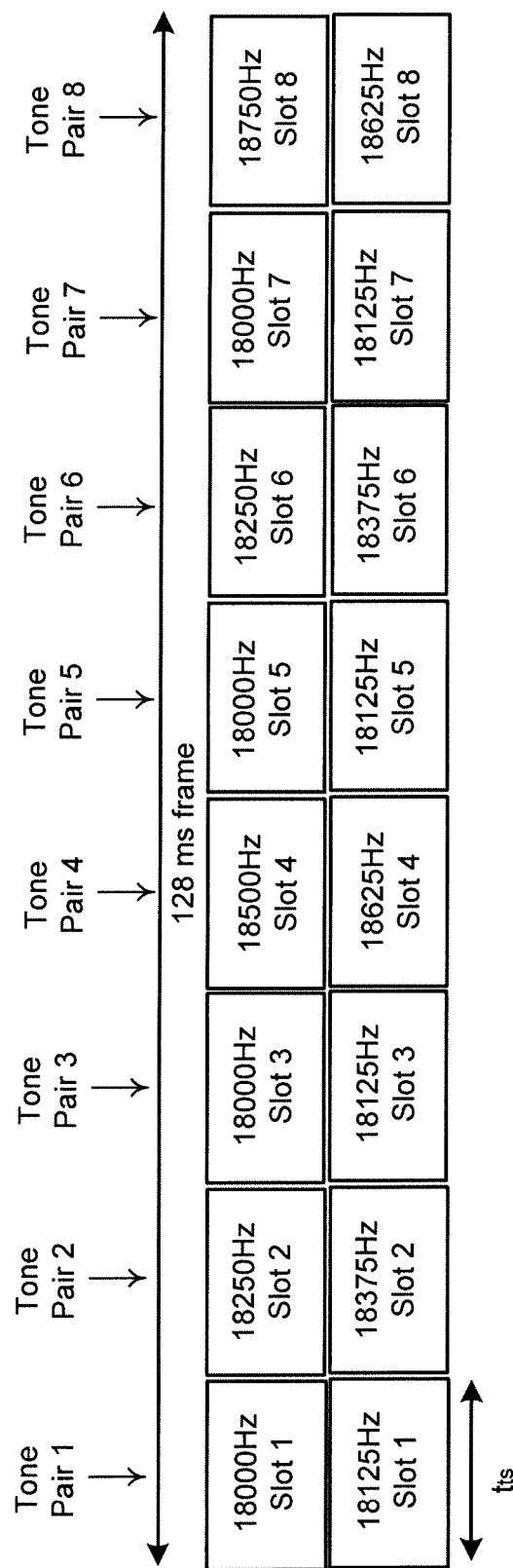
FIG. 4 illustrates an example FHRG sonar frame.

FIG. 4 illustrates an example FHRG sonar frame. As shown, 8 individual pulsed sonar (analogous to a radar system) signals may be transmitted in each frame. Each pulse may contain 2 orthogonal pulse frequencies, and each pulse may be 16 ms long. As a result, 16 separate frequencies may be transmitted in each 128 ms transceiver frame. The block (frame) then repeats. It may exploit orthogonal frequencies of OFDM to optimize the frequency use in a confined bandwidth and enhance signal-to-noise. The orthogonal Dirac Comb frequencies also allow for frame timing dithering and tone frequency dithering to assist noise reduction. The tone pair shapes the resulting pulse, and this shaping aids inaudibility.

Figure 5:
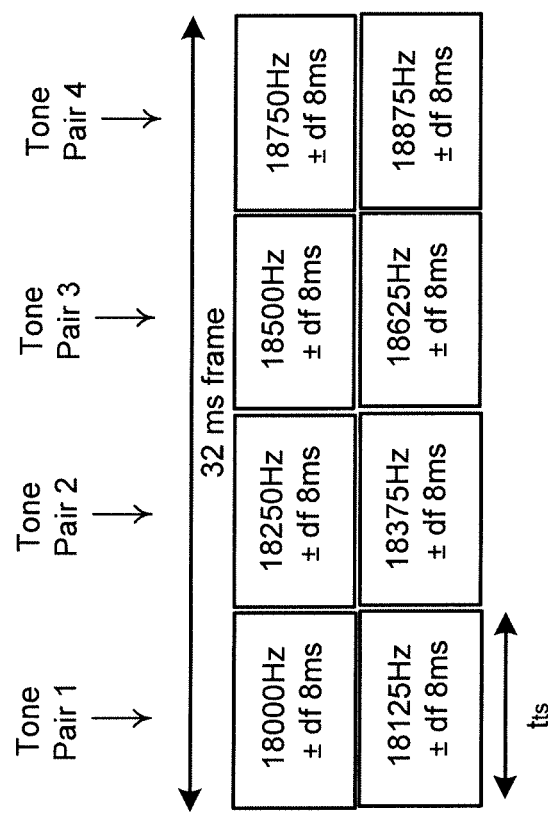
FIG. 5 illustrates an example of an AFHRG transceiver frame.

An adaptive frequency hopping range gating (AFHRG) system keeps changing frequency of the tone frequency sequence over time, using tones of a defined length (e.g., 16 or 8 ms) before switching to another tone (for a total of four tones). Thus, a block of tones is generated, and the block (frame) then repeats at 31.25 Hz. For an AFHRG system, the tone patterns shift on each frame. These patterns can shift constantly. Thus, a frame can have a pattern of frequencies that differs from a pattern of frequencies of other frames of a series of frames. Thus, the pattern of different frequencies may change. A frame can also have different frequencies within the frame, such as within a slot, or differences with respect to different slots. In addition, each frame may adapt, by adjusting its frequency inside a fixed band, to mitigate fading. FIG. 5 illustrates an example of a single 32 ms transceiver frame for an AFHRG system. As shown in FIG. 5, four individual homodyne pulsed sonar signals may be transmitted in each frame. Each signal has an 8 ms time of flight. At 8 ms time of flight, the range, including both directions, is 2.7 meters giving an effective actual frame of 1.35 m, and a pulse repetition frequency of 31.25 Hz. Additionally, each pulse may include two pulse frequencies (e.g., essentially simultaneous tones), as shown in FIG. 5, resulting in 8 separate pulsed homodyne signals in a single 32 ms transceiver frame.

AFHRG may be configured to use Dirac Comb frequencies and orthogonal pulse pairs to optimize available bandwidth. Each "pair" can be in a slot within a frame. Thus, multiple frames can contain many "pairs" in repeating or non-repeating patterns. Separate frequency pairs may be used for each timeslot, and may use linear or Costas Code frequency hopping. The timeslot may be determined based on the desired range detection. For example, as shown in FIG. 5, $t_{ts}$=8 ms for a 1.3 m detection range. Frequency pairs may be generated as: {A Sin($\omega_1$t)–A Sin($\omega_2$t)} with $$\omega_1 - \omega_2 = \frac{2\pi}{tts}.$$

Each frame may adapt, by adjusting its frequency inside a fixed band, to mitigate fading once the requirement of the frequency pairs equation is maintained. Thus, the adaption acts to maximize the available SNR (signal to noise ratio) from any subject(s) present in the detection range.

Each frequency pair may be chosen to optimize a desired bandwidth (e.g., the 1 kHz bandwidth (18 kHz to 19 kHz)), to provide maximum isolation between frequencies, to provide maximum isolation between pulses, and/or to minimize inter pulse transients. These optimizations may be achieved for n frequencies, each with a frequency separation df and a slot width of tts such that:

$$df = f_n - f_{n-1} = BW/n$$

and $$df = \frac{1}{tts}$$

For an 8 ms time slot duration and a 1 kHz bandwidth (say $f_n$=18,125 Hz and $f_{n-1}$=18,000 Hz), the frequency separation df becomes:

$$df = 125\ Hz = 1\ kHz/8$$

and $$df = \frac{1}{8\ ms}$$

Zero crossing is achieved by utilizing the trigonometric identity:

$$\sin a - \sin b = 2\sin\frac{1}{2}(a-b)\cos\frac{1}{2}(a+b),$$

such that each timeslot comprises a sinusoidal pulse amplitude with a frequency of $$f_n - \frac{1}{2}df.$$

Thus, the duration of a slot, or each slot, of a frame may be equal to one divided by the difference between the frequencies of the tone pairs. Thus, in a frame, a time slot duration may be inversely proportional to the frequency difference of the frequencies of the tones of a tone pair of the time slot.

Figure 6A:
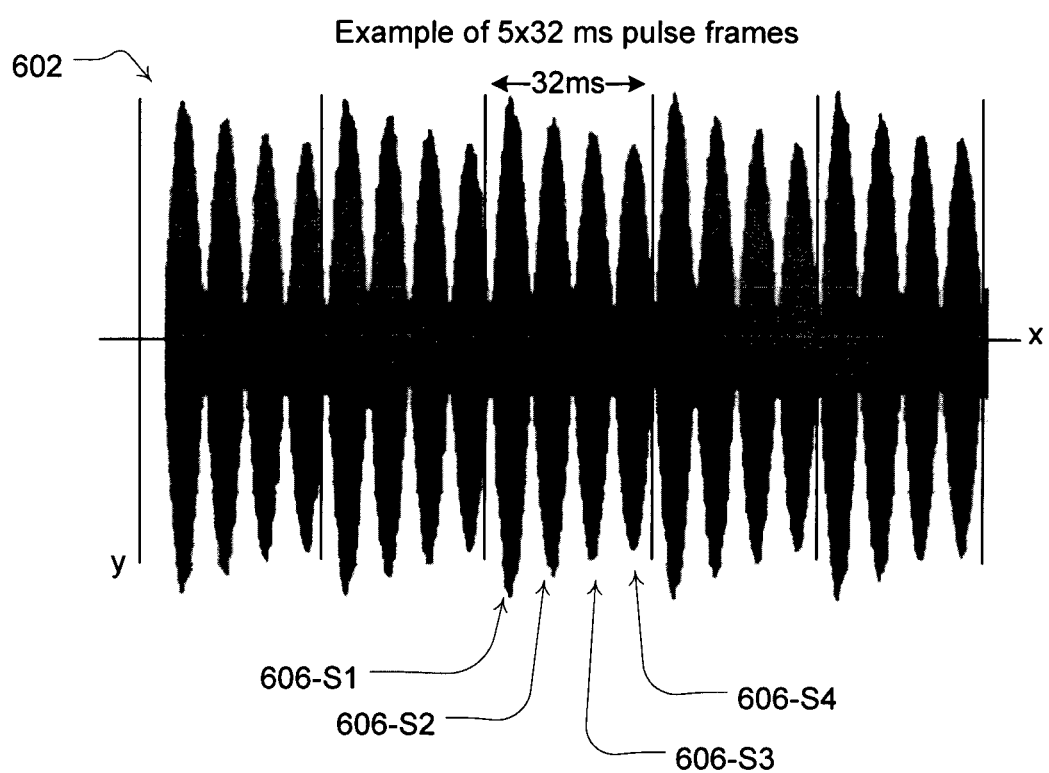
FIGS. 6A, 6B and 6C illustrate an example of pulsed AFHRG frames.
Figure 6B:
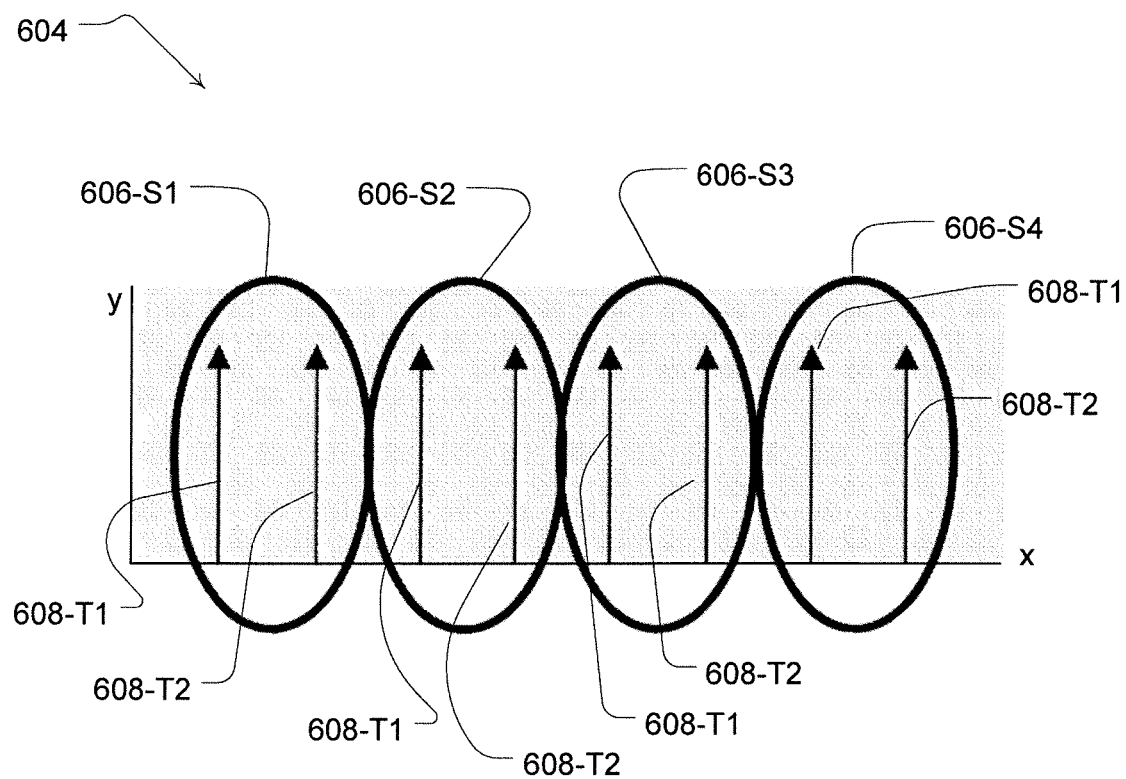
Figure 6C:
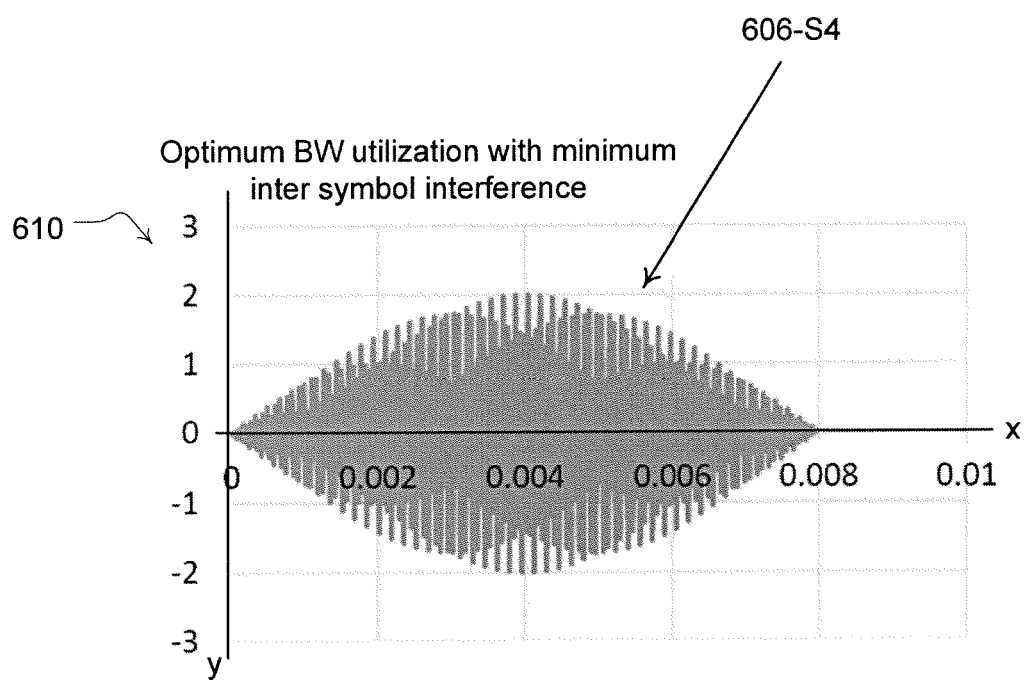

FIGS. 6A, 6B and 6C illustrate an example of 5×32 ms pulsed frames for an example AFHRG system. Graph 602 in FIG. 6A shows 5×32 ms pulse frames on an x-axis of time and a y-axis of amplitude. Graph 602 is a time domain representation of five 32 ms frames, of which each frame contains four (4) slots—for a total of 5×4=20 tone pairs. A tone pair is in each of slots 606-S1, 606-S2, 606-S3, 606-S4.

The envelope of this is varying, which exemplifies a "real world" speaker and mic combination that may be slightly less sensitive at higher frequencies. The slots that form a frame shown in FIG. 6A may be considered in more detail in the graph 604 of FIG. 6B. Graph 604 shows a frequency domain representation of a single 32 ms frame from FIG. 6A. It shows four slots 606-S1, 606-S2, 606-S3, 606-S4 where each slot contains two tones 608T1, 608T2 (a tone pair). Graph 604 has an x-axis of frequency, y-axis that is arbitrary. In an example, the tones of the tone pairs of the frame are each different sound tones (e.g., different frequencies) in a range of 18000 Hz to 18875 Hz. Other frequency ranges, such as for inaudible sound, may be implemented as discussed in more detail herein. Each tone pair of the tone pairs of the frame are generated sequentially (in series) in the frame. The tones of a tone pair are produced substantially simultaneously in a common slot of the frame. The tone pair of a slot of FIGS. 6A and 6B may be considered in reference to the graph 610 in FIG. 6C. Graph 610 is an illustration of a time domain view of a single tone pair (e.g., tones 608T1, 608T2) in a frame showing their concurrent generation in a slot of the frame. Graph 610 has an x-axis of time, y-axis of amplitude. In the example, the amplitude of the tones are ramped up and down within the time period of the time slot. In the example of the graph of 610, the tone amplitude ramp begins with the slot start time at zero amplitude and ramps down to end with the slot at zero amplitude. Such contemporaneous zero amplitude tone arrival at the beginning and end of the slot can improve inaudibility between tone pairs of adjacent slot(s) that have the same end and beginning slot amplitude characteristics.

Figure 7:
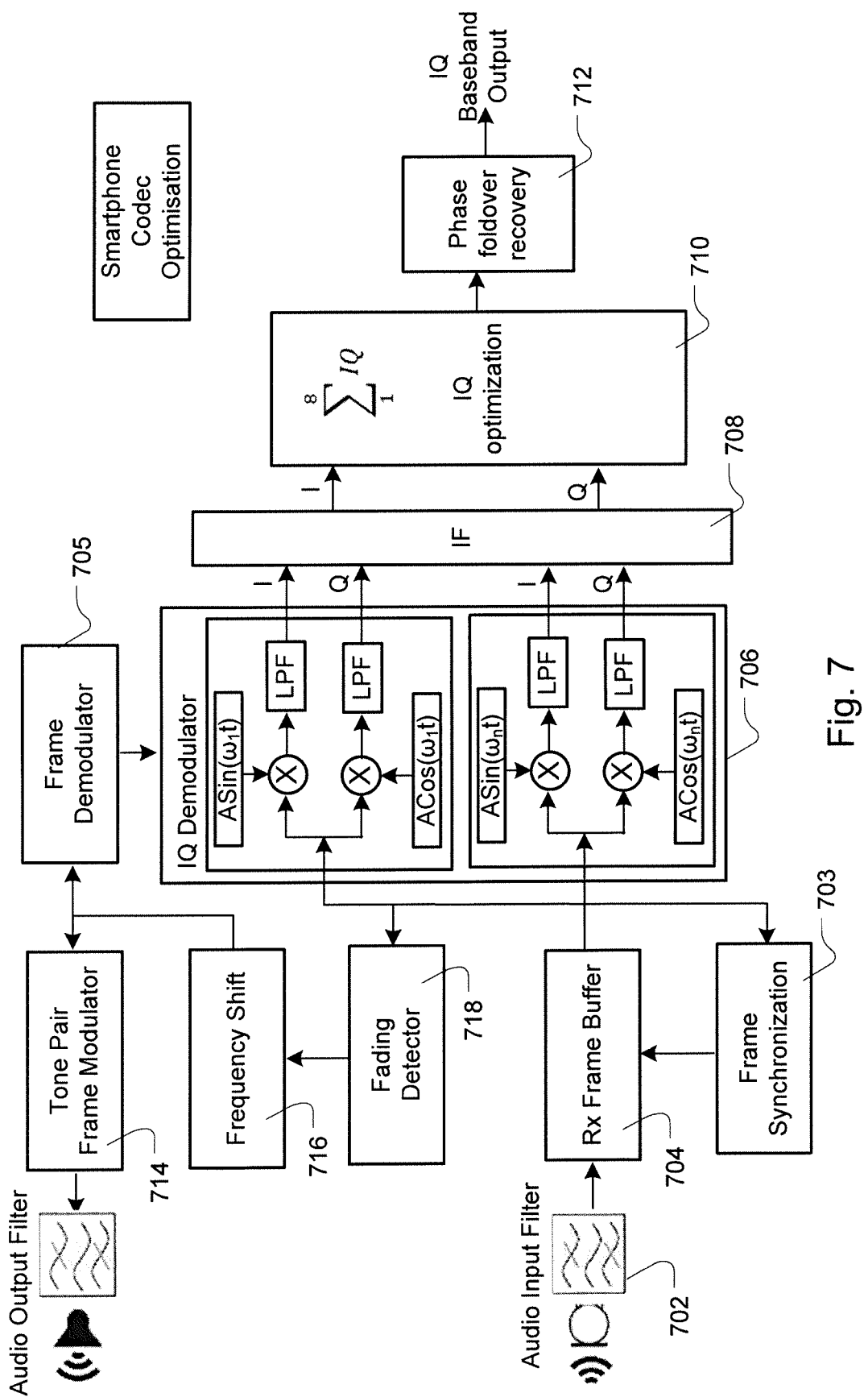
FIG. 7 is a conceptual diagram of an (A) FHRG architecture.

Aspects of an FHRG or an AFHRG (herein both being referred to as "(A)FHRG") architecture for processing audio signals will now be described in reference to the methodologies of the processing modules shown in FIG. 7. As shown in FIG. 7, reflected signals may be sensed, filtered via a module of high pass filter 702, and input to Rx frame buffer 704. The buffered Rx frames may be processed by IQ (in-phase and quadrature) demodulator 706. According to some aspects of the disclosure, each of n (where n may be, for example, 4, 8 or 16) frequencies may be demodulated to baseband as I and Q components, where the baseband represents motion information (breathing/bodily movement, etc.) corresponding to changes in sensed distance that is detected with the audio reflections (e.g., transmitted/produced and received/sensed audio signals or tone pairs). An intermediate frequency (IF) stage 708 is a processing module that outputs a single I and Q component from multiple signals, which undergoes optimization in a module "IQ Optimization" at 710 to produce a single combined output.

The multi IQ input information at 710 can be optimized and condensed to a single IQ baseband signal output for the algorithm input stage. The single IQ output (effectively a combined signal from I and Q components) can be derived based on a selection of a candidate IQ pair based on the one with the highest signal quality, such as based on the clearest breathing rate. For example, breathing rates may be detected from the baseband signal (a candidate signal or combined signal) as described in International Application WO2015006364, the entire disclosure of which is incorporated herein by reference. The single IQ output can also be an average of the input signals, or indeed an average or median of the derived breathings rates. Thus, such a module at 710 may include a summing and/or averaging process.

An AFHRG architecture allows for the optional addition of an IF stage. There are two possible IF stage methodologies—(i) comparing early, for example, 4 ms (0.5 m range)

with later, for example, 4 ms (0.5 m range) signal, and (ii) comparing the phase of a first tone with phase of a second tone in a tone pair. Because the stage compares the level or phase change in the sensed sound signal within the time of flight (ToF) time, it can act to remove common mode signal artefacts such as motion and 1/f noise issues. A phase foldover recovery module 712 receives the I and Q component output of optimization stage at 710 and, after processing, outputs an IQ baseband output. It can be desirable to minimize foldover in the demodulated signal, as this significantly complicates respiratory "in band" detection. Foldovers can be minimized using I/Q combination techniques, such as arctangent demodulation, using real-time center tracking estimation, or more standard dimensionality reduction methods, such as principal components analysis. Foldover occurs if movement of the chest spans over a half wavelength of approximately ~9 mm (such as for a CW frequency of 18 kHz at a temperature of 20 deg C, the speed of sound is approx. 343 m/s and the wavelength is approx. 19 mm). A dynamic center frequency strategy can be used to automatically correct for foldover—e.g., to reduce the severity or probability of occurrence of this behavior. In this case, if frequency doubling, or an unusually jagged respiratory pattern (morphology) is detected, the system can move the center frequency to a new frequency to push the I/Q channels back into balance and out of a foldover situation. Reprocessing is typically required whenever the person moves. The change in audio frequency is designed so as not to be audible (unless a masking tone is in use). If movement is at lambda/4, we may see it on one channel. If movement is greater than lambda/2, then we are very likely to see it on both channels.

In an FHRG implementation, the frames/tone pair frame modulator at 714 are controlled by the processor (with implicit multi frequency operation using frames etc.). In an adaptive implementation such as AFHRG or AToF, the system further includes modules for fading detection and explicit frequency shift operations not present in an FHRG implementation. The module of fading detector 718 provides a feedback mechanism to adjust the parameters of the system (including frequency shift, modulation type, frame parameters such as number of tones, spacing in time and frequency etc.) to optimally detect motion including respiration, in varying channel conditions. Fading can be directly detected from the amplitude modulation (extracted via envelope detection) variation in the sensed sound signal, and/or via changes in specific tone pairs. The fading detector may also receive secondary information from subsequent baseband signal processing, although this may add some processing delay; this can be used to relate actual extracted breathing signal quality/morphology to the current channel conditions, to provide better adaption to maximize useful signal. The fading detector may also process I/Q pairs (pre baseband respiration/heart rate analysis). By using a configuration of non-faded Tx (transmit) waveform(s), the finite emitted signal power of the speaker can also be optimized/best utilized to maximize the useful information received by the sound sensor/receiver Rx (receive), and demodulated/further processed to baseband. In some cases, the system may select a slightly suboptimal (in terms of short term SNR) set of frequencies for Tx, if the system is found to be more stable over a longer period of time (e.g., to avoid multipath variation in fading on a timescale similar to a respiration rate, that might cause "noise"/artefact in the desired demodulated respiration rate band).

Of course, if one or more individual tones are used in place of tone pairs, a similar architecture can be utilized to realize an adaptive CW (ACW) system.

Figure 8:
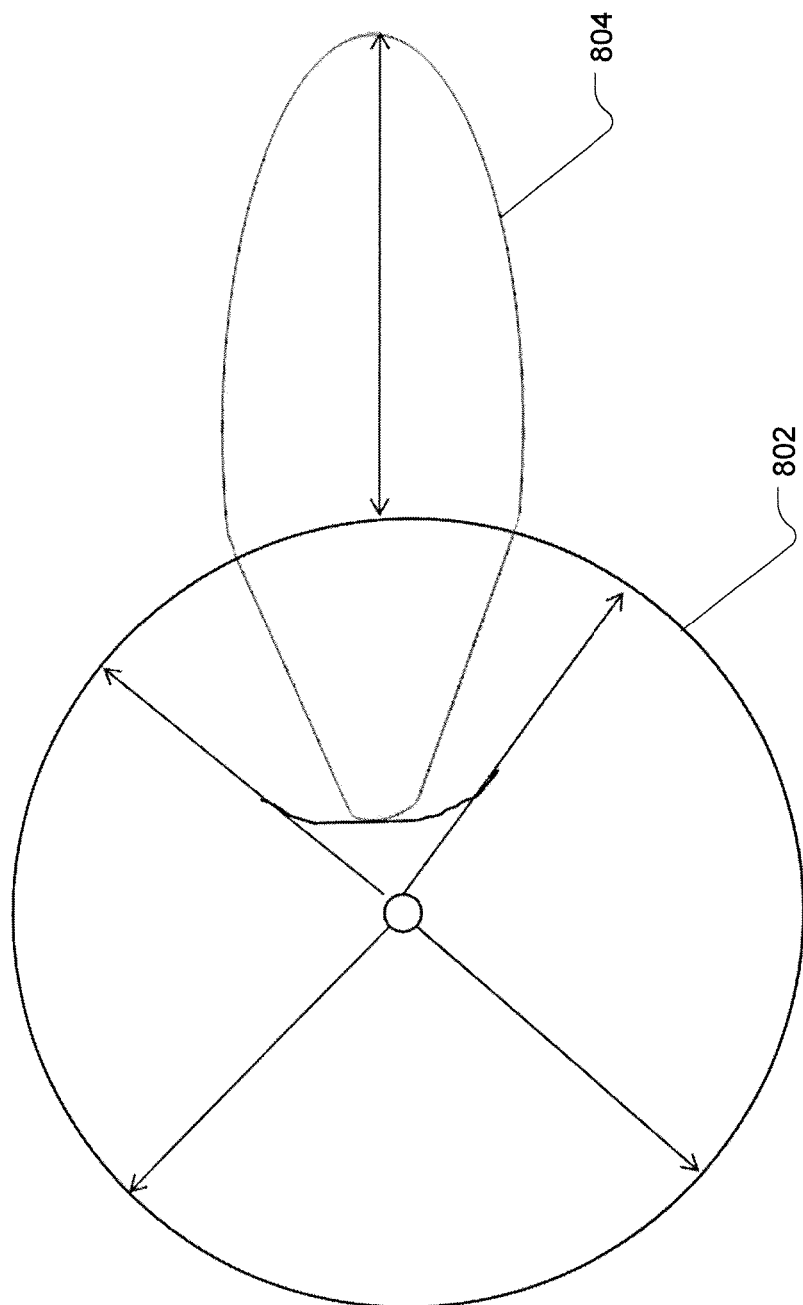
FIG. 8 illustrates an example of an isotropic omnidirectional antenna vs. a directional antenna.

5.1.2.2.2.2 FHRG Modulation Module and Demodulation Module Details 5.1.2.2.2.2.1 FHRG Sonar Equation The transmitted sound pressure signal generated by the smartphone speaker is reflected by a target, and returns to be sensed at the smartphone microphone. FIG. 8 illustrates an example of an isotropic omnidirectional antenna 802 vs. a directional antenna 804. For an omnidirectional source the sound pressure (P(x)) level will decrease with distance x as:

$$P(x) = \frac{P_0}{4\pi x^2}$$

The smartphone speaker is directional at 18 kHz hence:

$$P(x) = \frac{P_0}{4\pi x^\gamma}$$

where $\gamma$ is the speaker gain and has a value between 0 and 2, typically >1.

The target (e.g., a user in bed) has a specific cross section and reflection coefficient. Reflection from the target is also directional:

$$P(x) = \sigma(1-\alpha)\frac{P_0}{4\pi x^\beta}$$

where $\alpha$ is the reflector attenuation and has a value between 0 and 1, typically <0.1

$\beta$ is the reflector gain and has a value between 0 and 2, typically >1

$\sigma$ is the sonar cross-section.

As result, a transmitted signal of sound pressure $P_0$ will, on reflection at a distance d, return to the smartphone with an attenuated level of:

$$P_{rxs}(d) = \sigma(1-\alpha)\frac{P_0}{(4\pi)^2 d^{(\beta+\gamma)}}$$

The smartphone microphone will then see a portion of the reflected sound pressure signal. The percentage will be dependent on the microphone effective area $A_e$:

$$P_{rxm}(d) = A_e\sigma(1-\alpha)\frac{P_0}{(4\pi)^2 d^{(\beta+\gamma)}}$$

In this way a small fraction of the transmit sound pressure signal is reflected by a target and returns to be sensed at the smartphone microphone.

5.1.2.2.2.2.2 FHRG Movement Signal(s)

A person within range of an FHRG system at a distance d from the transceiver will reflect the active sonar transmit signal and produce a receive signal.

The sound (pressure wave) generated by the smartphone due to the modem signal for any frequency $f_{nm}$ is:

$$P_{rx}(x, t, w_{nm}) = \frac{P_0}{x^\gamma} \sin 2\pi\left(f_{nm}t + \frac{x}{\lambda_{nm}}\right)$$

The signal arriving at the target, at a distance d, for any individual frequency is given as:

$$P_{rx}(x, t, w_{nm}) = \frac{P_0}{x^\gamma} \sin 2\pi\left(f_{nm}t + \frac{d}{\lambda_{nm}}\right)$$

The reflected signal arriving back at the smartphone microphone is:

$$P_{rx}(x, t, w_{nm}) = Ae \ \sigma(1-\alpha)\frac{P_0}{(4\pi)^2 d^{(\beta+\gamma)}} \sin 2\pi\left(f_{nm}t + \frac{2d}{\lambda_{nm}}\right)$$

If the target distance is moving with a sinusoidal variation about d such that $$d(x,t,w_b,A_b) = d_0 + A_b \sin(2\pi f_b t + \theta)$$

where:
Breathing Frequency: $w_b = 2\pi f_b$
Breathing Amplitude: $A_b$
Breathing Phase: $\theta$
Nominal target distance: $d_0$ Because maximum breathing displacement $A_b$ is small compared to target distance d, its effect on receive signal amplitude can be ignored. As result the smartphone microphone breathing signal becomes:

$$P_{rx}(x, t, w_{nm}) = Ae \ \sigma(1-\alpha)\frac{P_0}{(4\pi)^2 d^{(\beta+\gamma)}} \sin 2\pi\left(f_{nm}t + \frac{2d_0 + 2A_b \sin(2\pi f_b t + \theta)}{\lambda_{nm}}\right)$$

Because an idealized respiratory movement signal, which may be similar to a cardiac movement signal albeit at different frequencies and displacements, could be thought of as a sinusoidal function of a sinusoidal function, it will have areas of maximum and minimum sensitivity for the same displacement peak to peak amplitude.

To correctly recover this signal, it is beneficial to utilize a quadrature phase receiver or similar so that sensitivity nulls are mitigated.

The I and Q baseband signals can then be utilized as a phasor I+jQ to:
1. Recover the RMS and Phase of the breathing signal
2. Recover the direction (phasor direction) of the movement
3. Recover foldover information by detecting when the phasor changes direction 5.1.2.2.2.2.3 FHRG Demodulator Mixer (Module at 705 and 706 in FIG. 7)

The FHRG softmodem (frontend for acoustic sensing (sonar) detection-software based modulator/demodulator) transmits a modulated sound signal through the speaker and senses the echo reflected signal from the target through the microphone. An example of a softmodem architecture is presented in FIG. 7. The softmodem receiver that processes the sensed reflection as a received signal is designed to perform a multiplicity of tasks including:
High pass filter the received signal at audio frequencies
Synchronize with the frame timing of the modulated audio
Demodulate the signal to baseband utilizing a quadrature phase synchronous demodulator
Demodulate the IF (intermediate frequency) component if present
Low pass filter (e.g., Sinc filter) the resultant in phase and quadrature baseband signal
Reproduce the I and Q baseband signal from a multiplicity of I,Q signals at different frequencies.

The softmodem demodulator (e.g., module at 705 and 706 in FIG. 7) utilizes a local oscillator (shown as "A $\sin(\omega_1 t)$" in the module at 706) with a frequency synchronous to that of the received signal to recover the phase information. The module at 705 (the Frame Demodulator) selects and separates each tone pair for subsequent IQ demodulation of each pair—i.e., defining each ($\omega t$) for the IQ demodulation of a tone pair. The in-phase (I) signal recovery will be discussed. The quadrature component (Q) is identical but utilizes a local oscillator (shown as "A $\cos(\omega_1 t)$" in the module at 706) with a 90-degree phase change.

Given a pressure signal sensed at the microphone that is accurately reproduced as an equivalent digital signal and the input high pass filter (e.g., filter 702) is ideal, the audio signal received by the smartphone softmodem demodulator is:

$$y(x, t, w_{nm}) = A \sin 2\pi\left(f_{nm}t + \frac{2d}{\lambda_{nm}}\right) + \sum D_j \sin(2\pi f_j t + \varphi_j)$$

Where:
The amplitude A is determined by the sonar parameters:

$$A = Ae \ \sigma(1-\alpha)\frac{P_0}{(4\pi)^2 d^{(\beta+\gamma)}}$$

The distance d is modulated by the target movement:
$d = d_0 + A_b \sin(2\pi f_b t + \theta)$
Where static clutter reflections/interference signals are represented as:

$$\Sigma D \sin(2\pi f_j t + \varphi_j)$$

The in-phase demodulator output signal for any received signal, when correctly synchronized, is:

$$(x, t, w_{nm}) = \sin(w_{nm}t)\left\{A \sin 2\pi\left(f_{nm}t + \frac{2d}{\lambda_{nm}}\right) + \sum D_i \sin(2\pi f_j t + \varphi_j)\right\}$$

This demodulation operation follows the trigonometric identity:

$A \sin(w_1 t + \varphi) B \sin(w_2 t + \theta) = AB \cos[(w_1 t + \varphi) - (w_2 t + \theta)] - AB \cos[(w_1 t + \varphi) + w_2 t + \theta]$ When the local oscillator and receive signal have the same angular frequency $w_1$ this reduces to:

$A \sin(w_1 t + \varphi) B \sin(w_1 t + \theta) = AB \cos(\varphi - \theta) - AB \cos[(2w_1 t + \theta + \varphi)]$ Which after low pass filtering (shown as LPF in FIG. 7) to remove $2w_1 t$ produces:

$$A \sin(w_1 t + \varphi) B \sin(w_1 t + \theta) = AB \cos(\varphi - \theta)$$

In this way, the low pass filtered synchronous phase demodulator output signal for any received signal, when correctly synchronized is:

$$y_{nm}(x, t, w_{nm}) = Ae\, \sigma(1-\alpha)\frac{P_0}{(4\pi)^2 d^{(\beta+\gamma)}} \cos 2\pi\left(\varphi + \frac{2d_0 + 2A_b \sin(2\pi f_b t + \theta)}{\lambda_{nm}}\right)$$

5.1.2.2.2.2.4 FHRG Demodulator Sinc Filter

The smartphone softmodem demodulator utilizes an oversampling and averaging Sinc filter as the "LPF" of the demodulator module at 706 to remove unwanted components and decimate the demodulated signal to the baseband sampling rate.

The received frame comprises both tone pairs which are transmitted together in the same tone burst (e.g., where two or more pairs of tones are played at the same time) and also comprises tone hops which are transmitted in subsequent tone burst times. When demodulating the return signal, for example f_(ij) the unwanted demodulated signal must be removed. These include:

baseband signals spaced at frequencies: $|f_{ij} - f_{nm}|$
aliased components due to the sampling process at both $|2f_{nm} - f_s|$ and $|f_{nm} - f_s|$
demodulated audio frequency components at: $2f_{nm}$
audio carrier at $f_{nm}$ which might come through the demodulator due to non-linearity.

To achieve this, a low pass filter LPF (such as a Sinc filter) may be used. The Sinc filter is almost ideal for the purpose as it has a filter response with zeros at all the unwanted demodulation components by design. The transfer function for such a moving average filter of length L is:

$$H(\omega) = \left(\frac{1}{L}\right)\frac{(1 - e^{-j\omega L})}{(1 - e^{-j\omega})}$$

Figure 9:
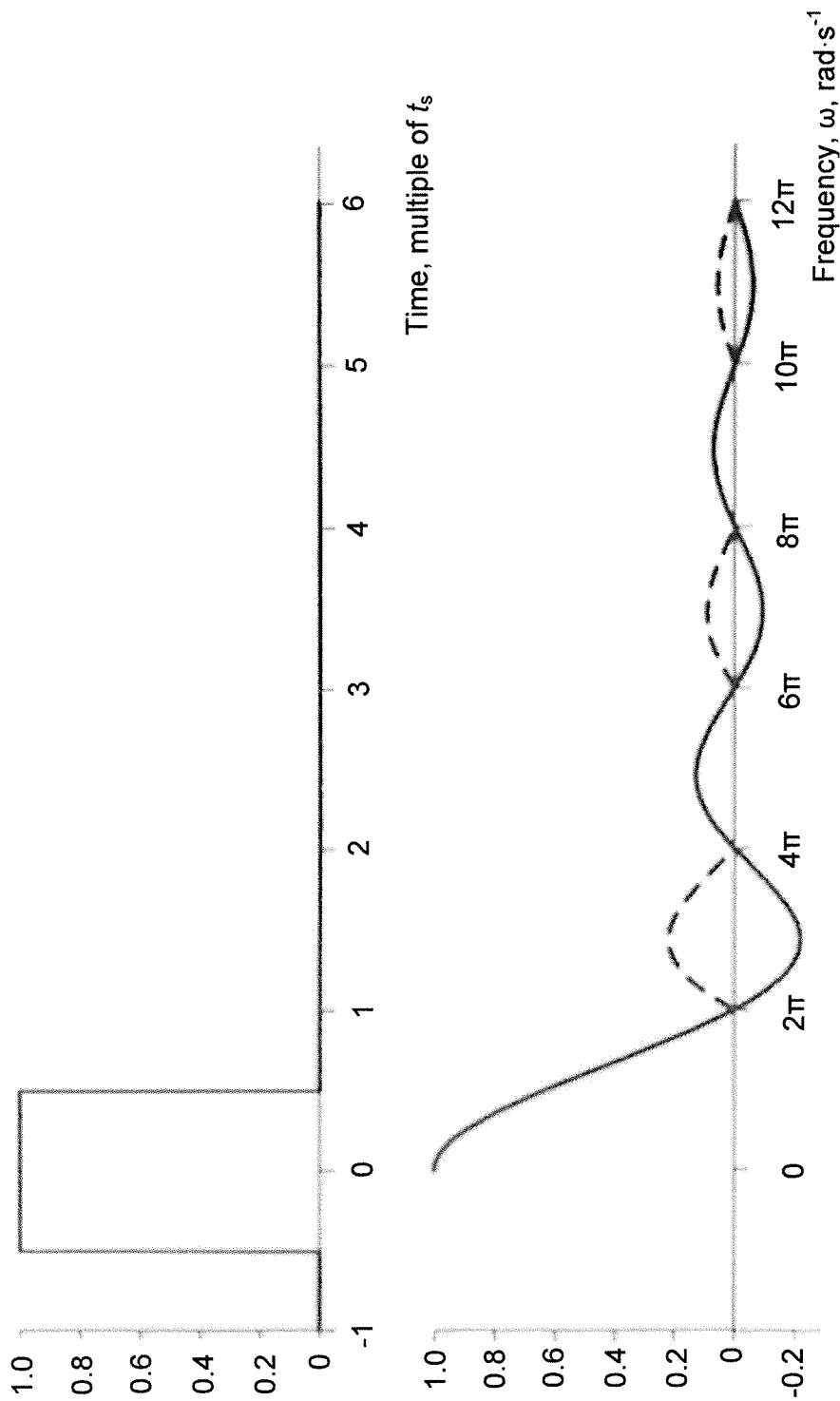
FIG. 9 illustrates an example of a sinc filter response.
Figure 10:
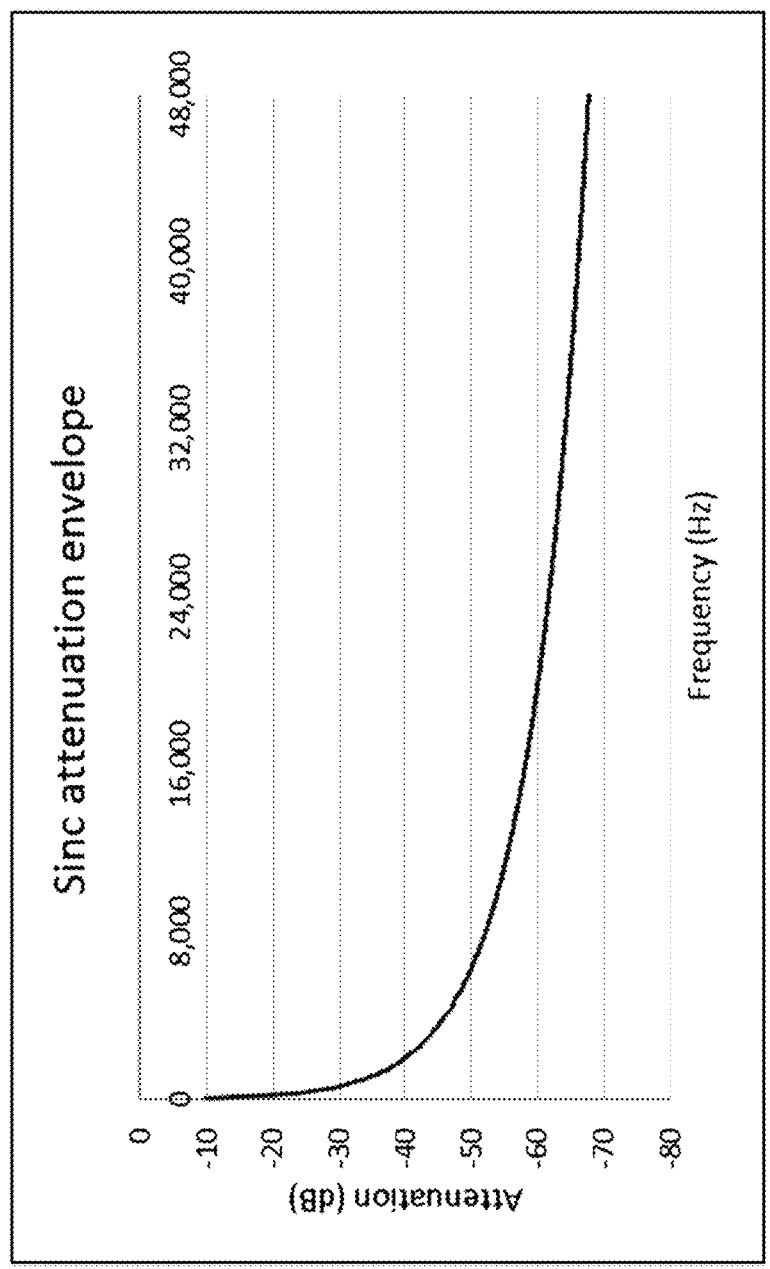
FIG. 10 illustrates an example of attenuation characteristics of a sinc filter.

FIG. 9 illustrates an example of a Sinc filter response, while FIG. 10 shows the worst case attenuation characteristics of the 125 Hz Sinc filter due to the averaging of 384 samples over an 8 ms period.

5.1.2.2.2.2.5 Demodulator Baseband Signal

The smartphone softmodem transmits a modulated tone frame. The frame comprises multiple tone pairs (e.g., two tone pairs having four tones) which are transmitted together in the same tone burst and also comprises tone hops which are transmitted in subsequent tone burst times.

First we will discuss the demodulation of a tone pair. Because tone pairs are transmitted, reflected and received simultaneously, their only demodulated phase difference is due to tone pair frequency difference.

Before the "time of flight" time:

$$t_{tof} = \frac{2d}{v}$$

there is no return reflected signal and hence the demodulator outputs for both tone pair components is a DC level due to near end crosstalk and static reflections.

After the "time of flight" time this DC level receives a contribution from the moving target component. The demodulator output now receives as:

a) For the in-phase (I) demodulator signal output for each tone pair frequency we get:

$$I_{11}(x, t, w_{11}) = \sum Ae\, \sigma(1-\alpha)\frac{P_0}{(4\pi)^2 d^{(\beta+\gamma)}} \cos 2\pi\left(\frac{2d_0 + 2A_b \sin(2\pi f_b t + \theta)}{\lambda_{11}}\right)$$

$$I_{12}(x, t, w_{12}) = \sum Ae\, \sigma(1-\alpha)\frac{P_0}{(4\pi)^2 d^{(\beta+\gamma)}} \cos 2\pi\left(\frac{2d_0 + 2A_b \sin(2\pi f_b t + \theta)}{\lambda_{12}}\right)$$

b) For the quadrature (Q) demodulator signal output for each tone pair frequency we get $$Q_{11}(x, t, w_{11}) = \sum Ae\, \sigma(1-\alpha)\frac{P_0}{(4\pi)^2 d^{(\beta+\gamma)}} \sin 2\pi\left(\frac{2d_0 + 2A_b \sin(2\pi f_b t + \theta)}{\lambda_{11}}\right)$$

$$Q_{12}(x, t, w_{12}) = \sum Ae\, \sigma(1-\alpha)\frac{P_0}{(4\pi)^2 d^{(\beta+\gamma)}} \sin 2\pi\left(\frac{2d_0 + 2A_b \sin(2\pi f_b t + \theta)}{\lambda_{12}}\right)$$

The summation $\Sigma$ of each of these samples in the demodulated tone burst receive signal results in "Sinc" filtering of the frequencies. This filter is designed to average the required receive tone burst to enhance the signal to noise and produce zeros in the transfer function at the unwanted demodulated tone burst frequencies spaced every $f_{nm} - f_{11}$ in order to reject all these frequencies.

This summation occurs during the full tone burst period but the component due to movement only occurs from after the time of flight period until the end of the tone pair burst period, i.e.:

From $$t_{tof} = \frac{2d_0}{v} \text{ until } t_p = \frac{1}{f_{11} - f_{12}}$$

As result of the time of flight a further signal attenuation factor is introduced into the signal recovery. The attenuation factor is:

$$\frac{t_p - t_{tof}}{t_p} = 1 - \frac{d}{D}$$

which is a linear decrease in amplitude up to maximum range D.

The demodulation of the audio signal and subsequent averaging at the frame rate when the frame comprises n sequential tone pairs produces a baseband signal with a sample rate of:

$$\frac{1}{n\, t_p}$$

samples per second and provides 2n different I and Q baseband demodulated signals.

5.1.2.2.2.2.6 Demodulator $I_{mn}$ and $Q_{mn}$

The result of this demodulation and averaging operation is the demodulation of the tone pair audio frequencies to four separate baseband signal samples, namely $I_{11}$, $I_{12}$, $Q_1$, $Q_{22}$, at the sampling rate of:

$$\frac{1}{n\, t_p}$$

samples per second.

During subsequent periods of the frame this operation is repeated for different frequencies which are separated in frequency from the previous pair by $1/t_p$ to maintain optimum rejection by the Sinc filter function.

This sampling procedure is repeated every frame to generate a multiplicity of baseband signals. In the example given, it produces 2×4×I and 2×4×Q baseband signals, each with their own phase characteristic due to the trigonometric identity:

$$\cos 2\pi\left(\frac{2d_0 + 2A_b \sin(2\pi f_b t + \theta)}{\lambda_{nm}}\right)$$

Figure 11:
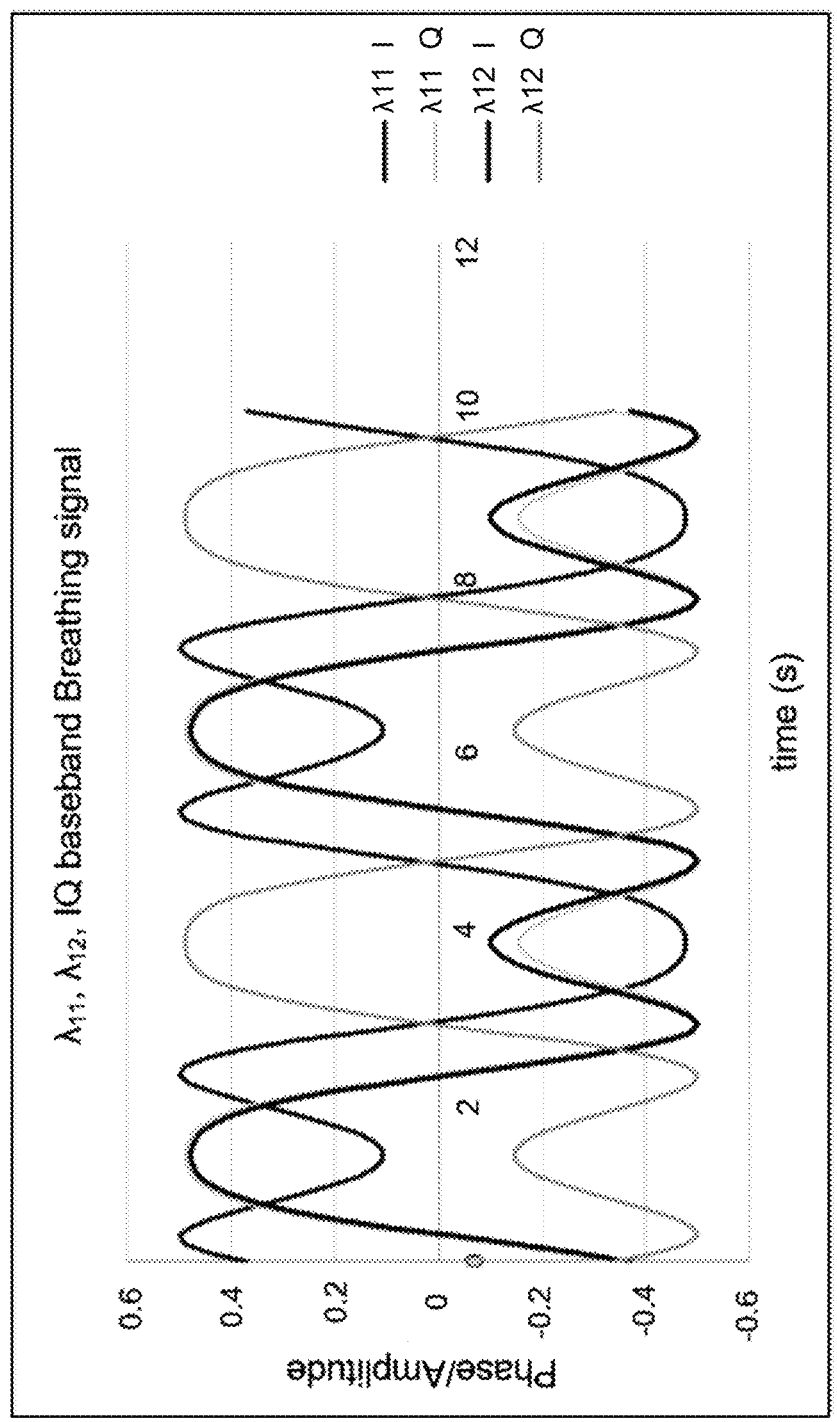
FIG. 11 is a graph illustrating an example of a baseband breathing signal.

An example of the phase change by the first tone pair at 1 m with a moving target is depicted in FIG. 11.

Figure 12:
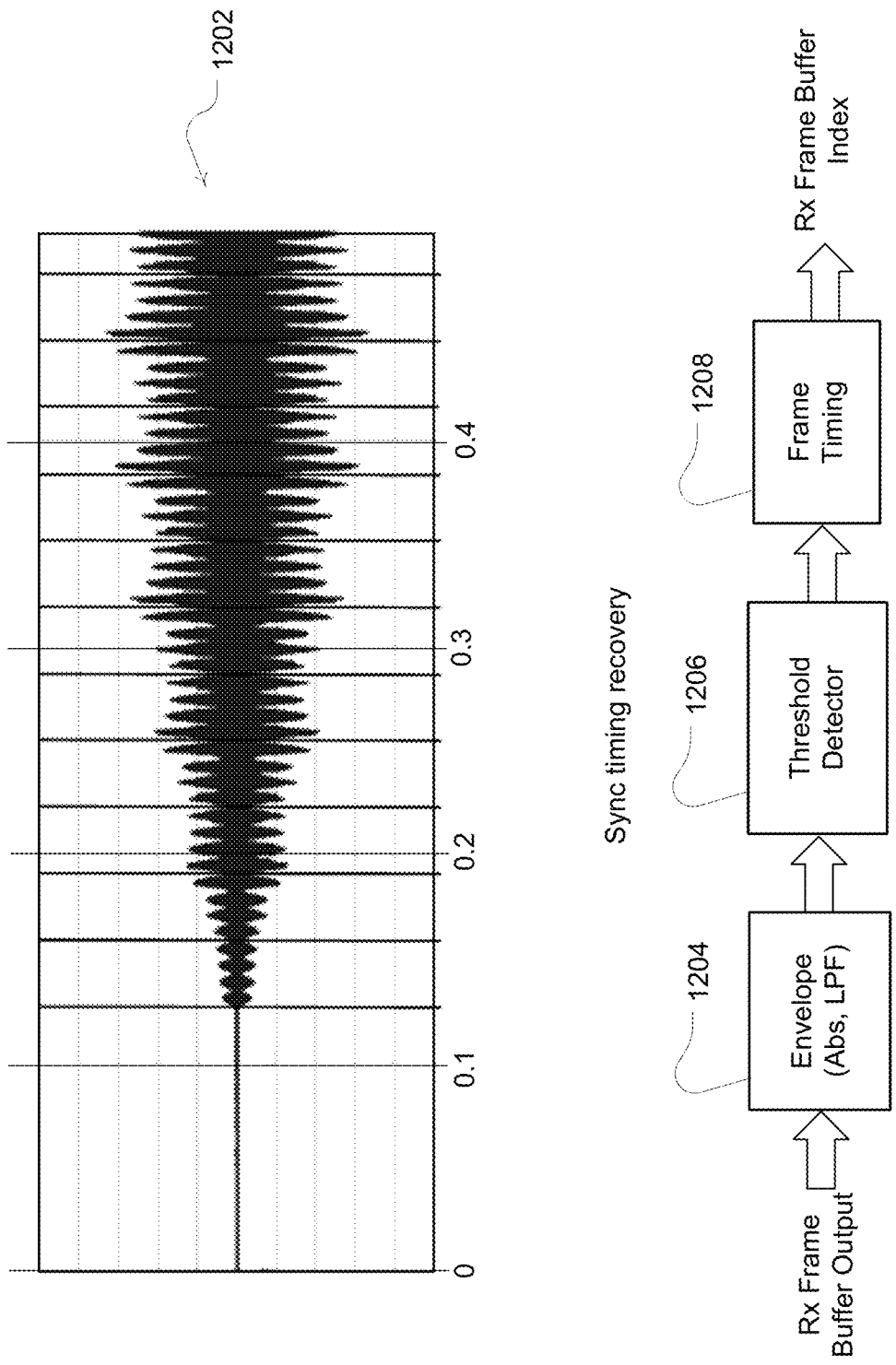
FIG. 12 illustrates an example of initial synchronization with a training tone frame.

The AFHRG architecture provides for tight timing synchronization facilitated by the time, frequency, and envelope amplitude characteristics of the tone pair such as with a frame synchronization module 703. Audio Tx and Rx frames may be asynchronous. Upon initialization, the mobile device might be expected to maintain perfect Tx-Rx synchronization. According to some aspects of the disclosure, and as shown in FIG. 12, initial synchronization may be achieved with a training tone frame, which may comprise nominal frame tones, as shown at 1202. The Rx signal may be IQ demodulated by IQ demodulator 706, as shown above with respect to FIG. 7. The envelope may then be computed (e.g., via taking the absolute value, followed by low pass filtering, or using a Hilbert transform), as shown at 1204, and the timing extracted using level threshold detection, as shown at 1206. The shape of the A $\sin(\omega_1 t)$–A $\sin(\omega_2 t)$ pulse assists auto correlation and may be configured to improve precision and accuracy. The Rx circular buffer index may then set for the correct synchronized timing, as shown at 1208. In some aspects of the disclosure, a training tone frame may not be used; rather, the Rx may be activated followed by a short period of time before the TX is activated, and a threshold may be used to detect the start of the TX frame after the short recorded silence period. The threshold may be selected to be robust to background noise, and prior knowledge of the Tx signal rise time may be used to create an offset from true Tx start, and thus correct for the threshold detection that occurs during said rise time. When considering the estimated envelope of the signal, peak and "trough" (where the trough is around the zero line, due to the absolute value being taken) fiducial points detection may be performed, using a detection algorithm that may adapt based on the relative signal levels. Optionally, only the peaks may be processed, as the troughs may be more likely to contain noise due to reflections.

In some cases, a device (such as a mobile device) may lose synchronization due to other activity or processing causing a jitter or drop in audio samples. Accordingly, a resynchronization strategy may be required, such as with the frame synchronization module 703. According to some aspects of the disclosure, introduction of periodic training sequences may be implemented to regularly confirm that synchronization is good/true. An alternative approach (which may optionally also make use of such periodic training sequences, but does not such use), is to cross correlate a known Tx frame sequence (typically a single frame) along a segment of Rx signal iteratively until a maximal correlation above a threshold is detected. The threshold may be chosen to be robust to the expected noise and multipath interference in the Rx signal. The index of this maximal correlation may then be used as an index to estimate the synchronization correction factor. It is noted that a de-synchronization in the demodulated signal may appear as a small or profound step (usually the latter) in the baseline. Unlike the near step response seen in some real large motion signals, the de-synchronized segment does not hold useful physiological information, and is removed from the output baseband signal (which may lead to the loss of some number of seconds of signal).

Thus, synchronization typically makes use of prior knowledge of the transmit signal, with initial alignment being performed through a technique such as envelope detection, followed by selection of the correct burst utilizing cross-correlation between received signal Rx and known transmit signal Tx. Loss of synchronization checks should ideally be performed regularly, and optionally include data integrity tests.

An example of such an integrity test, for the case of a new synchronization being performed, a check may be performed to compare the new synchronization with the timing of one or more previous synchronization(s). It would be expected that the time difference between candidate synchronization times in samples would be equal to an integer number of frames within an acceptable timing tolerance. If this is not the case, then a likely loss of synchronization has occurred. In such a case, the system may initiate a re-initialization (e.g., with a new training sequence (that is unique in the local time period), the introduction of a defined period "silence" in Tx, or some other marker). In such cases, data sensed since the potential de-sync event may be flagged as questionable and may potentially be discarded.

Such de-sync checking may be performed continually on the device, and build up useful trend information. For example, if regular de-syncs are detected and corrected, the system may adapt the audio buffer lengths to minimize or stop such undesirable behavior, or make changes to processing or memory load, such as deferring some processing to the end of a sleep session, and buffering data for such processing rather than executing complex algorithms in real or near real-time. It can be seen that such re-synchronization approaches are valid and useful for a variety of Tx types (FHRG, AFHRG, FMCW etc.)—especially when utilizing a complex processor such as a smart device. As described, the correlation may be performed between the envelope of the reference frame and estimate envelope of the Rx sequence, although, the correlation could also be performed directly between a reference frame and an Rx sequence. Such correlation can be performed in the time domain or in the frequency domain (e.g., as a cross spectral density or cross coherence measure). There are also circumstances where the Tx signal stops being generated/playing for a period of time (when it is expected to be playing or due to a user interaction such as selecting another app on a smart device, or receiving a call), and re-synchronization is paused until the Rx sees a signal above a minimal level threshold. Potentially, de-sync could also occur over time if a device's main processor and audio CODEC are not perfectly synchronized. For suspected longer duration de-sync, a mechanism to generate and play a training sequence may be used, Note that a de-sync can produce a signal that looks like a DC shift and/or step response in the signal, and the mean (average) level or trend may change after a de-sync event. Furthermore, a de-sync may also happen due to external factors such as a loud noise (e.g., a brief impulse or sustained period) in the environment; for example, a loud bang, something knocking against the device containing the mic or a nearby table, very loud snoring, coughing, sneezing, shouting etc. could cause the Tx signal to be drowned out (noise sources have similar frequency content to Tx, but at higher amplitude), and/or the Rx to be swamped (going in to saturation, hard or soft clipping, or potentially activating the automatic gain control (AGC)).

Figure 13:
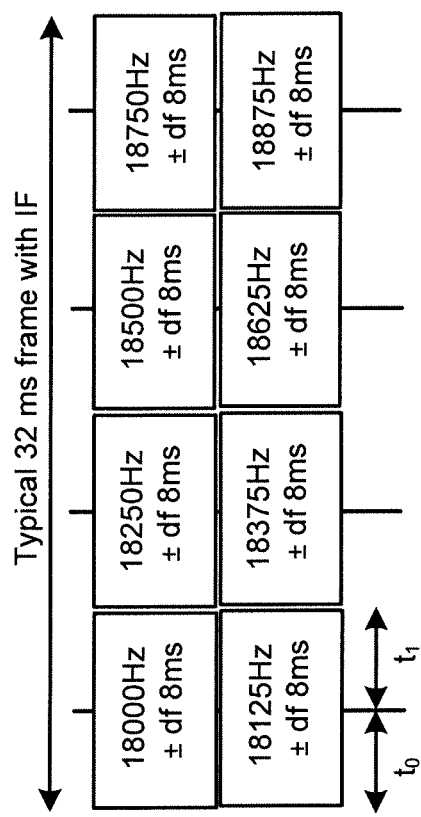
FIG. 13 illustrates an example of an AFHRG frame with an intermediate frequency.

FIG. 13 illustrates an example of a 32 ms frame with intermediate frequency. According to some aspects of the disclosure, the IF stage may be configured to compare early 4 ms (0.5 m range) signals with later 4 ms signals. In accordance with other aspects of the disclosure, the IF stage may be configured to compare the phase of a first tone with the phase of a second tone. Because the IF stage compares the level or phase change in the receive signal within the time of flight, common mode signal artefacts such as motion and 1/f noise may be reduced or removed.

Room reverberation can produce room modes at resonant frequencies. The AFHRG architecture allows for the shift of the fundamental frequencies once the frame frequency separation is maintained. The pulse pair frequencies may be shifted to a frequency that does not produce room modes. In other embodiments, the frame pulse pair frequencies may be hopped to lessen the build-up of mode energy. In other embodiments, the fame pulse pair frequencies may be hopped using a long, non-repetitive pseudorandom sequence, throughout the frequency specific reverberation time to prevent the reflections being seen by the homodyne receiver. The frame frequency may be dithered to alleviate interference from modes, or a sinusoidal frame shift may be used.

Use of an AFHRG system provides many advantages. For example, such a system allows for adaptable transmit frequencies to mitigate room modes. The system uses active transmitting with a repeated pulse mechanism and different frequencies to improve SNR, unlike a typical "quiet period" required in say a pulsed continuous wave RADAR system. In this regard, subsequent tone pairs at different frequencies from a prior tone pair in a frame implements a "quiet period." The subsequent frequencies allow settling of the propagation of the reflected sound from the earlier different frequency tone pair while the subsequent tone pairs are in operation (propagating). Time slots provide range gating to a first order. Moreover, the architecture uses dual frequency pulses to further improve SNR. Inclusion of an intermediate frequency phase provides for defined and/or programmable range gating. The architecture is designed to allow for slow sampling periods using Costas or pseudorandom frequency hopping code to mitigate room reverberation. In addition, the orthogonal Dirac Comb frequencies also allow for frame timing dithering and tone frequency dithering to further assist noise reduction.

It should be noted that a wider or a narrower bandwidth could also be chosen in AFHRG. For example, if a particular handset can transmit and receive with good signal strength up to 21 kHz, and the subject using the system can hear up to 18 kHz, a 2 kHz bandwidth of 19-21 kHz might be selected for use by the system. It can also be seen that these tone pairs can be hidden in other transmitted (or detected ambient) audio content, and adapt to changes in the other audio content to remain masked from the user. The masking may be achieved by transmitting audible (e.g., from, for example, about 250 Hz upwards) or inaudible tone pairs. Where the system is operating at, for example, about over 18 kHz, then any generated music source may be low pass filtered below about 18 kHz; conversely, where the audio source cannot be directly processed, then the system tracks the audio content, and injects a predicted number of tone pairs, and adapts to both maximize SNR, and minimize audibility. In effect, elements of the existing audio content provide the masking for the tone pair—where the tone pair(s) are adapted to maximize the masking effect; the auditory masking is where the perception of the tone pair is reduced or removed.

An alternate approach when generating or playing an acoustic signal (e.g., music) to using (A) FHRG, FMCW, UWB etc. (with or without masking) is to directly modulate the carrier. In such a case, the sensing signal is directly encoded in the played signal by adjusting the signal content (specifically by varying the amplitude of the signal). The subsequent processing comprises demodulating the incoming (received) signal vs. outgoing (generated/transmitted) signal by mixing and then low pass filtering to get baseband signal. The phase change in the carrier signal is proportional to movement such as breathing in the vicinity of the sensor. One caveat is if the music naturally changes amplitude or frequency at the breathing frequency due to an underlying beat, then this can increase noise on the demodulated signal. Also, in quite periods in the playback, an extra signal may need to be injected (such as amplitude modulated noise) in order to continue detecting breathing during this time, or the system may simply ignore the baseband signal during such quiet playback periods (i.e., in order to avoid the need to generate a 'filler' modulated signal). It can also be seen that instead of (or in addition to) amplitude modulating an audio signal (such as a music signal), it is possible to phase code the signal with defined phase segments, and then demodulate the received signal, and track the phase change in the received signals during the encoded intervals, in order to recover a baseband signal.

5.1.2.2.2.3 Adaptive Time of Flight

Figure 14:
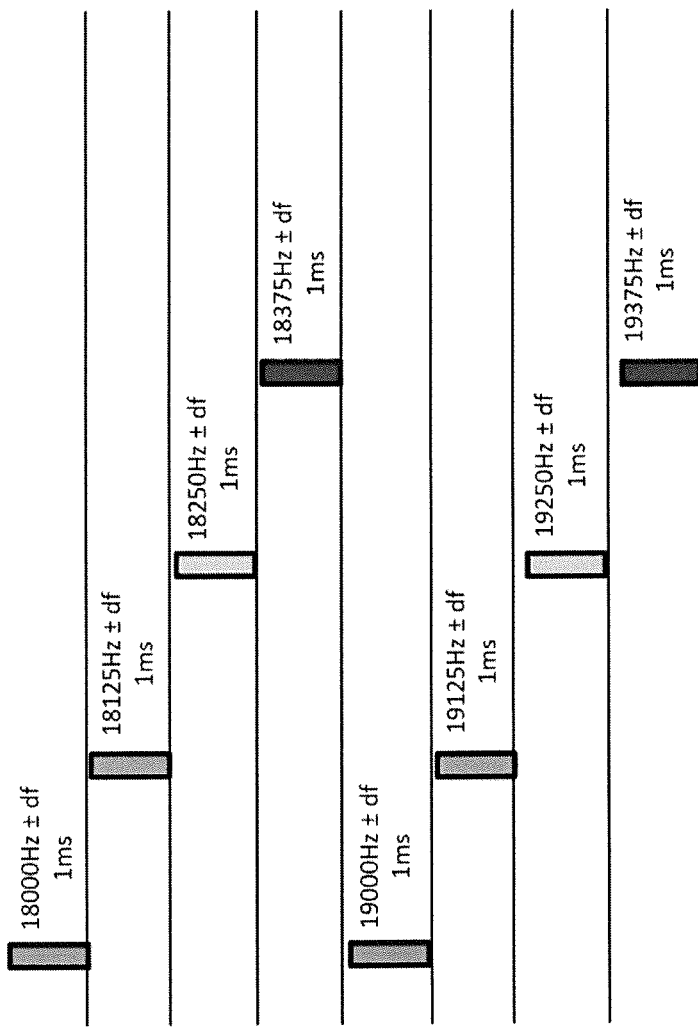
FIG. 14 illustrates an example of an AToF frame.

According to some aspects of the disclosure, an Adaptive Time of Flight (AToF) architecture can be used to mitigate room acoustic issues. The AToF architecture is similar to AFHRG. Like AFHRG, AToF uses the normally quiet period to enhance SNR by repeating the pulses. For example, four individual homodyne pulsed sonar signals could be transmitted in each frame. Each signal may have an 8 ms time of flight. At 8 ms time of flight, the range, including both directions, is 2.7 meters giving an effective actual frame of 1.35 m, and a pulse repetition frequency of 31.25 Hz. Additionally, each pulse may include two pulse frequencies, as shown in FIG. 14, resulting in 8 separate pulsed homodyne signals in a single 32 ms transceiver frame. Unlike the AFHRG architecture, AToF uses pulses that last 1 ms instead of 8 ms.

Like AFHRG, ATOF may use Dirac Comb features and orthogonal pulse pairs to help shape the pulse. AToF may use separate frequency pairs for each timeslot and may use linear or Costas code frequency hopping. The timeslot may be determined by the range detection required. Frequency pairs may be generated as $\{A\ Sin(\omega_1 t) - A\ Sin(\omega_2 t)\}$ with $$\omega_1 - \omega_2 = \frac{2\pi}{1 \text{ ms}}.$$

Each frame may be adapted, by adjusting its frequency inside a fixed band, to mitigate fading once the requirements of the frequency pairs equation is met.

In summary, some advantages of frequency pairs (versus say multiple individual tones at different frequencies) include:

Frequency flexibility: It allows any frequency to be used in any timeslot time (once $$f_1 - f_2 = \frac{1}{t_{ts}}$$

which enables frequency shifting adaptability to mitigate room modes and fading

S/N (impact on SNR): Increases the signal to noise as result of improved bandwidth utilization (with allowance for scaling of the edges of the pulse)

Transient mitigation: Provides a near ideal zero crossing transition which mitigates frequency hopping transients at both transmitter and receiver and allows for true pseudo random frequency hopping capability. This leads to an inaudible system.

Facilitates synchronization recovery: The unique frequency and amplitude profile of the shaped pulse improves synchronization detection and accuracy (i.e., there is a clear shape)

Pulse and frame timing flexibility: Allows for any timeslot time duration to facilitate a "variable detection range" feature Facilitates dithering: Enables both frequency dithering and time slot dithering to mitigate noise Tight BW: Naturally produces a very tight bandwidth and so is inaudible even without filtering (filters can introduce phase distortion)

MultiTone: It allows the use of multiple tones in the same timeslot to enhance S/N and mitigate fading.

5.1.2.2.2.4 Frequency Modulated Continuous Wave (FMCW)

In yet another aspect of the disclosure, a frequency modulated continuous wave (FMCW) architecture may be used to mitigate some of the technical challenges described above. FMCW signals are typically used to provide localization (i.e., distance as well as speed) as FMCW enables range estimation and thus provide range gating. An example of an audible sawtooth chirp in daily life is like a chirp from a bird, whereas a triangle chirp might sound like a police siren, for example. FMCW may be used in RF sensors, and also acoustic sensors, such as implemented on a typical smart device such as a smartphone or tablet, using inbuilt or external loudspeaker(s) and microphone(s).

It should be noted that audible guide tone(s) (e.g., played at the start of a recording, or when a smart device is moved) can be used to convey the relative "loudness" of inaudible sounds. On a smart device with one or more microphones, a profile is selected to minimize (and, ideally, make unnecessary) any extra processing in software or the hardware CODEC such as to disable echo cancellation, noise reduction, automatic gain control etc. For some handsets, the camcorder mic or main microphone configured to be in "voice recognition" mode may provide good results, or the selection of an "unprocessed" mic feed such as one that might be used for virtual reality applications or music mixing. Depending on the handset, a "voice recognition" mode such as available in some Android OS revisions may disable effects and pre-processing on the mic (which is desirable).

FMCW allows tracking across a spatial range, so determination of where a breathing person is, if they have moved, and to separate two or more people breathing when in the range of the sensor (i.e., a breathing waveform from each subject at a different range can be recovered).

FMCW can have a chirp, such as a ramp sawtooth, triangle, or sinusoidal shape. Thus, unlike pulses of an (A) FHRG type system, the FMCW system may generate a repeated waveform of sound (e.g., inaudible) that has changing frequencies. It is important to match frequency changes at zero crossings of the signal if possible—i.e., to avoid jump discontinuities in the generated signal that can give rise to unwanted harmonics that may be audible and/or unnecessarily stress the speaker. The ramp sawtooth may ramp up (from lower to higher frequencies) like the form of the ramp illustrated in FIG. 15B. When repeated, the ramp up forms an upward saw, by repeating the lower to higher, lower to higher, etc. waveform (ramp sawtooth). However, such a ramp may alternatively ramp down (from higher to lower frequencies). When repeated, the ramp down forms a downward saw, by repeating the higher to lower, higher to lower, etc. waveform (inverted ramp sawtooth). Moreover, although such ramping may be approximately linear using a linear function as illustrated, in some versions, the rise in frequency may be form a curve (increasing or decreasing) such as with a polynomial function between the low and high (or the high and low) of the frequency change of the waveform.

In some versions, the FMCW system may be configured to vary one or more parameters of a form of the repeated waveform. For example, the system may vary any one or more of (a) a location of a frequency peak in a repeated portion of the waveform (e.g., peaking earlier or later in the repeated portion). Such a varied parameter may be a change in slope of a frequency change of the ramp of the waveform (e.g., the slope up and/or the slope down). Such a varied parameter may be a change in the frequency range of a repeated portion of the waveform.

A particular method to achieve such an inaudible signal for use on a smartdevice using an FMCW triangle waveform is outlined here.

For an FMCW system, the theoretical range resolution is defined as: V/(2*BW), where V is velocity, such as for sound, and BW is bandwidth. Therefore, for V=340 m/s (at say room temperature) and an 18-20 kHz chirp FMCW system, an 85 mm range resolution for separating targets is possible. Each of one or more moving targets (such as the breathing movement of a subject) can then be detected with much finer resolution individually (similar to a CW system), assuming that (in the case of this example), each subject is separated by at least 85 mm in the field of the sensor.

Depending on the relative sensitivity to frequency of speaker and/or microphone, the system may optionally use emphasis on the transmitted signal Tx FMCW waveform in order that each frequency is corrected to have the same amplitude (or other modification to the transmit signal chirp in order to correct for non-linearities in the system). For example, if the speaker response decreases with increasing frequency, a 19 kHz component of the chirp is generated at higher amplitude than an 18 kHz component, such that the actual Tx signal will have the same amplitude across the frequency range. It is of course important to avoid distortion, and the system may check the received signal for an adjusted transmit signal, in order to determine that distortion (such as clipping, unwanted harmonics, jagged waveform etc.) does not occur—i.e., to adjust the Tx signal such as to be as close to linear as possible, at as large an amplitude as possible, to maximize SNR. A system as deployed may scale down the waveform and/or reduce volume to meet a target SNR to extract respiratory parameters (there is a tradeoff between maximizing SNR and driving the loudspeaker(s) hard)—while maintaining as linear a signal as feasible.

Based on channel conditions, the chirp may also be adapted by the system—e.g., to be robust to strong interfering sources, by adapting the bandwidth used.

5.1.2.2.2.5 FMCW Chirp Types, and Inaudibility

FMCW, at audible frequencies, has a period of 1/10 ms=100 Hz (and associated harmonics) that is clearly audible as buzzing sound unless further digital signal processing steps are performed. The human ear has an incredible ability to discern very low amplitude signals (especially in a quiet environment such as a bedroom), even if high pass filtering removes components down to −40 dB (filtering of unwanted components to below −90 dB may be required). For example, the start and end of the chirp can be de-emphasized (e.g., to window the chirp with a Hamming, Hanning, Blackman etc. window), and then re-emphasized on subsequent processing in order to correct.

It is also possible to isolate the chirp—e.g., only repeat every 100-200 ms to introduce a quiet period between chirps that is much longer than a single chirp in duration; this can have a side benefit of minimizing the detection of reverberation related standing waves. A downside of this approach as less of the available transmit energy is used versus a continuous repeating chirp signal. A trade-off is that reducing the audible clicks and reducing the continuous output signal does have some benefits in terms of driving the device (e.g., a smart device such as a phone loudspeaker) loud speaker and amplifier less hard; for example, a coil loud speaker may be impacted by the transients if driven at maximum amplitude over a long period of time.

Figure 15A:
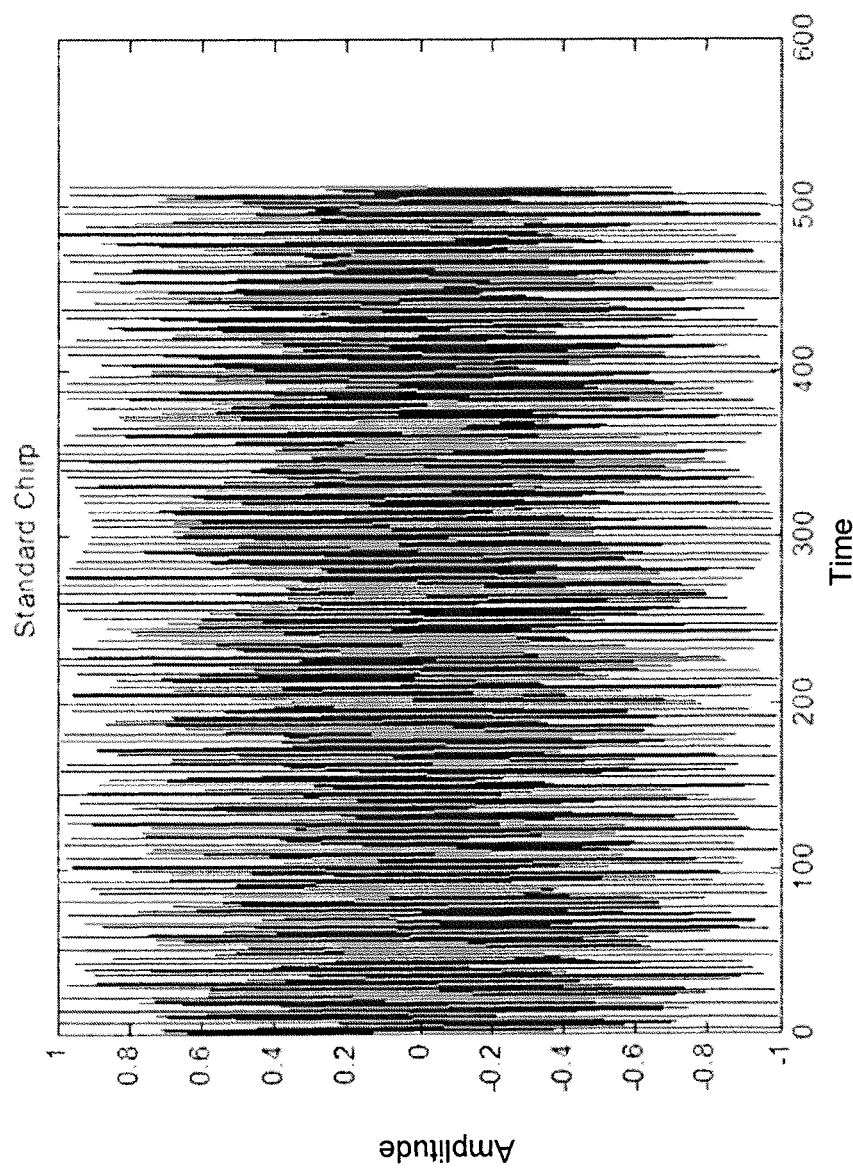
FIGS. 15A, 15B and 15C illustrate signal characteristics of an example of an audible version of an FMCW ramp sequence.
Figure 15B:
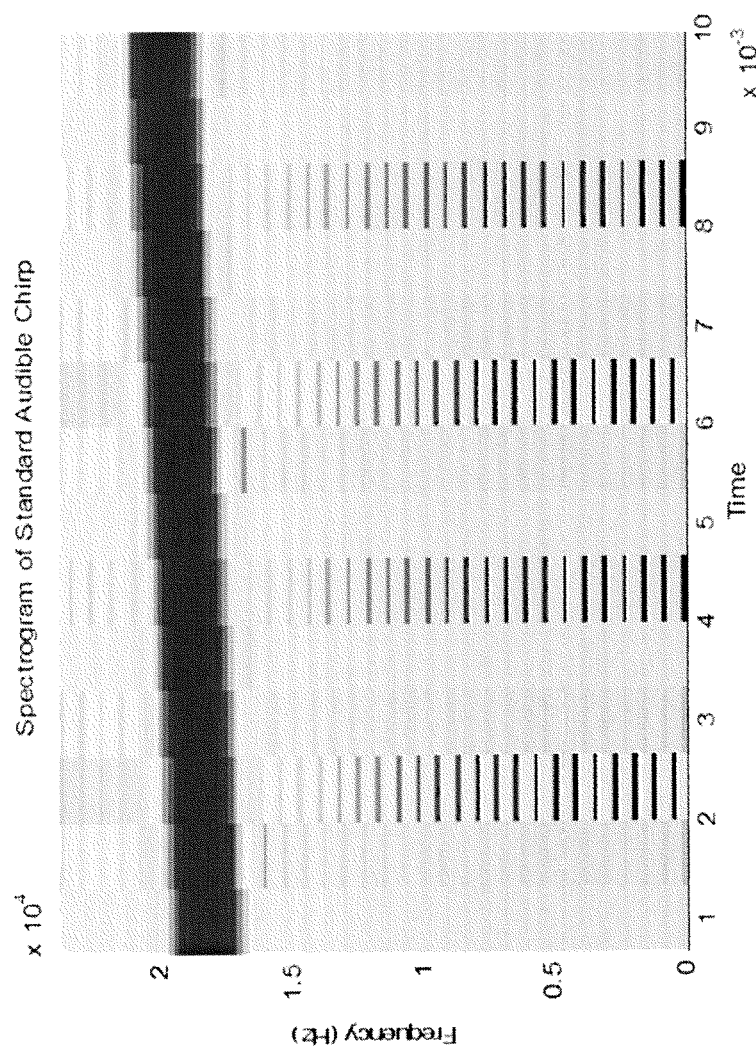
Figure 15C:
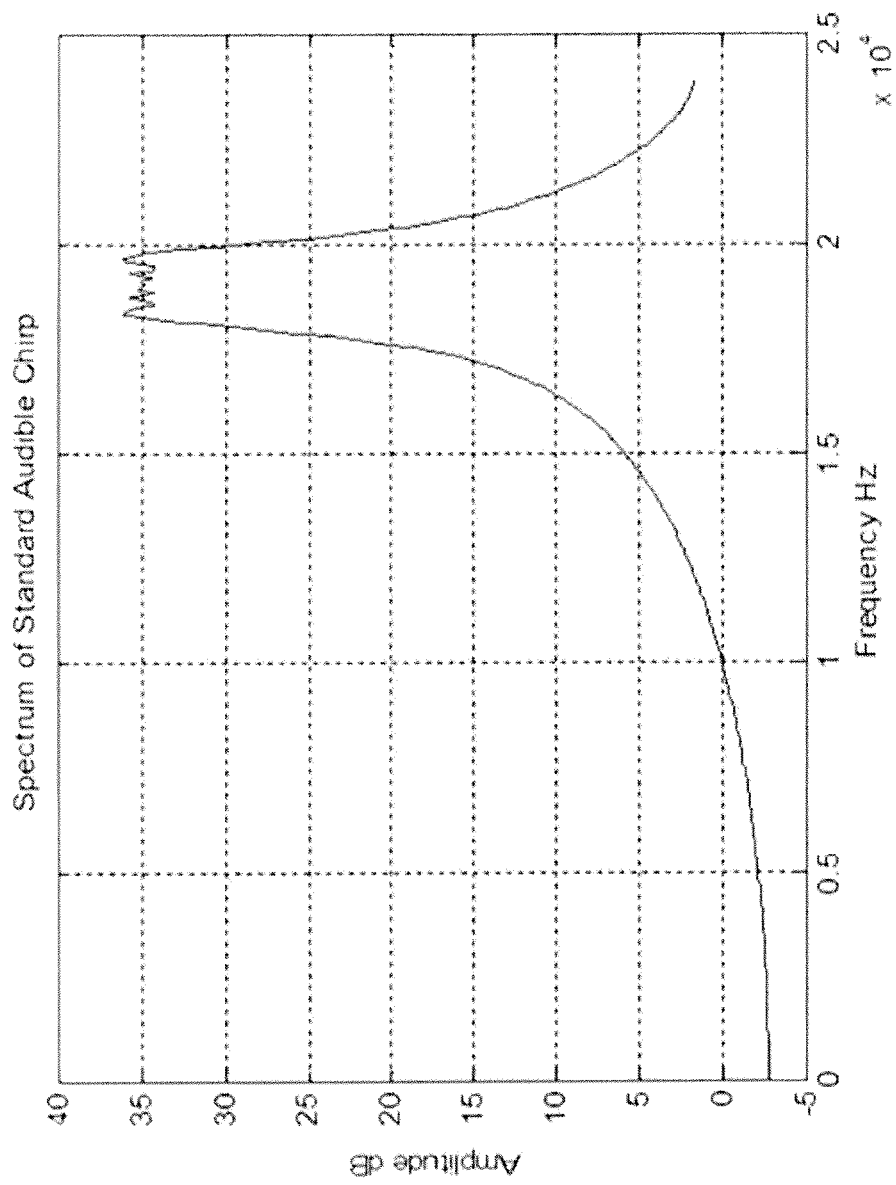

FIG. 15 illustrates an example of an audible version of an FMCW ramp sequence. FIG. 15(a) illustrates a standard chirp in a graph showing amplitude versus time. FIG. 15(b) shows a spectrogram of this standard audible chirp, while FIG. 15(c) illustrates a frequency spectrum of a standard audio chirp.

Figure 16A:
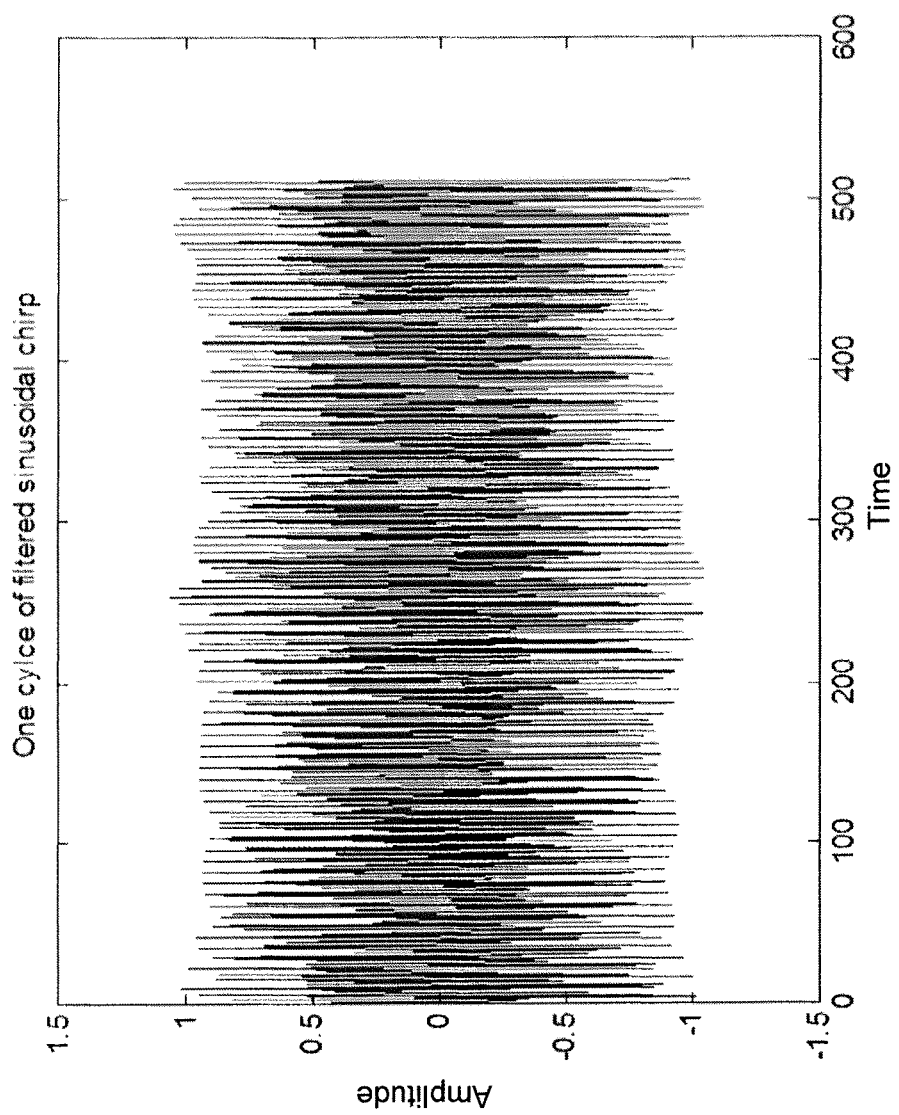
FIGS. 16A, 16B and 16C illustrate signal characteristics of an example of an FMCW sinusoidal profile.
Figure 16B:
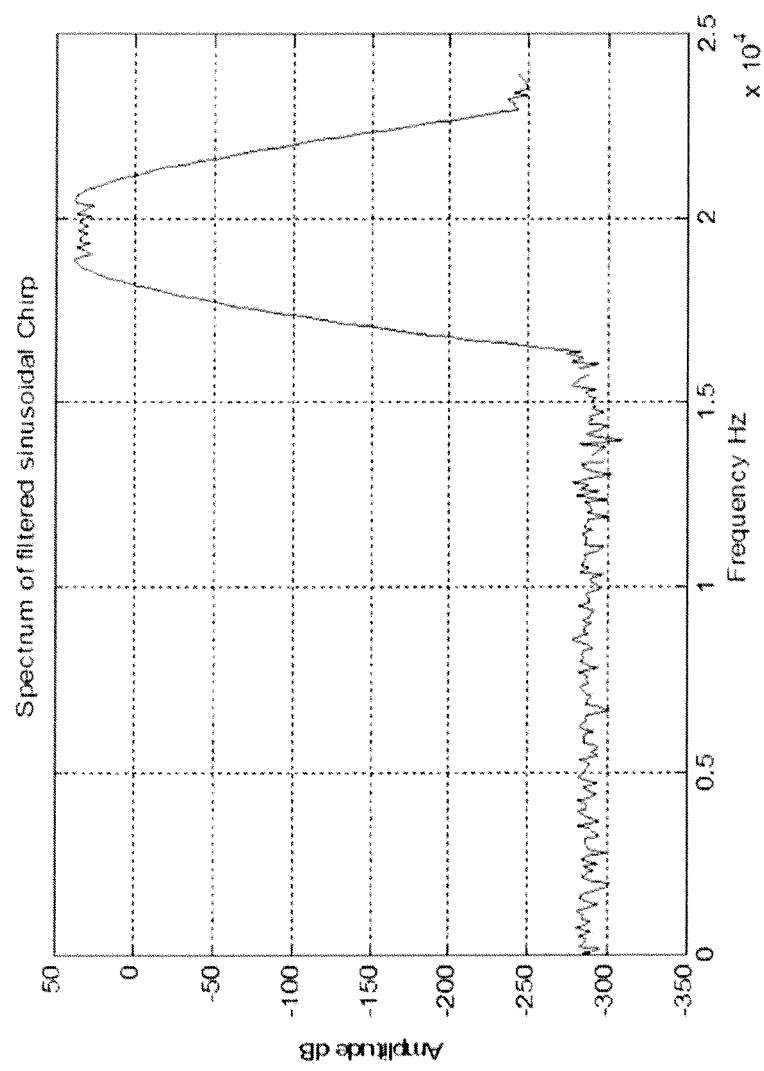
Figure 16C:
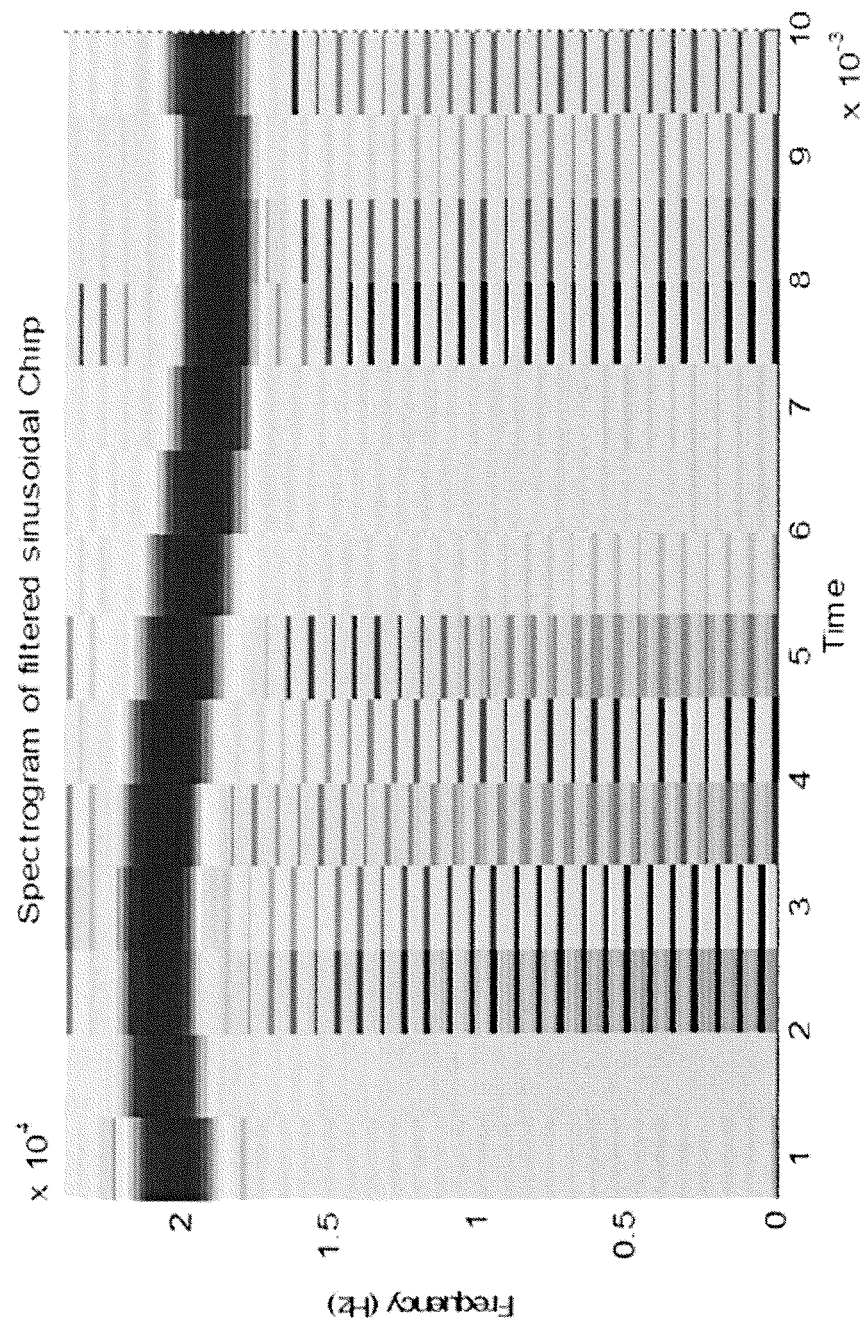

As described above, an FMCW tone can also use a sinusoidal profile rather than a ramp. FIG. 16 illustrates an example of an FMCW sinusoidal profile with high pass filtering applied. FIG. 16A shows the signal amplitude verses time. FIG. 16 B shows a frequency spectrum of the signal. FIG. 16C shows a spectrogram of signal. The following example uses a start frequency of 18 kHz and end frequency of 20 kHz. A "chirp" of 512 samples is generated with a sinusoidal profile. The middle frequency is 19,687.5 Hz and the deviation is +/−1,000 Hz. A sequence of these chirps has continuous phase across chirp boundaries which helps to make the sequence inaudible. A high pass filter can optionally be applied to the resulting sequence; however, it should be noted that this operation can give rise to phase discontinuities, which paradoxically make the signal more audible rather than, as desired, less audible. The FFT of the shifted receive signal is multiplied by the conjugate of the FFT of the transmit sequence. The phase angle is extracted and unwrapped. The best fitting straight line is found.

As noted, if the sinusoidal signal had to be filtered in order to make it inaudible, this is not ideal as it can distort the phase information. This may be due to phase discontinuity between sweeps. Therefore, an inaudible FMCW sequence using a triangular waveform may be used.

A triangular waveform signal that is a phase continuous waveform can be produced so that clicks are not produced by a speaker(s) that generate(s) the waveform. Despite being continuous across sweeps, phase differences at the beginning of each sweep may be present. The equations may be modified to ensure the phase at the beginning of the next sweep started at a multiple of $2\pi$, allowing looping of a single section of the waveform in a phase continuous manner.

A similar approach can be applied to ramp chirp signals, although the frequency jump discontinuity from 20 kHz to 18 kHz (assuming a chirp of 18 kHz to 20 kHz) can stress the amplifier and loudspeaker in commodity smart devices. The triangular waveform offers more information than the ramp due to addition of the down-sweep, and the triangular waveform's more "gentle" change in frequency should be less harmful to the phones hardware than the discontinuous jump of the ramp.

Example equations that may be implemented in a signal generation module for generating this phase continuous triangular waveform are as follows. The phase of the triangular chirp can be calculated for both up and down sweep and for time index n from the following closed expressions:

$$triPhase_{up}(n) = \frac{2\pi}{f_s}\left(\frac{f_2 - f_1}{N-2}n^2 + \frac{f_2 + (N-3)f_1}{N-2}n\right)$$

$$triPhase_{dn}(n) = \frac{2\pi}{f_s}\left(\frac{f_1 - f_2}{N-2}n^2 + \frac{(N-3)f_2 + f_1}{N-2}n\right) + triPhase_{up}\left(\frac{N}{2} - 1\right) + \frac{2\pi f_2}{f_s}$$

where
$f_s$ is the sample rate
$f_1$, $f_2$ are the lower and upper frequencies, respectively
N is the total number of samples in the up and down sweeps, $$\frac{N}{2}$$

samples per sweep (assuming even N).

The final phase at the end of the down sweep is given by $$triPhaseFinal = \frac{\pi}{f_s}(Nf_2 + (N-2)f_1)$$

To bring the sin of the phase back around zero at the start of the next sweep we provide:

$$triPhaseStart = triPhaseFinal + \frac{2\pi f_1}{f_s} = 2\pi m,$$

$$\Rightarrow N(f_2 + f_1) = 2mf_s$$

For example, assume N and $f_2$ are fixed. We therefore select m to bring $f_1$ as close to 18 kHz a possible:

$$f_1 = \frac{2mf_s}{N} - f_2$$

For N=1024 and $f_2$=20 kHz, m=406, then $f_1$=18,062.5 kHz

The demodulation of this triangular waveform can be considered as either demodulating the triangular up and down sweep individually, or by processing the up and down sweep simultaneously, or indeed by processing frames of multiple triangular sweeps. It is noted that the case of just processing the up-sweep is equivalent to processing a single frame of a ramp (sawtooth).

Figure 17:
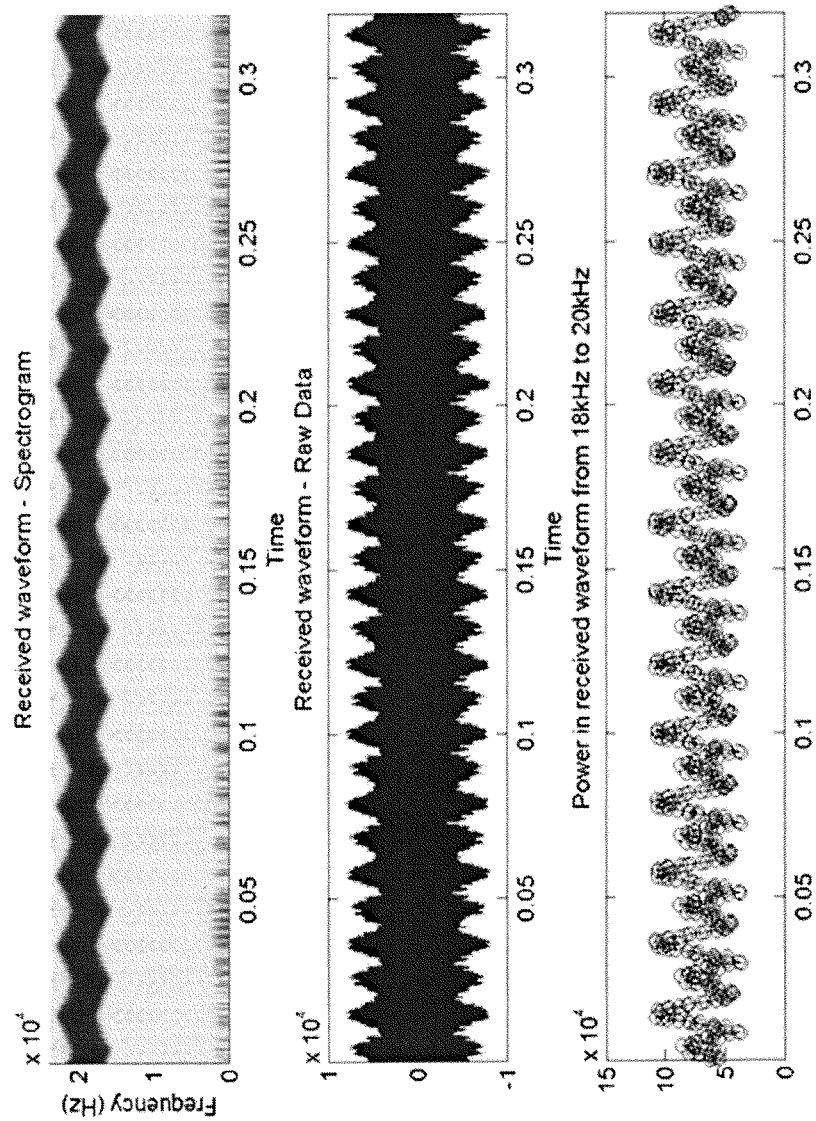
FIG. 17 illustrates signal characteristics of an example sound signal (e.g., inaudible sound) in the form of a triangular waveform.
Figure 18A:
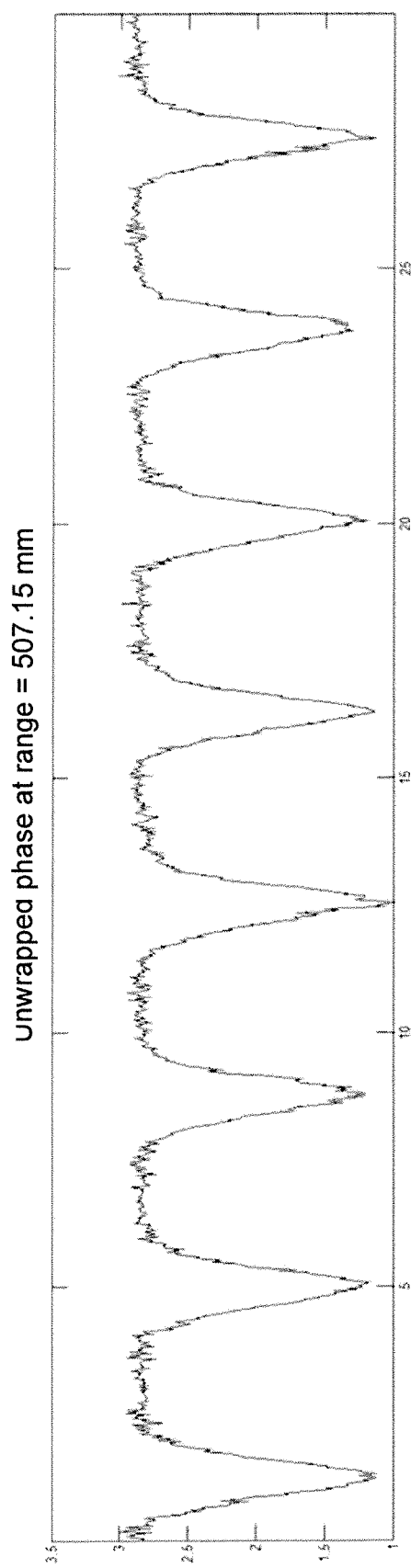
FIGS. 18A and 18B illustrate demodulation of a detected breathing waveform from the inaudible triangle emitted by a smart device's loudspeaker of FIG. 17 with up ramp processing shown in FIG. 18A and down ramp processing shown in FIG. 18B.
Figure 18B:
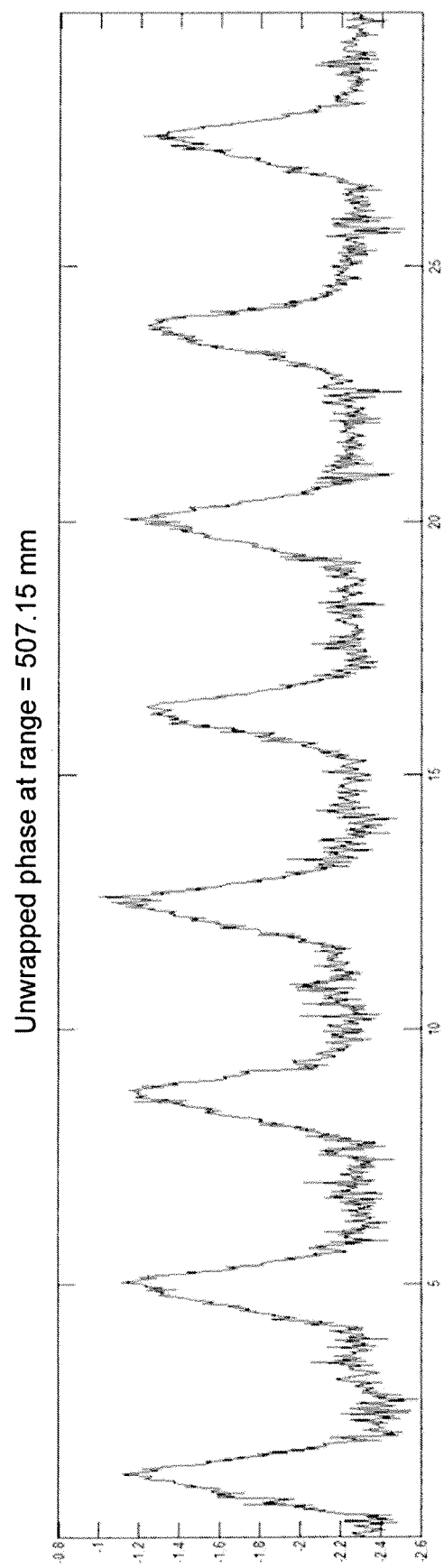

By using the up and/or down sweep, such as in respiration sensing, inspiration can be separated from expiratory parts of the breath (i.e., know at a point in time if inspiration or expiration is occurring). Examples of triangular signals are shown in FIG. 17 and the demodulation of a detected breathing waveform are shown in FIGS. 18A and 18B. As shown in FIG. 17, a smart device microphone has recorded the inaudible triangle emitted by the same smart device's loudspeaker. In FIG. 18A, a graph shows a result of demodulation of a reflection of the triangular signal in relation to the up sweep of the signal, showing the extracted breathing waveform at 50.7 cm. FIG. 18B is a graph that shows a result of demodulation of a reflection of the triangular signal in relation to the down sweep of the signal, illustrating the extracted breathing waveform at 50.7 cm. As shown in these figures, the recovered signal of FIG. 18B appears flipped upside down with respect to the demodulated unwrapped signal of the corresponding up-sweep due to the difference in phase.

An asymmetric "triangular" ramp may also be considered in place of the symmetric triangular ramp, where the upsweep is longer duration that the downsweep (or vice versa). In this case, the shorter duration is (a) to maintain inaudibility that could be compromised by the transient in say an upsweep-only ramp, and (b) provide a reference point in the signal. The demodulation is performed on the longer upsweep (as it would be for a sawtooth ramp with a quiet period (but instead the "quiet period" is the shorter duration downsweep); this potentially allows a reduction in processing load (if required), while maximizing the Tx signal used, and maintaining an inaudible, phase continuous Tx signal.

5.1.2.2.2.6 FMCW Demodulation

Figure 19:
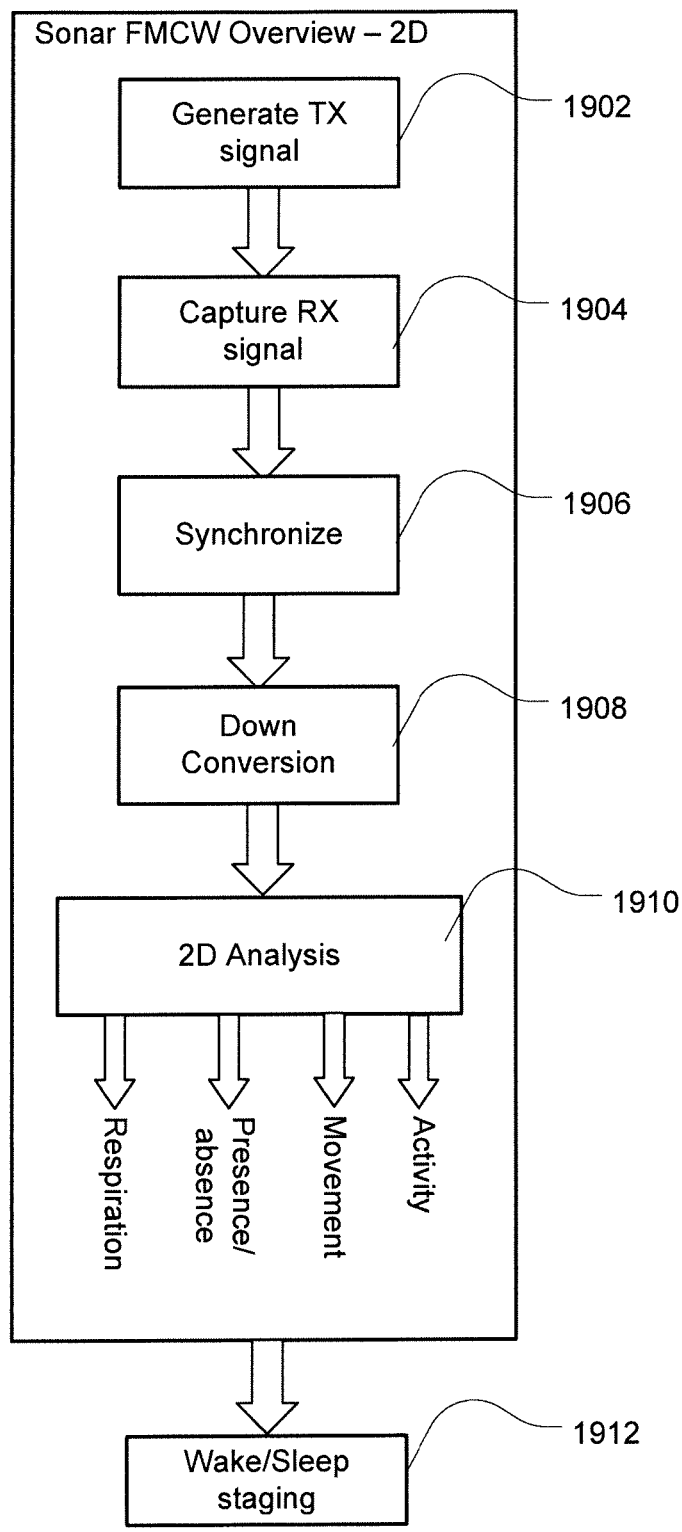
FIG. 19 illustrates an exemplar methodology of an FMCW processing flow operator/module, including "2D" (two dimensional) signal processing.

An example flow of a SONAR FMCW processing methodology is shown in FIG. 19. This illustrates blocks or modules providing front end transmit signal generation at 1902, signal reception at 1904, synchronization at 1906, down conversion at 1908, "2D" analysis at 1910 including generation of signals or data representing any one or more of estimation of activity, movement, presence/absence and respiration. From these data/signals, wake and/or sleep staging at 1912 may be provided.

It is possible to correlate the transmitted chirp with the received signal, particularly for checking synchronization in the module at 1906. As an example, the resulting narrow pulse may be useful for determining fine detail due to the sharp peak after the correlation operation. There is generally a reciprocal relationship between the width of a signals spectrum and the width of the correlation function; e.g., the relatively wide FMCW signal correlated with an FMCW template gives rise to a narrow correlation peak. As an aside, correlating a standard chirp with the response at the receiver, provides an estimate of the echo impulse response.

In FMCW, the system effectively considers the ensemble of all responses across the frequency range, as the "strongest" overall response (e.g., while some frequencies in a chirp may encounter severe fading, others may provide a good response, and so the system considers the ensemble).

An example methodology of one or more processors, such as in a mobile device, to recover the baseband signal (e.g., gross body movement or breathing) as an FMCW system is as follows. According to some aspects of the disclosure, a chirp sequence may be transmitted such as using a FMCW transmission generation module at 1902 operating one or more speaker(s). The chirp sequence may be, for example, an inaudible triangular acoustic signal. An incoming received signal, such as one received by a reception module at 1904 operating with one or more microphones, may be synchronized with the transmit signal using, for example, the peak correlation described above. Continuous resynchronization checking on a chirp or block (e.g., of several chirps) basis may be carried out such as with a synchronization module at 1906. A mixing operation, such as by multiplication or summing, may then be performed for demodulation such as with down conversion module at 1908, wherein one or more sweeps of the received signal may be multiplied by one or more sweeps of the transmit signal. This produces frequencies at the sum and difference of the transmit and received frequencies.

One example of a signal transmitted from the phone using a transmission module at 1902 is a triangular chirp that is phase continuous (to ensure inaudibility) and designed to enable looping sound data by a processor controlled speaker(s) according to a module running on a computing device (e.g., mobile device). An exemplar triangular chirp uses 1500 samples at 48 kHz for both the up and down sweep. This gives an up-sweep time of 31.25 ms (which may be the same for the down-sweep) and provides a baseband sample rate (as opposed to audio sample rate) of 32 Hz if both up and down sweep are used consecutively or 16 Hz if they are average (or only alternate sweeps used).

Where more than one sweep is used (e.g., 4 sweeps), the calculation may be repeated on a block basis by moving one sweep per iteration (i.e., introducing an overlap). In this case, the peaks of the correlation can optionally be estimated by extracting the envelope of the correlation, using methods such as filtering, max hold, or other methods such as the Hilbert transform; outliers can also be removed—e.g., by removing those falling outside one-standard deviation from the average of the relative peak locations. It is possible to use the mode of the relative peak locations (with outliers removed) to determine the starting index when extracting each sweep of the received waveform.

The reason that a correlation metric may sometimes be lower than others could be due to intermittent unwanted signal processing impacting the transmitted waveform (causing a diminution or "dipping" of the chirp), or indeed loud sounds in the room environment causing the signal to be "drowned out" for a short time.

A more fine-grained phase level synchronization can be performed (albeit with greater computational complexity) with a synchronization module at 1906 by checking correlation against a template shifted in phase in degree increments up to a maximum of 360 degrees. This estimates the phase level offset.

Unless the timing of the system is very accurately controlled (i.e., having knowledge of delay in the system down to a sample level), a synchronization step is desirable to ensure the demodulation works correctly, and does not produce a noisy or erroneous output.

Figure 20:
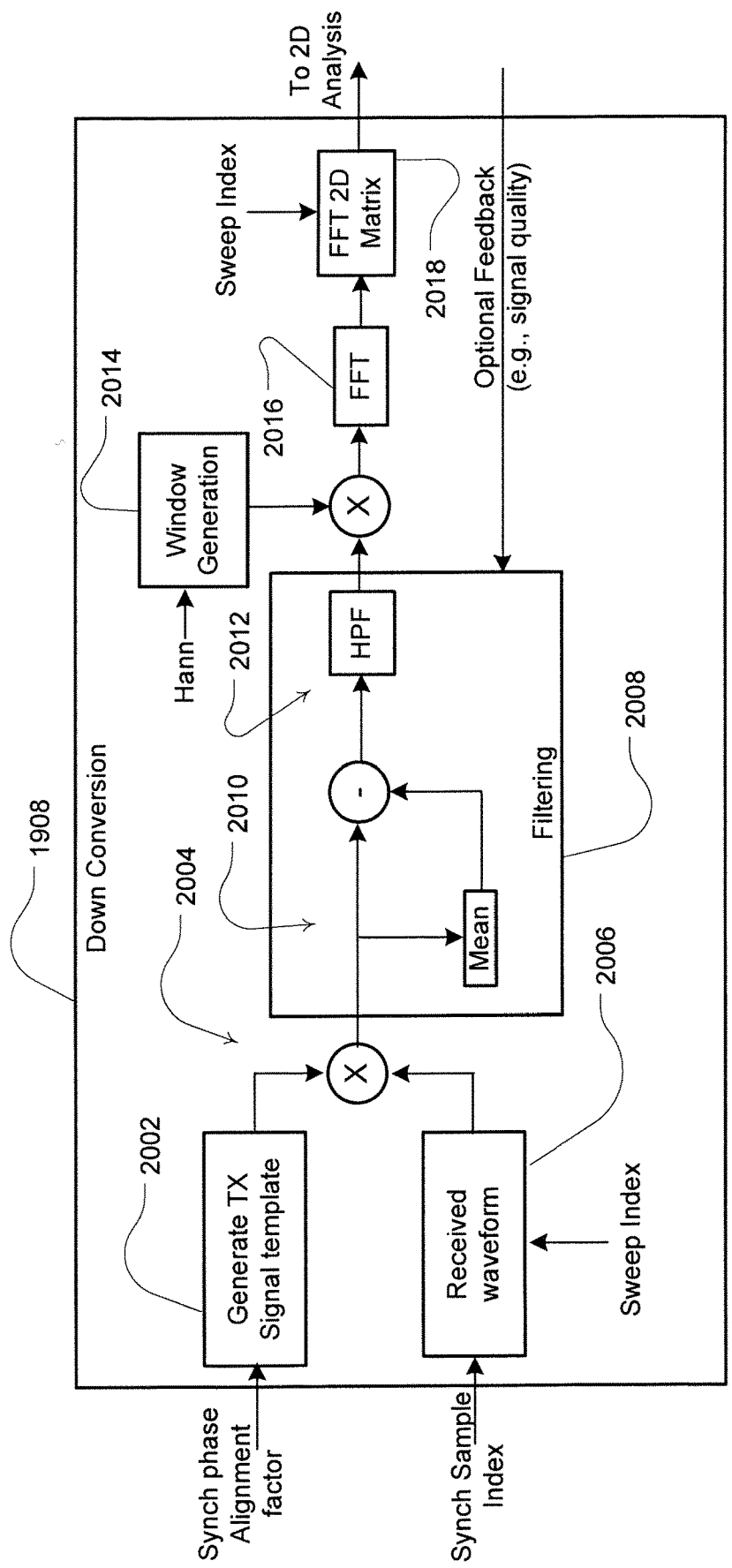
FIG. 20 illustrates an exemplar methodology of a Down Conversion operator/module, part of an FMCW processing flow of FIG. 19.

As previously noted, the down conversion processing in a module at 1908 may produce a baseband signal for analysis. With the transmit and received data synchronized, the down conversion can now be carried out. This module processes synchronized transmit and receive signals (produced sound and reflected sound) with various submodules or processes to extract a "beat" signal. One example of this audio processing is illustrated in FIG. 20; in this, I and Q transmit signals, with a phase offset determined using the fine-grained synchronization method may be generated for mixing. A "nested loop" can be repeated at 2002 used for the mixing such as in a module or processing at 2004: the outer loop iterates over every sweep in the current received waveform held in memory and applied by the access process at 2006 to the mixing at 2004 (each up and down chirp are considered a separate sweep); the inner loop then iterates for the I channel first followed by the Q channel.

Another example of the system, not shown in FIG. 20, optionally buffers a number of received sweeps, calculates the median, and provides a moving median figure of the buffer containing the multiple sweeps. This median value is then subtracted from the current sweep in order to provide another method of detrending the signal.

For each sweep (either up or down) the relevant portion of the received waveform is extracted (using sync sample index as reference) in order to be mixed at 2004 with the phase shifted transmit chirp. With both transmit and receive section generated, the waveforms are mixed (i.e., multiplied) together at 2004. It can be seen for example that for the down-sweep it is possible to mix the received down sweep with TX down-sweep, a flipped received down-sweep with the TX up-sweep or a flipped received down-sweep with a flipped TX down-sweep.

Output of the mixing operation (e.g., multiplication of the received waveform by the reference aligned waveform (e.g., reference chirp)) may be low-pass filtered to remove higher sum frequencies such as in a filtering process or module at 2008. As an example, an implementation may use a triangular chirp 18-20-18 kHz, with a sampling rate of 48 kHz; for such frequency band, the higher sum frequencies in the mixing operation are actually under-sampled, and produce an aliased component at about 11-12 kHz (for Fs=48 kHz, the sum is around 36 kHz). The low pass filter may be configured to ensure that this aliased component is removed if it occurs in a particular system realization. The components of the remaining signal will depend on whether the target is static or moving. Assuming an oscillating target at a given distance (e.g., a breathing signal), the signal will contain a "beat" signal and a Doppler component. The beat signal is due to the difference in frequency position of the transmit and received sweeps caused by the time delayed reflection from the target. The Doppler is a frequency shift cause by the moving target. Ideally, this beat should be calculated by only selecting the section of the sweep from the point the received signal arrives in, to the end of the transmitted sweep. However, this is difficult to do in practice for a complex target such as a person. Thus, it is possible to use the whole sweep. According to some aspects of the disclosure, a more advanced system may utilize an adaptive algorithm that uses the fact that once the subject location is identified clearly, the appropriate portion of the sweep is taken, further increasing the system accuracy.

In some cases, the mixed signal may optionally have the mean (average) removed (mean detrended) such as in the detrending processing at 2010 and/or be high pass filtered, such as in the HPF processing at 2012, to remove unwanted components that could ultimately manifest in the baseband. Other detrending operations may be applied to the mixed signal such as linear detrending, median detrending etc. The level of filtering applied at 2008 can depend on the quality of the transmit signal, the strength of the echoes, number of interferers in the environment, static/multipath reflections and so forth. For higher quality conditions, less filtering may be applied, as the low frequency envelope of the receive signal can contain respiration and other movement information (as well as in the eventual demodulated baseband signals). For low quality, more challenging conditions, noise in the mixed signal can be significant, and more filtering is desirable. Indications of actual signal quality (e.g., of respiration signal quality) can be fed back to these filtering processes/modules, as a feedback signal/data, to select an appropriate level of filtering at this filtering module stage at 2008.

Two dimensional (2D) analysis at 1910 of the complex FFT matrix subsequent to down conversion at 1908, is used in order to extract respiration, presence/absence, gross body movement and activity. Thus, the down converter may produce a frequency domain transformation matrix. For this type of process, the blocks of mixed (and filtered) signal are windowed (e.g., using a Hanning window module at 2014. Then a Fourier transform (such as an fast Fourier transform or FFT) at 2016 is carried out to estimate and produce a "2D" matrix 2018. Each row is the FFT of a sweep and each column is an FFT bin. It is these FFT bins that translate into range, and are therefore referred to as "range bins." The matrix, such as a set of quadrature matrices with each matrix based on either I channel or Q channel information, is then processed by the 2D analysis module.

Figure 21:
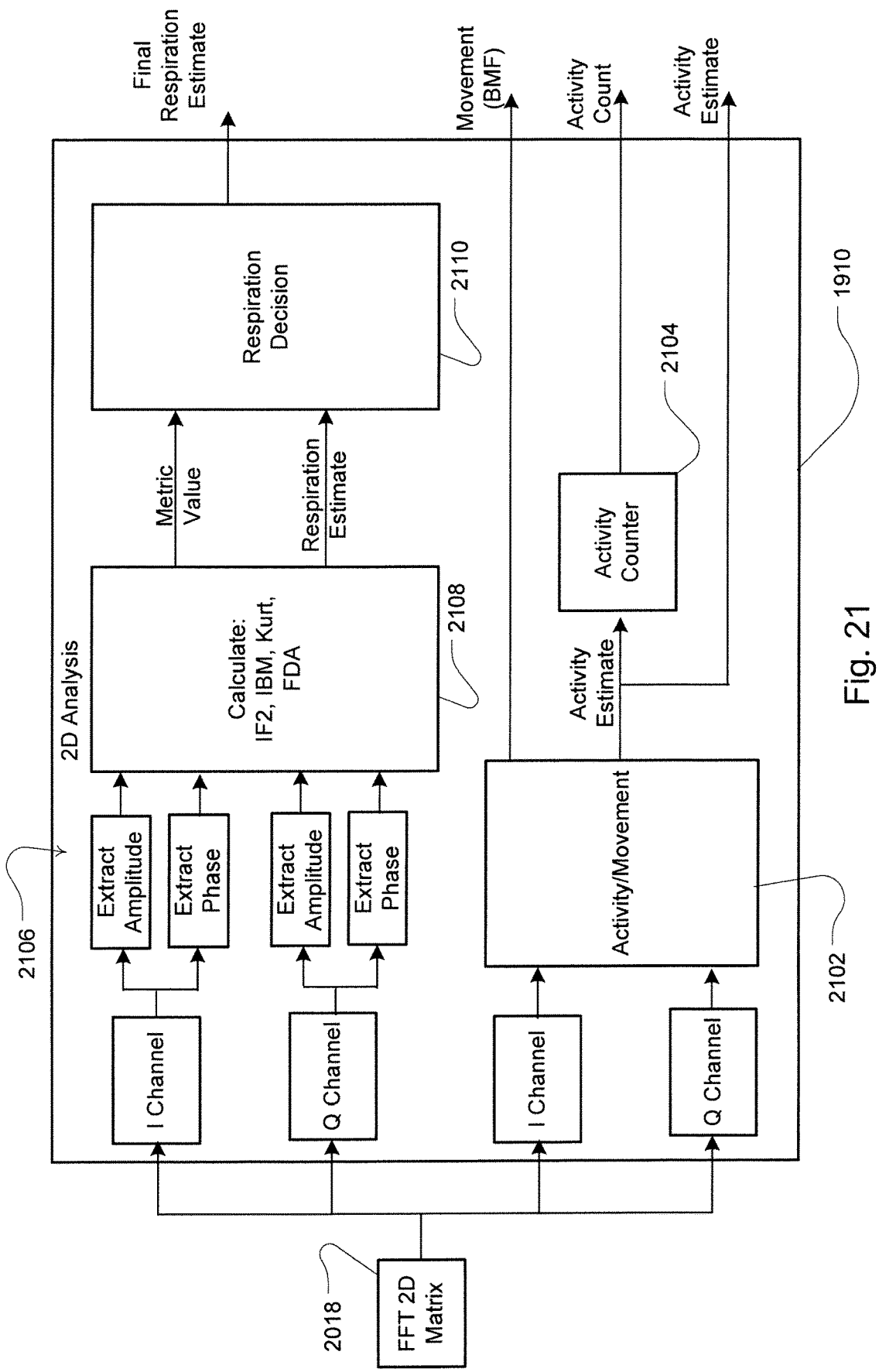
FIG. 21 illustrates an exemplar methodology of a 2D Analysis operator/module, which may be part of an FMCW processing flow of FIG. 19.

An example of such processing is illustrated in reference to the modules shown in FIG. 21. As part of this 2D analysis at 1910, body (including limb) movement and activity detection can be carried out on these data. Movement and activity estimation of the processing module(s) at 2102 extracts information about a subject's movement and activity from analysis of the complex (I+jQ) mixed signal in the frequency domain. It may be configured to operate on the basis that whole body (e.g., rolling, or movement of limbs) movement is uncorrelated and grossly larger than chest displacement during respiration. Independent (or dependent on) this movement processing, multiple signal quality values are calculated for each range bin. These signal quality values are calculated for both amplitude and unwrapped phase across both the I and Q channels.

The processing at 2102 produces an "activity estimate" signal and a movement signal (e.g., body movement flag.) The "body movement flag" (BMF) produced by the activity/ movement processing at 2102 is a binary flag indicating if movement has occurred (output at 1 Hz), whereas the "activity count"—, produced in conjunction with counter process module at 2104, is a measure of activity between 0 and 30 for each epoch (output at ⅟30 s). In other words, the "activity count" variable captures the amount (severity) and duration of the body movement in a defined period of a 30 seconds block (updating every 30 sec), whereas the "movement" flag is a simple yes/no to movement occurring that is updated every second. The raw "activity estimate" that is used for generation of the activity count, is a measure estimated on the basis that the mixed chirp signals are correlated with each other during non-movement and uncorrelated during movement periods. As the mixed sweeps are a complex frequency domain representation, a modulus or absolute value of the signal can be taken before analysis. Pearson correlation is calculated on a series of mixed up-sweeps spaced 4 chirps apart over the range bins of interest. This spacing corresponds to 125 ms for a 1500 sample transmit waveform at 48 kHz. The spacing of chirps determines the velocity profile that is being inspected, and can be adjusted as needed. This correlation output is inverted, e.g., by subtracting from 1, and so a decrease in correlation relates to an increase in the metric. The maximum value for each second is calculated and then passed through a short 3-tap FIR (finite impulse response) boxcar mean filter. With certain devices, the response to movement that is calculated using this approach can be non-linear in nature. In such a case, the metric can be re-mapped via a natural log function. The signal is then de-trended by subtracting the minimum value observed over the previous N seconds (corresponding to the maximum observed correlation) and passed into a logistic regression model with a single weight and bias term. This generates the 1 Hz raw activity estimate signal. The binary movement flag is generated by applying a threshold to the raw activity estimate signal. The activity count is generated by comparing the 1 Hz raw activity estimate, above a threshold, to a non-linear mapping table where a value is chosen from 0 to 2.5 for each second. This is then summed over a 30 second period and limited at a value of 30 to generate an activity count for each epoch.

Therefore, a one second (1 Hz) motion flag has been created, along with an activity intensity estimate, as well as an associated activity count to a max value of 30 (summation of activity in a 30 sec epoch) in relation to the processes of the activity/movement module at 2012 and the activity counter at 2104.

Another aspect of the 2D processing at 1910 is the calculation of the subject's distance from the sensor (or several distances in the case of two or more subjects in range of the sensor). This may be implemented with a range bin selection algorithm that processes the resulting two dimensional (2D) matrix 2018 to yield a 1D matrix (or matrices) at the bin(s) of interest. Although not shown in FIG. 21, the output of a module for such a selection process may inform the processing modules of the 2D analysis, including for example, any of the extraction processing at 2016, the calculation processing at 2108 and the respiration decision processing at 2110. In this regard, unwrapping the phase at the resulting beat frequency will return the desired oscillating movement of the target (assuming no phase unwrapping problems occur). Optional phase unwrapping error detection (and potential correction) may be performed to mitigate possible jump discontinuities in the unwrapped signal due to gross movements. However, these "errors" can actually yield useful information, i.e., they may be used to detect movements (usually larger movements such as gross motion) in the signal. If the input signals to phase unwrapping are very low amplitude noise only, a flag may optionally be set for the duration of this 'below threshold' signal as the unwrapping might be invalid.

The start time and end time, as well as position (i.e., range) of a movement can be detected in the 2D unwrapped phase matrix through various methods; for example, this can be achieved using 2D envelope extraction and normalization, followed by thresholding. The time scale of the normalization is configured to be sufficiently large to exclude the variation in phase due to breathing-like movements (e.g., >>k*12 seconds for a minimum breathing rate defined as 5 bpm). The detection of such movements can be used as an input trigger to the bin selection process; for example, the bin selection algorithm may "lock" to a prior range bin during the movement period, and hold that bin, until a valid breathing signal is next detected in or near that bin. This can reduce the computational overhead in the case where a subject is breathing quietly, moves in bed, and then lies quietly; they are still seen in the same range bin. Thus, start and/or end position of the detected movement can be used to limit the search range for bin selection. This can apply to multiple subject monitoring use cases as well (e.g., where two subjects in bed are simultaneously monitored, the movement of one subject may smear the breathing signal of the other, but such a lock-in bin selection can aid the recovery of the valid range bin (and this respiration signal extraction) of both subjects-even during the large movement of the one subject.

This approach yields the signal produced by the phase-unwrapped oscillation. The complex output yields a demodulated baseband IQ signal containing body motion of a living person or animal (including breathing) data for subsequent processing. For the example of a triangular Tx waveform, the system may process the linear up-sweep and down-sweep separately, and consider as a separate IQ pair (e.g., to increase SNR, and/or to separate inspiration from expiration breaths). In some realizations, optionally the beat frequencies from each (up-sweep and down-sweep) may be processed in order to average out possible coupling effect in the Doppler signals, or in order to produce a better range estimate.

A baseband SNR metric may be configured to compare a respiratory noise band of 0.125-0.5 Hz (equivalent to 7.5 br/min to 30 br/min—although this might be widened to around 5-40 br/min depending on the use case—i.e., the primary breathing signal content) to a movement noise band of 4-8 Hz (i.e., a band primarily containing movement other than breathing), where the baseband signal(s) are sampled at 16 Hz or above. Baseband content below 0.083 Hz (equivalent to 5 breaths/min) may be removed by high pass filtering. Heart rate information may be contained in the band of approximately 0.17-3.3 Hz (equivalent to 25 beats per minute to 200 beats per minute).

During SONAR FMCW processing, optionally the difference between beat estimates may be taken in order to exclude (remove) static signal components, i.e., by subtracting adjacent estimates.

The range bin selection algorithm in this approach may be configured to track the range bin corresponding to the location of one or more subjects in the range of the sensor. Depending on the data supplied by the user on positioning, this may require a partial or complete search of the possible range bins. For example, if the user notes how far they sleep (or are sitting) with respect to the device, the search range can be narrowed. Typically, a block or epoch of data under consideration might be 30 sec long and not overlapping (i.e., one range bin per epoch). Other realizations might use longer epoch lengths, and employ overlapping (i.e., multiple range bin estimates per epoch).

As the detection of a valid breathing rate (or probability of a breathing rate over a defined threshold) is used, this limits the smallest possible window length as at least one breathing cycle should be able to be contained in the epoch (e.g., a very slow breathing rate of 5 breaths per minute implies one breath every 12 sec). At the upper end of breathing rates, 45-50 br/min is a typical limit. Thus, when using a spectral estimate of the epoch (e.g., removing the mean, optionally windowing, and then carrying out an FFT), the peak(s) relating in the desired breathing band (e.g., 5-45 br/min) are extracted, and the power in the band is compared to the full signal power. The relative power of the maximal peak (or maximal peak-to-mean ratio) across bands is compared to a threshold to determine if a candidate breathing frequency is present. In some circumstances, several candidate bins with similar breathing frequency may be found. These can occur due to reflections in the room, giving rise to apparent breathing at multiple ranges (this could also be related to FFT side lobes).

Processing of the triangular waveform can help mitigate such uncertainty in range (e.g., due to Doppler coupling), although if a reflection contains better signal than the direct path for a period of time, the system can choose to use this. Where the user has a comforter/duvet, and the room contains soft furnishings (including say a bed and curtains), it is less likely that non-direct reflections will yield a higher signal to noise ratio than the direct component. As the primary signal may be a reflection from the duvet surface, this may appear slightly closer than the chest of the person when considering the actual estimated range.

It can be seen that knowledge of a prior epoch's estimate range bin can be used to inform subsequent range bin searches, in an effort to reduce processing time. For a system that does not require near real-time (epoch by epoch) analysis, longer timescales can be considered.

1.1 Signal Quality

The signal quality of (i.e., the detection of, and related quality of) respiration, which may be considered by the filtering at 2008 of FIG. 20 as previously discussed, can be determined by way of various signal quality metrics calculated as part of the FFT 2D metrics, as shown in the calculator processing of the module at 2108 of FIG. 21. These metrices may also be considered in a respiration decision processing at 2110. Optionally, the 2D analysis processing at FIG. 21 may include processing or modules for determination of the absence/presence or sleep staging, which are based on the outputs and some intermediate values depicted.

With respect to the calculator processing at 2108, various metrics, such as for respiration estimation, may be determine. In the example, four metrics are indicated in FIG. 21:

1. "I2F"—In-band (I) squared over full band
2. "Ibm—In-band (I) only metric
3. "Kurt"—Metric based on the Kurtosis of the covariance
4. "Fda"—Frequency domain analysis
   1. "I2F"

The I2F metric may be calculated as follows (a similar approach applies for the Q (quadrature) channel which could be called inBandPwrQ):

$$I2F_I = \frac{inBandPwrI^2}{fullBandPwrI}$$

Where "inBandPwrI" is the total power from, for example, about 0.1 Hz to 0.6 Hz (e.g., within the respiration band of interest that has been selected) and "fullBandPwrI" is the total power outside of this range. This metric is founded on a broad assumption that full-band and the subset of in-band power is similar, and uses the full band power to estimate the noise in-band.

2. "Ibm"

The next metric does not make the same assumption as I2F, and provides an improved estimation of the signal and the noise in-band. It does this by finding the peak power in-band and then calculating the power around this (for example by taking three FFT bins each side of the peak). It then multiplies this signal power by the peak value itself divided by next peak value (for the case of a broadly sinusoidal type signal). Where respiration contains strong harmonics, the choice of bins can be reevaluated, such that the harmonics are not confused with noise components. The noise estimate then is everything outside the signal sub-band but still within the respiration band:

$$Ibm = \frac{PwrAroundPk * Pk/NxtPk}{inBandPwr - PwrAroundPk}$$

3. Kurtosis ("KURT")

Kurtosis provides a measure of "tailedness" of a distribution. This can provide a means of separating respiration from other non-respiration signals. For example, a signal quality output can be the inverse of the Kurtosis of the covariance of a DC-removed (using an IIR HPF) signal within a specified distance from the peak covariance. This metric is set to "invalid" under conditions of poor signal quality.

4. "Fda"

"Fda" (Frequency domain analysis) can be performed; such statistics can be calculated using 64 second overlapping data windows, with 1 second step length. Computations are causal, using retrospective data. The process may detect breathing rates within a certain breathing rate window. For example, breathing rates may be detected as described in International Application WO2015006364, the entire disclosure of which is incorporated herein by reference. For example, breathing rates may be detected within a rate window that amounts to 6 to 40 breaths per minute (bpm), corresponding to 0.1-0.67 Hz. This frequency band corresponds to realistic human breathing rates. Therefore, 'in-band' refers to the frequency range 0.1-0.67 Hz. Each 64 second window may contain 1024 (64 seconds at 16 Hz) data points. Hence, the algorithm calculates a 512 point (N/2) FFT for each (I and Q) data window. The results of these FFTs are used to calculate in-band spectral peak (which may subsequently be used to determine respiration rate), as described below. The in-band frequency range is used to calculate respiration rate for each 64 second window, as described below.

Other types of "Fda" analysis are presented below.

An alternative frequency band can also be considered for typical heart rate (e.g., where a HR of 45 beats per minute to 180 beats per minute corresponds to 0.75-3 Hz).

The spectral peak ratio may also be determined. The maximum in-band and outside-band peaks are identified, and used to calculate the spectral peak ratio. This may be understood to be the ratio of the maximum in-band peak, to the maximum outside-band peak.

The In-band variance may also be determined. The in-band variance quantifies the power in the frequency band. This can also be used for subsequent presence/absence detection in some cases.

The spectral peak is identified in the frequency band of interest through the implementation of a figure of merit which combines spectral power level at each bin, as well as distance from adjacent peaks and frequency of bin. The bin with the highest value for the above described figure of merit.

As part of the 2D analysis at 1910, the four metrics of the calculator processes at 2108 that have been outlined are calculated in order identify the one or more living persons in the range of the sensing vicinity of the mobile device, and track if they move to a different range (distance from sensor) or indeed leave the sensing space (go to bathroom) or return to the sensing space. This provides an input into absence/presence detection, as well as whether there are interferers within the sensing range. These values may then be evaluated further, such as in the processes of the respiration decision processing module at 2110 to produce a final respiration estimate for one or more subject monitored with the system.

1.2 Absence/Presence Estimation

Figure 22:
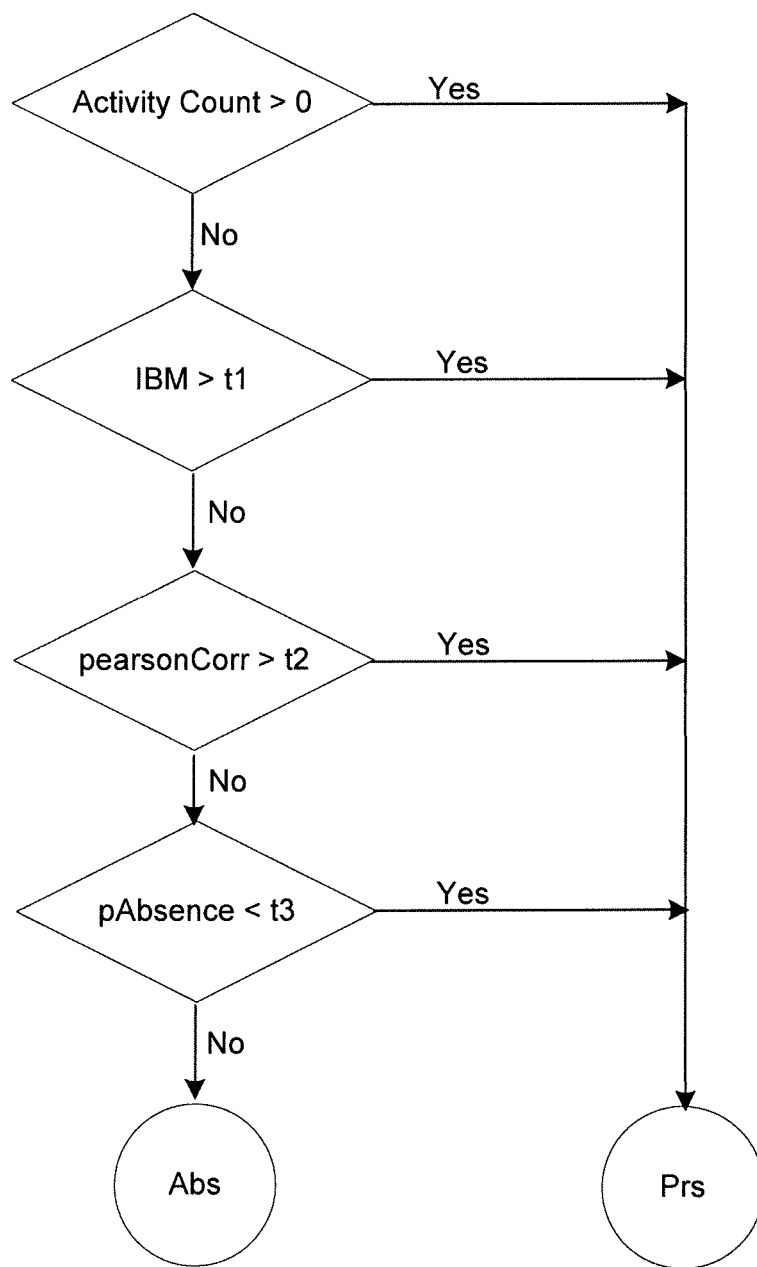
FIG. 22 illustrates a methodology for performing absence/presence detection by an absence/presence operator/module.

As illustrated in FIG. 19, the 2D analysis at 1910 may also provide processing for absence/presence estimating and an output indication of such an estimate. The detection of body movement of a person, and their respiratory parameters, can be used to assess a series of signals to determine whether a subject is absent or present from the sensor range. Depending on the signal quality detection, an "absence" can be triggered in 30 secs or less (and clearly distinguished from an apnea). Absence/presence detection can in in some versions be seen to include methodologies of feature extraction, and subsequent absence detection. An example flow diagram for such a process is shown in FIG. 22, which may use some of the calculated features/metrics/signals of the previously described processes at 1910, but may calculate others as described herein. Various types of features can be considered in deciding human presence (Prs) and human absence (Abs), including, for example one or more of:

1. A non-zero activity count
2. Pearson correlation coefficient between the current 2D signal (respiration vs range) and the previous window-limited to respiration and sensing-ranges of interest
3. The maximum of the I/Q Ibm quality metrics for the current respiration window
4. The maximum variance of I/Q respiration rate channels over a 60 sec window
5. The maximum variance of I/Q respiration rate channels over a 500 sec window The features are extracted from the current buffer and pre-processed by taking percentiles over the buffer length (e.g., over 60 s). These features are then combined into logistic regression model which outputs the probability of absence occurring for the current epoch. To limit false positives, this can for example be averaged over a short window (several epochs) to generate the final probability estimate. For periods of motion that are deemed related to body motion (motion of a person or animal), presence is asserted preferentially. In the illustrated example of FIG. 22, an activity count, IBM, pearson correlation coefficient and a probability of absence are compared to suitable thresholds to assess whether a person is present or absent. In this example, any one positive evaluation may be sufficient to determine presence whereas, each of the tests may be evaluated in the negative to determine absence.

Figure 23A:
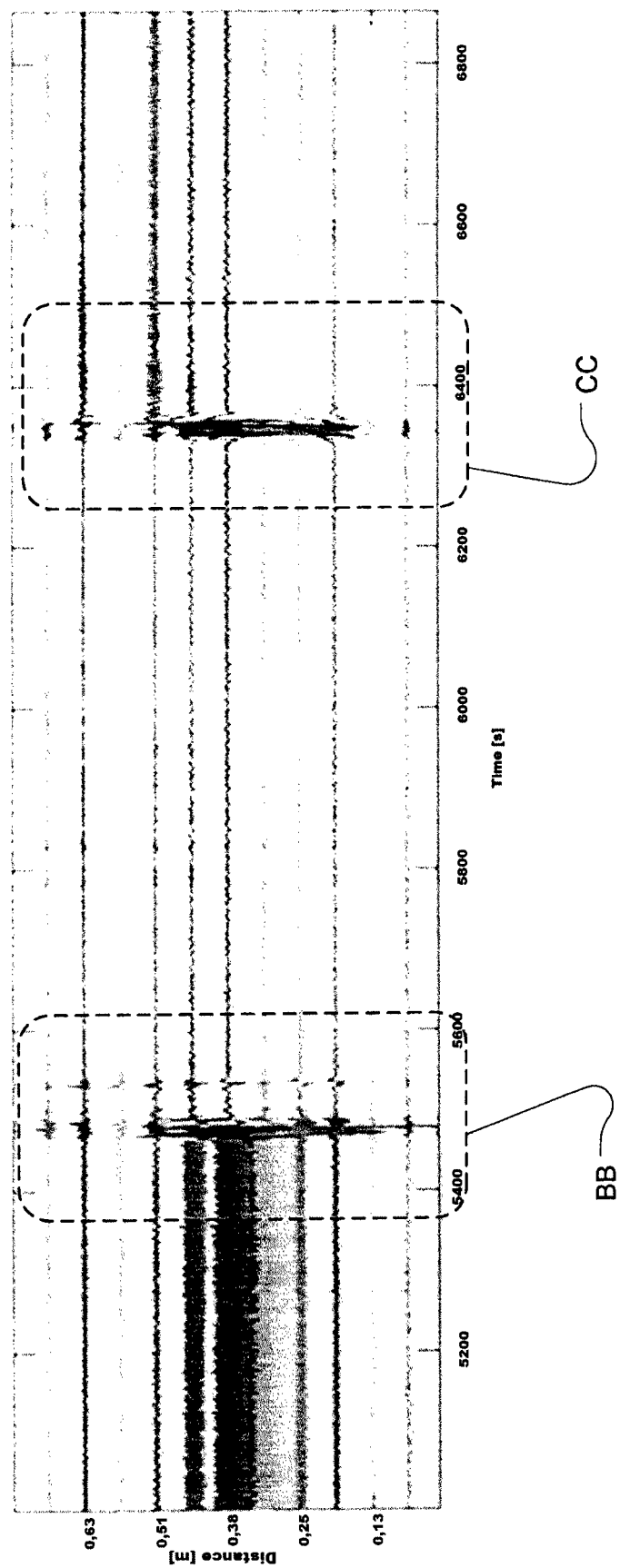
FIG. 23A shows several signals on a graph illustrating sensing operations at various detection ranges over time in a "2D" segment of data where a person moves out and into various sensing ranges of a device 100
Figure 23B:
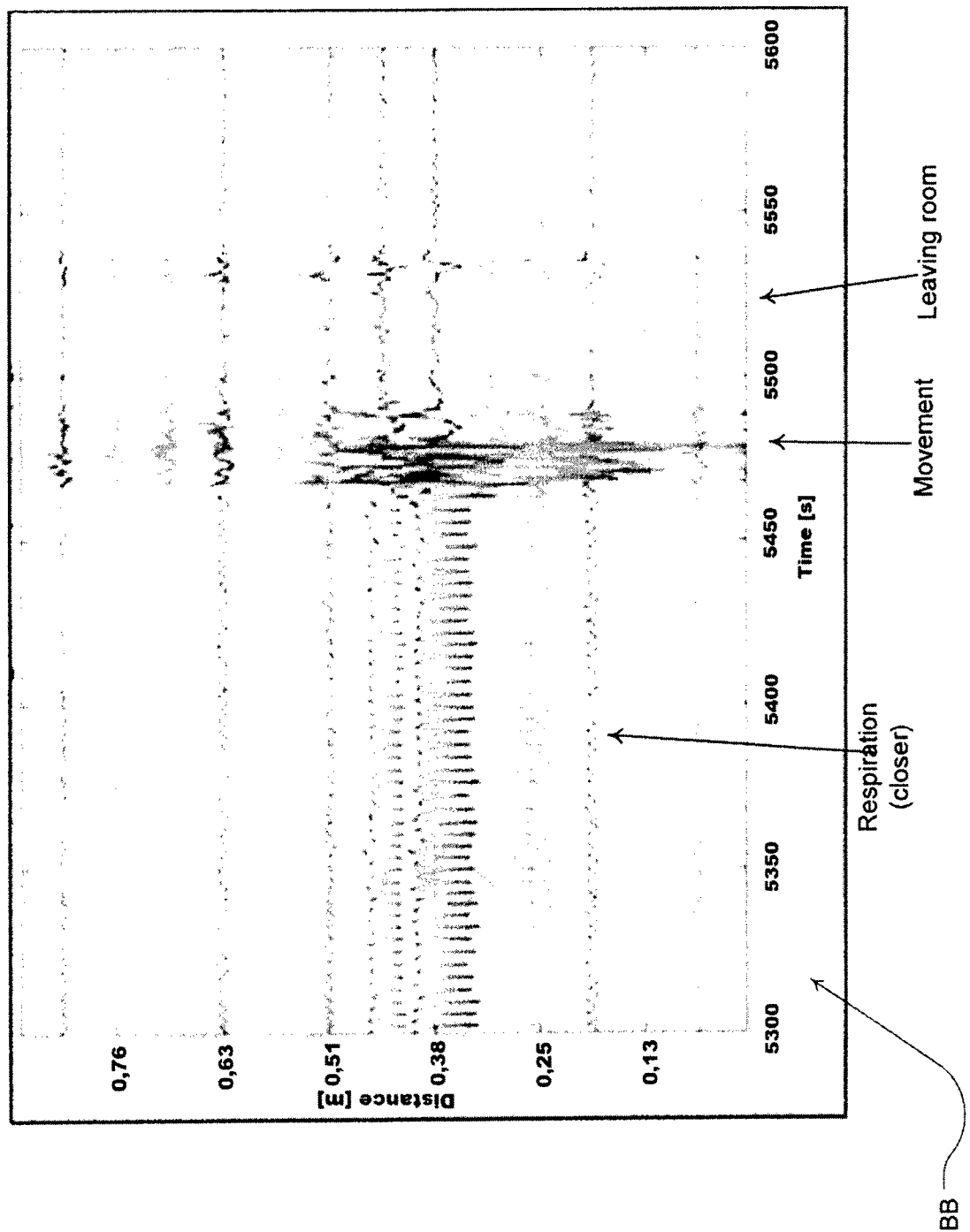
FIG. 23B is a portion of the signals graph of FIG. 23A showing area BB from FIG. 23A.

Taking a holistic system view, motion such as limb movement, rolling over in the end etc. will tend to disrupt the breathing signal, giving rise to higher frequency components (but may be separable when considering "2D" processing). FIGS. 23A, 23B and 23C provide an example of a segment of 2D data (upper panel), with two subsections (FIG. 23B and FIG. 23C) illustrating human activity in range of the acoustic sensing by a computing device with a microphone and speaker. Each trace or signal of the graph represents acoustic sensing of a different distance (range) from a mobile device having the application and modules described herein. In the figures, it is possible to visualize the respiration signal at several distances and movement across several ranges (distance) over time. For this example, a person is breathing at around 0.3 m from the mobile device, with their torso facing the mobile device. In the region BB and FIG. 23B, the person gets out of bed (gross body movement) to leave the vicinity of the sensing area (e.g., leaving the room to go to the bathroom). A while later, in relation of the region CC and FIG. 23C, the person returns to the vicinity of the sensing area or room, such as getting back in to bed (gross body movement) but slightly further away from the mobile device, now with their back facing the mobile device, (at around 0.5 m) and their respiration pattern is visible. At the simplest level when interpreting this figure, the lack of any respiratory trace or gross movement indicates a period of absence from the room.

Such movement detection can act as an input to sleep/wake processing, such as in a processing module at 1912 of FIG. 19, where sleep states may be estimated and/or wake or sleep designators may be generated. A large movement is also more likely to be a pre-cursor to a change in range bin selection (e.g., the user has just changed position). On the other hand, breathing may diminish or cease for periods of time in the case of SDB events detected from the respiratory parameter such as apneas or hypopneas, that can be recognized.

An alternative approach to processing the FMCW chirp signal may be applied if the velocity signal is required (which may depend on the end use-case). Using the alternate approach, the received signal may arrive as a delayed chirp, and an FFT operation may be performed. The signal may then be multiplied by its conjugate to cancel the signal and keep its phase shift. The best fitting straight line to the slope may then be determined using multiple linear regression.

Graphically, this method gives rise to an FMCW slope, when plotting the phase angle in radians against frequency. The slope finding operation needs to be robust to outliers. For a 10 ms FMCW chirp of 18 kHz to 20 kHz sequence, the effective range is 1.8 m, with a distance resolution of 7 mm. Overlapping FFT operations are used to estimate points on the recovered baseband signal.

In yet another approach to processing the FMCW signal directly as a one-dimensional signal, a comb filter may be applied to the synchronized signal (e.g., a block of 4 chirps). This is to remove the direct path from Tx to Rx (direct speaker to mic component) and static reflections (clutter). An FFT may then be carried out on the filtered signal, followed by a windowing operation. A second FFT may then be carried out, followed by maximal ratio combination.

The purpose of this processing is to detect the oscillations at the side lobes, and it outputs velocity rather than displacement. One advantage is that it estimates a 1D signal directly (without a complex bin selection step) and could optionally be used to estimate a likely range bin for the case of a single motion source (e.g., one person) in the field of the sensor.

It can also be seen that such FMCW algorithm processing techniques may also be applied to 2D complex matrices such as outputted by RADAR sensors utilizing FMCW chirps of various types (e.g., sawtooth ramp, triangle etc.).

5.1.3 Additional System Considerations—Speaker and/or Microphone

According to some aspects of the disclosure, the speaker and microphone may be located on the same device (e.g., on a smartphone, tablet, laptop etc.) or on different devices with a common or otherwise synchronized clock signal. Also, a synchronized clock signal may not be required if the two or more components can communicate synchronizing information over an audio channel, or via another means such as the Internet. In some solutions, the transmitter and receiver may use the same clock and then no special synchronization techniques are required. Alternative methods of realizing synchronization include utilizing a Costas loop or PLL (phase locked loop)—i.e., an approach that can "lock in to" the transmitted signal—such as a carrier signal.

It can be important to account for any buffering in the audio pathway, to understand the cumulative impact on synchronization of transmitted and received samples, in order to minimize potential unwanted low frequency artefact components. In some cases, it may be desirable to place the microphone and/or speaker near or within the bedclothes—e.g., by using a phone headset/mic plug in device (such as used to make hands-free calls). An example is the device usually bundled with Apple and Android phones. During a calibration/setup process, the system should be able to select the appropriate mic (if more than one mic is present on a phone), speaker, and amplitude and frequency settings to suit the system/environmental setup.

5.1.3.1.1 Calibration/Adaption of System to Component Variation and to the Environment It is desirable to implement a technique to optimally adapt the system parameters to the specific phone (or other mobile device) in use, the environment (e.g., bedroom) and the user(s) of the system. This implies that the system learns over time, as the apparatus may be portable (e.g., moved to another living space, bedroom, hotel, hospital, care home etc.), adapt to one or more living subjects in the sensing field, and to be compatible with a wide range of devices. This implies equalization of the audio channel.

The system can auto-calibrate to the channel conditions by learning (or indeed be pre-programmed with default) device or model specific characteristics, and channel characteristics. Device and model specific characteristics include the baseline noise characteristics of the speaker and microphone, and the ability of the mechanical components to vibrate stably at the intended frequency or frequencies, as well as the amplitude response (i.e., actual emitted volume for a target waveform, and the signal response of the receiving microphone(s)). For example, in the case of an FMCW chirp, the magnitude of the received direct path chirp may be used to estimate the sensitivity of the system, and if the signal amplitude and/or phone volume needs to be automatically adjusted to achieve a desired system sensitivity (which can be related the performance of the speaker and mic combination, including the sound pressure level (SPL) emitted by the speaker/transducer at a given phone volume). This allows the system to support many varieties of smart device, such as the large and disparate ecosystem of Android phones. This can also be used to check if the user has adjusted the phone main volume, and if this needs to be re-adjusted automatically, or the system needs to adjust to the new operating conditions. Different operating system (OS) revisions may also give rise to different characteristics, including audio buffer lengths, audio path latency, and likelihood of occasional dropouts/jitter in the Tx and/or Rx stream(s).

Key aspects of the system are captured, including ADC and DAC quantization level (available bits), signal to noise ratio, simultaneous or synchronized clocking of TX and RX, and temperature and humidity of the room (if available). For example, it may be detected that a device has an optimal sampling rate of 48 kHz and perform a sub-optimal resampling if supplied with samples at 44.1 kHz; in this case, the preferred sampling rate would be set as 48 kHz. An estimate is formed of the dynamic range of the system, and an appropriate signal composition is selected.

Other characteristics include the separation (angular and distance) between the transmit and receiving components (e.g., distance between transmitter and receiver), and the configuration/parameters of any active automatic gain control (AGC) and/or active echo cancellation. The device (especially a phone that uses multiple active mics) may implement signal processing measures that are confounded by the continual transmission of a signal, leading to unwanted oscillations in the received signal which need to be corrected (or indeed to adjust the configuration of the device where possible in order to disable the unwanted AGC or echo cancellation).

The system can be preprogrammed with the reflection coefficients of various materials versus frequency (e.g., the reflection coefficient at 18 kHz). If we consider the echo cancellation case in more detail, for CW (single tone), the signal is there continuously; thus, unless perfect acoustic isolation (unlikely on a smartphone), the TX signal is much stronger than RX, and the system may be negatively impacted by the inbuilt echo canceller in phone. A CW system may experience strong amplitude modulation due to the activity of an AGC system or basic echo canceller. As an example for a CW system on a specific handset (Samsung S4 running OS "Lollipop"), the raw signal can contain an amplitude modulation (AM) of returned signal. One strategy to address this issue is to perform very high frequency AGC on the raw samples to smooth out the AM components that are not related to the respiratory motion.

A different type of signal such as an FMCW "chirp" may defeat an echo canceller implemented in a device in an agreeable way; indeed, an (A) FHRG or UWB approach may also be robust to an acoustic echo canceller directed towards voice. In the FMCW case, a chirp is short term non stationary signal that can allow access to momentary information about the room and movement in the room at a point in time and moves on; the echo canceller chases this with a lag but it is still possible to see the returned signal. However, this behavior is related to the exact implementation of a third party echo canceller; generally speaking, it is desirable (where possible) to disable any software or hardware (e.g., in the CODEC) echo cancellation for the duration of the physiological sensing Tx/Rx usage.

Another approach is to use a continuous broadband UWB (ultra wide band) signal. Such a UWB approach is highly resilient in the case where there is not a good response at a particular frequency. A wideband signal could be constrained to an inaudible band, or spread within an audible band as a hiss; such a signal can be at a low amplitude that does not disturb a person or animal, and optionally be further "shaped" by a window to sound pleasing to the ear.

One method to create an inaudible UWB sequence is to take an audible probing sequence such as a maximum length sequence (MLS—a type of pseudorandom binary sequence) and modulate up an inaudible band. It can also be kept at audible frequency, e.g., in the case where it can be masked by an existing sound such as music etc. Due to the fact that the maximum lengths sequence needs to be repeated, the resulting sound is not pure spectrally flat white noise; in fact, it can produce a sound similar to that produced by a commercial sound machine-whilst slowing respiration rate detection of one or more persons. A pulse can either be narrow in time or narrow in autocorrelation function. Such "magic" sequences like MLS are periodic in both time and frequency; MLS specifically has an excellent autocorrelation property. By estimating the impulse response of the room, it is possible to range gate. It is necessary to pick out sub sample movement in order to recover a breathing signal of a subject in the room. This can be done using a group delay extraction method; one example is to use center of gravity (first moment) as a proxy for a filtered impulse response (i.e., the group delay of a segment corresponds to the center of gravity of the impulse response).

A channel model can be created automatically (e.g., on first use of an "app" on a smartdevice or piece of hardware) or be manually cued (initiated) by a user, and periodically or continuously monitor the channel conditions, and adapt as appropriate.

A correlation or adaptive filter (like an echo canceller) can be used to interrogate the room. Helpfully, the bit that cannot be cancelled is primarily due to movement in room. After estimating room parameters, an eigenfilter (derived by optimizing the objective function) may be used to transform the raw signal, which is then transformed by the impulse response of the room. For the case of a pseudo white noise, it is possible to shape the target masking signal to the frequency characteristics of the environmental noise and improve the sleeping experience whilst also logging biomotion data. For example, an automatic frequency evaluation of an environment may reveal undesirable standing waves at a particularly frequency, and adjust the transmitted frequency to avoid such standing waves (i.e., resonant frequencies-points of maximum and minimum movement in the air medium/pressure nodes and anti-nodes).

In contrast, flutter echo can affect sounds above 500 Hz, with significant reflections from parallel walls with hard surfaces, drywall and glass and so forth. Therefore, active noise cancelling can be applied to reduce or cancel unwanted reflections/effects seen in the environment. In terms of orientation of the device, the system setup will alert the user to the optimum position of the phone (i.e., to maximize SNR). This may require the loudspeaker of the phone to be pointed towards the chest within a particular distance range. Calibration can also detect and correct for the presence of manufacturer or third party phone covers that may alter the acoustic characteristics of the system. If the mic on the phone appears to be compromised, the user may be asked to clean the mic opening (e.g., a phone may pick up lint, dust or other material in the mic opening that can be cleaned).

According to some aspects of the disclosure, a continuous wave (CW) approach may be applied. Unlike a range gated system using time of flight, such as FMCW, UWB, or A (FHRG), CW uses a single continuous sinusoidal tone. Unmodulated CW can use the Doppler effect when objects are moving (i.e., return frequencies are shifted away from the transmitted frequency), but may be unable to evaluate distance. CW may be used, for example, for the case of a single person in bed with no other motion sources nearby, and could give a high signal to noise (SNR) in such a case. The demodulation scheme as outlined in FHRG can be used for the special case of a single tone (no frames per se) in order to recover a baseband signal.

Another approach is Adaptive CW. This is not specifically range gated (although can in effect have a limited range such as to detect the nearest person in a bed due to the fact that it is limited by Tx power, and room reverberation), and can make use of room modes. Adaptive CW maintains the use of a continuous transmitted audio tone in an inaudible range, but within the capabilities of the transmit/receive apparatus. By scanning across inaudible frequencies in steps, an algorithm iteratively searches frequencies for the best available breathing signal-both in frequency content, and also time domain morphology (breathing shape). A spacing in Tx signal of only 10 Hz may lead to quite a different shape of demodulated respiratory waveform, with the cleared morphology being most appropriate for apnea (central and obstructive) and hypopnea analysis.

Holography is concerned with wavefront reconstruction. Highly stable audio oscillators are required for holography, where the coherent source is the loudspeaker, and makes use of the fact that a room has stored energy due to reverberation (i.e., a CW signal is chosen to specifically have strong standing waves, as opposed to other approaches discussed previously that try to move out of modes, or indeed not to create standing waves at all using frequency hopping, and/or adaptive frequency selection).

For the case of a system with two or more loudspeakers, it becomes possible to adjust or steer the "beam" in a particular direction (e.g., to optimally detect a single person in a bed).

When we further consider FIG. 7, if data are stored after the high pass filter 702 (e.g., a HPF with 3 dB point at 17 kHz) for later offline analysis (versus say an online processing system that reads and discards raw audio data), the high pass filtering can act as a privacy filter, as the blocked (removed/filtered out) data in the stopband contain the primary speech information.

5.1.3.1.2 Adapting to Multiple Cooperating or Non-Cooperating Devices and to Interferers A system may comprise multiple microphones, or be required to cooperate with a system proximate system (e.g., two phones running an app placed at either side of a double bed to monitor two people independently). In other words, management of multiple transceivers is required in an environment-using the channel or another means such as a wireless signal or data transmitted via the internet to allow coexistence. Specifically, this means that waveforms may be adapted with the selected band in order to minimize interference, whether it be to adjust coding sequences or in the simplest case of a single sine wave, to detect a sine wave at approximately 18 kHz and choose to transmit at approximately 19 kHz. Thus, the device may include a setup mode which may be activated on startup to check the sound signals of the environment or vicinity of the device with signal analysis of sound of the vicinity (e.g., frequency analysis of sound received by microphone) and in response to the analysis, choose a different frequency range for operation such as a non-overlapping set of frequencies from the received sound frequencies. In this way, multiple devices may operate with the sound generation and modulation technology described herein in a common vicinity where each device generates sound signals in a different frequency range. In some cases, the different frequency ranges may still be within the low ultrasonic frequency ranges described herein.

It is less likely that FMCW would be run on more than one device in proximity at a time (vs. say CW) as FMCW on a single device can detect multiple persons; however, if more than one FMCW transmission is running in proximity in order to maximize the available SNR, the bands may be automatically (or through user intervention) adapted to be non-overlapping in frequency (e.g., 18-19 kHz, and 19.1-20.1 kHz etc.) or in time (where the chirps occupy the same frequency band as each other, but have non-overlapping quiet periods, with a guard band to allow the other device's reflections to dissipate).

When using (A) FHRG with tone pairs, it can be seen that these can be frequency and/or time dithered. Frequency dithering implies a varying frequency shift between frames, and time dithering means that the time of flight (based on changing the pulse duration) is changed. Such an approach of one or both dithering methods may include reducing the probability of room modes being generated and/or allowing two SONAR systems to coexist within "hearing" distance of each other.

One can also see that an FHRG system can be released with a pseudo random sequence defining the tones/frames-assuming that the transitions are such that audible harmonics are not introduced into the resulting transmitted signal (or that appropriate comb filtering is applied to remove/attenuate the unwanted sub harmonics).

Where the TX and RX signal are generated on different hardware, a common clock may not be available; therefore; cooperation is required. Where two or more devices are in "hearing" distance of each other, optimally employ cooperative signal selection to avoid interference. This can allow the adaption of transmitted signals to provide best return from bed clothes.

5.1.3.1.3 Adapting to User Preferences

A simple audio sweep test can allow a user to select the lowest frequency that they can no longer hear (e.g., 17.56 kHz, 19.3 KHz, 21.2 kHz etc, etc.); this (with a small guard-band offset) can be used as the start frequency for a generated signal. A pet set up process can also be included to check if a dog, cat, pet mouse or similar reacts to a sample sounds; if they do, it may be preferable to use a low amplitude audible (to humans) sound signal with modulated information. A "pet set up mode" can be implemented to check if (say) a dog responds to a particular sound, and they user can record this fact such that the system checks a different sound in order to find a signal that does not cause discomfort. Similarly, where discomfort to the user is noted, the system can configure to an alternate signal type/frequency band. White noise feature including active signal TX can be useful where pets/children do not tolerate a specific waveform and/or where a calming masking noise ("white noise"/hiss) is desired. Thus, the mode may cycle through one or more test sound signals and prompt a user for input regarding whether the tested sound signal (which may be inaudible to humans) is problematic or not, and select a frequency for use based on the input.

5.1.3.1.4 Pausing Tx Playback Automatically when a User Interacts with a Device

As the system may be playing back a high amplitude inaudible signal, it is desirable that this be muted (Tx paused) in a mobile device such as a smartdevice if the user is interacting with the device. Specifically, the device must be muted if brought up beside the user's ear (e.g., to make or receive a call). Of course, once the signal is unmuted, the system is required to resynchronize. The system may also cause a battery drain, so the following approach may be used. If the system is running, it should preferentially run only when the device is being charged; thus, the system may be designed to pause (or not start) if a smartdevice is not connected to a wired or wireless charger. In terms of pausing Tx (and processing) when the device is in use, inputs can be taken from one or more of user interaction with the phone-pressing a button, touching a screen, moving the phone (detected via an inbuilt accelerometer if present, and/or a gyroscope, and/or an infra-red proximity sensor), or a change in location as detected with GPS or assisted GPS, or an incoming call. In the case of a notification (e.g., a text or other message), where the device is not in "silent" mode, the system may temporarily pause Tx in anticipation of the user picking up the device for a period of time.

On start-up, the system may wait a period of time before activating the Tx, in order to check that the phone has been placed down on a surface, and the user is no longer interacting with it. If a range estimation approach such as FMCW is being employed, the system may reduce the Tx power level or pause (mute) Tx if a breathing movement is detected very close to the device, on the basis that the minimum possible acoustic output power should be used to meet a desired SNR level. Additionally, the recovered gesture from the demodulated baseband signal as the user reaches out for the device can be used to proactively smoothly reduce the Tx volume, before either silencing if the user actually interacts with the device, or smoothly increasing the volume to the operating level if the user withdraws their hand from the vicinity of the device.

5.1.3.1.5 Data Fusion

For a system that collects (receives) an audio signal with an active transmitted component, it is also desirable to process the full band signal in order to reject or utilize other patterns. For example, this can be used to detect speech, background noise, or other patterns that could swamp the TX signal. For respiratory analysis, it is highly desirable to carry out data fusion with extracted audio waveform characteristics of breathing; a direct detection of the breathing sound can be combined with the demodulated signal. Also, aspects of risky sleep or respiratory conditions with an audio component such as coughing, wheezing, snoring etc. can be extracted-especially for applications within the bedroom (usually a quiet environment). Breathing sounds can be from the mouth or nose, and including snoring, wheezing, gasping, whistling and so forth.

The full audio signal can also be used to estimate movement (such as a gross motion like a user rolling over in bed), and distinguish from other background non-physiologically generated noises. The SONAR estimated movement (from the processed baseband signal) and the full band passive audio signal analysis can be combined, typically with the SONAR movement (and estimated activity from that movement) taking precedence due to the advantage of range gating (range detection) in FMWC, (A) FHRG ToF etc. over a non-range specific passive acoustic analysis. The duration and intensity of detected noise can also offer insight into unwanted de-synchronizations-such as when a fan is placed in close proximity, or a heating or cooling system is excessively noisy. Acoustic fan noise may also be seen as increased 1/f signal in the SONAR baseband signal analysis. Where actual user sounds can be detected over the noise floor, but the SONAR Rx signal is of very poor quality, the system can fall back to a processing mode where physiological sounds are mapped to activity, and directly drive a reduced accuracy sleep/wake detector, based purely on these activity indices. The system may also feedback to the user on optimal fan placement, and/or adapt its frequencies of operation to bands where the interference is reduced. Other noise sources such as fluorescent tubes/bulbs and LED ballasts can be detected, and the system adapted to a more preferentially SONAR frequency(ies) of operation. Thus, the device may also process audio signals by traditional sound processing methods (in addition to the demodulation processing techniques described herein) received via the microphone to evaluate any one or more of environmental sounds, speech sounds and breathing sounds for detection of user motion and related characteristics.

Speech detection can also be used as a privacy function, in order to actively discard any temporary data that can contain private information. Processing can be performed to reject potential confounding factors-ticking analog clock, TV, streaming media on tablet, fans, air conditioning units, forced heating systems, traffic/street noise and so forth. Thus, biomotion information can be extracted from the audible spectrum, and combined with data extracted from the demodulated scheme to improve overall accuracy.

According to some aspects of the disclosure, the light sensor on a device, such as a smartphone, may provide a separate input into the system, suggesting whether the person is attempting to sleep, or is watching television, reading, using a tablet, etc. Using the temperature sensor on the phone and or available humidity sensing (or weather data based on location) can be used to augment the channel estimation/propagating of the transmitted signal. Interaction with the phone itself can provide additional information on level of alertness of user and/or fatigue state.

Understanding the motion of the sensing device via an internal motion sensor, such as a MEMS accelerometer can be used to disable the acoustic sensing processes when phone is in movement. Fusion of sensor data with accelerometer data may be used to augment movement detection.

It is noted that while the systems and methods described herein are described as being implemented by a mobile device, in other aspects of the disclosure, the systems and methods may be implemented by a fixed device. For example, the systems and methods described herein may be implemented by a bedside consumer monitoring device or a medical device, such as a flow generator (e.g., a CPAP machine) for treating sleep disordered breathing or other respiratory conditions.

5.1.3.1.6 Cardiac Information

As previously mentioned, in addition to respiration information, the sound generation and reflection analysis of the various technology versions previously described, may be implemented for other periodic information as well such as cardiac information detection or heart rate, from the produced motion-related signal. In the example of FIG. 21, cardiac decision processing may be an optionally added module. A ballistocardiogram based cardiac peak detection can be applied during the FFT based 2D processing stage (just as respiration detection is performed) but looking at a higher frequency band.

Alternatively, wavelets (as an alternative or addition to FFTs)—such as a discrete wavelet transform processing each of the I then Q signals—or simultaneously processing using a discrete complex wavelet transform can be used for the 2D processing stage to split out gross motion, respiration, and cardiac signals.

Time-frequency processing such as wavelet based methods (e.g., discretized continuous wavelet transform—DCWT—using for example Daubechies Wavelets) can perform both detrending, as well as direct body motion, respiration, and cardiac signal extraction. The cardiac activity is reflected in signals at higher frequencies, and this activity can be accessed by filtering with a bandpass filter with a pass band of a range from 0.7 to 4 Hz (48 beats per minute to 240 beats per minute). Activity due to gross motion is typically in the range 4 Hz to 10 Hz. It should be noted that there can be overlap in these ranges. Strong (clean) breathing traces can give rise to strong harmonics, and these need to be tracked in order to avoid confusing For example, signal analysis in some versions of the present technology may include any of the methodologies described in International Patent Application Publication No. WO2014/047310, the entire disclosure of which is incorporated herein by reference, including, for example, methods of wavelet de-noising of respiratory signals.

5.1.3.1.7 System Examples

In general, the technology versions of the present application may be implemented by one or more processors configured with the monitoring related methodologies such as the algorithms or methods of the modules described in the more detail herein. Thus, the technology may be implemented with integrated chips, one or more memories and/or other control instruction, data or information storage medium. For example, programmed instructions encompassing any of the methodologies described herein may be coded on integrated chips in the memory of a suitable device. Such instructions may also or alternatively be loaded as software or firmware using an appropriate data storage medium. Thus, the technology may include a processor-readable medium, or computer-readable data storage medium, having stored thereon processor-executable instructions which, when executed by one or more processors, cause the processor to perform any of the methods or aspects of the methods described herein. In some cases, a server, or other networked computing apparatus, may include or otherwise be configured to have access to such a processor-readable data storage medium. The server may be configured to receive requests for downloading the processor executable instructions of the processor-readable data storage medium to a processing device over a network. Thus, the technology may involve a method of a server having access to the processor-readable data storage medium. The server receives a request for downloading the processor executable instructions of the processor-readable data storage medium, such as for downloading the instructions to a processing device such as a computing device or portable computing device (e.g., smart phone) over a network. The server may then transmit the processor executable instructions of the computer-readable data storage medium to the device in response to the request. The device may then execute the processor executable instructions, such as if the processor executable instructions are stored on another processor-readable data storage medium of the device.

5.1.3.1.8 Other Portable or Electronic Processing Devices

As previously mentioned, the sound sensing methodologies described herein may be implemented by one or more processors of electronic processing devices or computing devices such as smart phones, laptops, portable/mobile devices, mobile phones, tablet computers, etc. These devices may be typically understood to be portable or mobile. However, other similar electronic processing devices may also be implemented with the technologies described herein.

For example, many homes and vehicles contain electronic processing devices that are capable of emitting and recording sounds such as in the low frequency ultrasonic range at just above the human hearing threshold—e.g., smart speakers, active sound bars, smart devices, other devices supporting voice and other virtual assistants. A smart speaker or similar device typically includes communication components via a wired or wireless means (such as Bluetooth, Wi-Fi, Zig Bee, mesh, peer to peer networking etc.) such as for communication to and from other home devices such as for home automation, and/or a network such as the Internet. Unlike a standard speaker that is designed to simply emit an acoustic signal, a smart speaker usually includes one or more processors and one or more speakers, as well as one or more microphones (mic(s)). The mic(s) may be used to interface to intelligent assistants (artificial intelligence (AI) systems) in order to provide personalized voice control. Some examples are Google Home, Apple HomePod, Amazon Echo, with voice activation using "OK Google", "Hey Siri", "Alexa" phrases. These devices may be portable, and may be typically intended for use at a particular location. Their connected sensors may be considered to be part of the Internet of Things (IoT). Other devices such as active sound bars (i.e., including microphones), smart televisions (which may typically be stationary devices), and mobile smart devices can also be utilized.

Such devices and systems can be adapted to perform physiological sensing using low frequency ultrasonic techniques described herein.

For devices with multiple transducers, it is possible to implement beam forming—i.e., where signal processing is employed to provide directional or spatial selectivity of signals sent to, or received from, an array of sensors (e.g., speakers). This is typically a "far field" problem where the wavefront is relatively flat for low frequency ultrasound (as opposed to medical imaging, which is "near field"). For a pure CW system, audio waves travel out from the speaker, leading to areas of maxima and minima. However, if multiple transducers are available, it becomes possible to control this radiation pattern to our advantage—an approach known as beam forming. On the receive side, multiple microphones can also be used. This allows the acoustic sensing to be preferentially steering (e.g., steering the emitted sound and/or the received sound waves) in a direction, and swept across a region. For the case of a user in bed, the sensing can be steered towards the subject—or towards multiple subjects where there are say two persons in the bed.

By way of additional example, the technologies described herein may be implemented in wearable devices such as non-invasive devices (e.g., smart watches) or even invasive devices (e.g., implant chips or implantable devices). These portable devices may also be configured with the present technology.

5.2 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the present technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilized to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A non-transitory processor-readable medium, having stored thereon processor-executable instructions which, when executed by one or more processors, cause the one or more processors to electronically detect physiological movement of a user, the processor-executable instructions comprising:

instructions that electronically control generating an electronic control signal, via a wire to a speaker coupled to an electronic processing device, to operate the speaker, using the electronic control signal, to generate a sound signal in a vicinity that includes the user, wherein the electronic control signal includes modulating frequencies with a phase-continuous repeated triangular waveform formed by a plurality of sequential frequency sweeps wherein beginnings of sweeps of the plurality of sequential frequency sweeps start at a multiple of $2\Pi$;

instructions that electronically control generating an electronic sensed sound signal, via a microphone coupled to the electronic processing device, representative of the sound signal after the sound signal has been reflected from the user;
instructions that electronically demodulate the electronic sensed sound signal; and
instructions that electronically generate an electronic breathing signal from the demodulated electronic sensed sound signal,
instructions that use the electronic breathing signal to diagnose a sleep disordered breathing condition and control treating of the sleep disordered breathing condition with a flow generator configured as a therapy device;
wherein the sound signal comprises the phase-continuous repeated triangular waveform with changing frequencies forming an inaudible sound, and
wherein the speaker is operated to produce the plurality of sequential frequency sweeps in the sound signal while avoiding audible speaker clicks.

2. The non-transitory processor-readable medium of claim 1, wherein the processor-executable instructions further comprise instructions to detect a breathing signal from a produced and reflected sound signal comprising a tone pair forming a pulse.

3. The non-transitory processor-readable medium of claim 2, wherein the sound signal comprises a sequence of frames, each frame comprising a series of tone pairs, each tone pair being associated with a respective time slot within each frame.

4. The non-transitory processor-readable medium of claim 2, wherein the tone pair comprises a first frequency and a second frequency, and wherein the first frequency and the second frequency are orthogonal to each other.

5. The non-transitory processor-readable medium of claim 3, wherein the series of tone pairs in a frame of the sequence of frames comprises a first tone pair and a second tone pair, wherein frequencies of the first tone pair are different from frequencies of the second tone pair.

6. The non-transitory processor-readable medium of claim 3, wherein a tone pair of a time slot of the frame has a zero amplitude at a beginning and an end of the time slot and has a ramping amplitude to and from a peak amplitude between the beginning and the end.

7. The non-transitory processor-readable medium of claim 3, wherein a time width of the each frame varies.

8. The non-transitory processor-readable medium of claim 3, wherein a sequence of tone pairs of a frame of time slots form a pattern of different frequencies with respect to different time slots of the frame.

9. The non-transitory processor-readable medium of claim 3, wherein a duration of a respective time slot of the frame is equal to one divided by a difference between frequencies of the tone pair.

10. The non-transitory processor-readable medium of claim 1, further comprising instructions to vary one or more parameters of a form of the repeated waveform wherein the one or more parameters comprises any one or more of (a) a location of a peak in a repeated portion of the repeated waveform, (b) a slope of a ramp of a repeated portion of the repeated waveform, and (c) a frequency range of a repeated portion of the repeated waveform.

11. The non-transitory processor-readable medium of claim 1, wherein the speaker is coupled to the electronic processing device by a wireless link.

12. The non-transitory processor-readable medium of claim 1, wherein the triangular waveform is a symmetric triangular waveform.

13. The non-transitory processor-readable medium of claim 1, wherein the processor-executable instructions further comprise:
instructions to calibrate the detection of physiological movement by an assessment of one or more characteristics of the electronic processing device; and
instructions to generate the sound signal, via the speaker coupled to the electronic processing device, based on the assessment.

14. The non-transitory processor-readable medium of claim 1, wherein the therapy device is a positive airway pressure therapy device.

15. A server with access to the non-transitory processor-readable medium of claim 1, wherein the server is configured to receive requests for downloading the processor-executable instructions of the non-transitory processor-readable medium to the electronic processing device over a network.

16. A device comprising: the non-transitory processor-readable medium of claim 1, the device further comprising the one or more processors; the speaker coupled to the one or more processors; and the microphone coupled to the one or more processors, wherein the device comprises the electronic processing device.

17. A method of a server having access to the non-transitory processor-readable medium of claim 1, the method comprising receiving, at the server, a request for downloading the processor-executable instructions of the non-transitory processor-readable medium to the electronic processing device over a network; and transmitting the processor-executable instructions to the electronic processing device in response to the request.

18. A method for detecting body movement comprising:
accessing, with the one or more processors, the non-transitory processor-readable medium of claim 1,
executing, in the one or more processors, the processor-executable instructions of the non-transitory processor-readable medium.

19. A method for detecting movement and breathing using an electronic device, comprising:
transmitting, via a speaker on the electronic device, a sound signal towards a user, wherein an electronic control signal is generated, via a wire to the speaker, to operate the speaker, using the electronic control signal, to generate the sound signal in a vicinity that includes the user, wherein the electronic control signal includes modulating frequencies with a phase-continuous repeated triangular waveform formed by a plurality of sequential frequency sweeps wherein beginnings of sweeps of the plurality of sequential frequency sweeps start at a multiple of $2\pi$;
generating an electronic sensing signal, via a microphone on the electronic device, representative of a reflected sound signal, the reflected sound signal being the sound signal after the sound signal has been reflected from the user; and
electronically demodulating the electronic sensing signal representative of the reflected sound signal to generate an electronic breathing and motion signal from the reflected sound signal,
use the electronic breathing signal to diagnose a sleep disordered breathing condition and control treating of the sleep disordered breathing condition with a flow generator configured as a therapy device, wherein the speaker is operated to produce the plurality of sequential frequency sweeps in the sound signal while avoiding audible speaker clicks.

20. The method of claim 19, wherein the sound signal is an inaudible sound signal.

21. The method of claim 19, prior to transmitting, modulating the sound signal using one of a frequency modulation continuous wave (FMCW) modulation scheme, a frequency hopping range gating (FHRG) modulation scheme, an adaptive frequency hopping range gating (AFHRG) modulation scheme, a continuous wave (CW) modulation scheme, a ultra wideband (UWB) modulation scheme, or an adaptive continuous wave (ACW) modulation scheme.

22. The method of claim 19, wherein the sound signal is a modulated low frequency ultrasonic sound signal comprising a plurality of frequency pairs transmitted as a frame.

23. The method of claim 19, further comprising:
wherein the electronically demodulating comprises:
performing a filter operation on the reflected sound signal; and
synchronizing the filtered reflected sound signal with timing of the transmitted sound signal.

24. The method of claim 23, wherein the filter operation is a high pass filter operation.

25. The method of claim 19, wherein the electronic device is a mobile electronic device and wherein generating the sound signal comprises:
performing a calibration function to assess one or more characteristics of the mobile electronic device; and
generating the sound signal based on the calibration function.

26. The method of claim 25, wherein the calibration function is configured to determine at least one hardware, environment, or user specific characteristic.

27. The method of claim 19, wherein the transmitting, generating the electronic sensing signal, and electronically demodulating are performed at a bedside device.

28. The method of claim 27, wherein the bedside device is a continuous positive airway pressure (CPAP) device.

29. The method of claim 19, wherein the therapy device is a positive airway pressure therapy device.

30. An electronic device to detect physiological movement of a user, the electronic device comprising:
one or more processors;
a speaker coupled to the one or more processors;
a microphone coupled to the one or more processors;
wherein the one or more processors are configured to:
control generation of an electronic control signal to operate the speaker so that the speaker, using the electronic control signal, generates a sound signal in a vicinity that includes the user, wherein the electronic control signal includes modulating frequencies with a phase-continuous repeated triangular waveform formed by a plurality of sequential frequency sweeps wherein beginnings of sweeps of the plurality of sequential frequency sweeps start at a multiple of $2\pi$;
control generation of an electronic sensed sound signal, via the microphone, representative of the sound signal after the sound signal has been reflected from the user;
demodulate the electronic sensed sound signal;
generate an electronic breathing signal from the demodulated electronic sensed sound signal;
use the electronic breathing signal to diagnose a sleep disordered breathing condition; and
control treating of the sleep disordered breathing condition with a flow generator configured as a therapy device,
wherein the speaker is operated to produce the plurality of sequential frequency sweeps in the sound signal while avoiding audible speaker clicks.

31. The electronic device of claim 30, wherein the sound signal is in an inaudible sound range.

32. The electronic device of claim 30, wherein the one or more processors is further configured to detect a breathing signal from a sound signal, produced from the speaker, that comprises a tone pair forming a pulse.

33. The electronic device of claim 32, wherein the tone pair comprises a first frequency and a second frequency, wherein the first frequency and second frequency are different.

34. The electronic device of claim 33, wherein the first frequency and second frequency are orthogonal to each other.

35. The electronic device of claim 30, wherein the one or more processors is further configured to detect a breathing signal from a sound signal, produced from the speaker, that comprises a sequence of frames, each frame comprising a series of tone pairs, each tone pair being associated with a respective time slot within the each frame.

36. The electronic device of claim 35, wherein the series of tone pairs in a frame of the sequence of frames comprises a first tone pair and a second tone pair, wherein frequencies of the first tone pair are different from frequencies of the second tone pair.

37. The electronic device of claim 35, wherein a tone pair of a time slot of the frame has a zero amplitude at a beginning and an end of the time slot and has a ramping amplitude to and from a peak amplitude between the beginning and the end.

38. The electronic device of claim 35, wherein a time width of the frame varies.

39. The electronic device of claim 30, wherein the one or more processors is further configured to detect a breathing signal from a sound signal, produced from the speaker, that comprises a sequence of tone pairs of a frame of slots form a pattern of different frequencies with respect to different slots of each frame.

40. The electronic device of claim 30, wherein the therapy device is a positive airway pressure therapy device.

* * * * *